(12) United States Patent
Feng

(10) Patent No.: US 11,634,686 B2
(45) Date of Patent: Apr. 25, 2023

(54) METHOD OF PRODUCING NAIVE PLURIPOTENT STEM CELLS

(71) Applicant: Jian Feng, Getzville, NY (US)

(72) Inventor: Jian Feng, Getzville, NY (US)

( * ) Notice: Subject to any disclaimer, the term of this patent is extended or adjusted under 35 U.S.C. 154(b) by 1004 days.

(21) Appl. No.: 16/346,534

(22) PCT Filed: Nov. 1, 2017

(86) PCT No.: PCT/US2017/059555
§ 371 (c)(1),
(2) Date: Apr. 30, 2019

(87) PCT Pub. No.: WO2018/085419
PCT Pub. Date: May 11, 2018

(65) Prior Publication Data
US 2020/0056150 A1    Feb. 20, 2020

Related U.S. Application Data

(60) Provisional application No. 62/415,870, filed on Nov. 1, 2016.

(51) Int. Cl.
*C12N 5/074* (2010.01)

(52) U.S. Cl.
CPC ...... *C12N 5/0607* (2013.01); *C12N 2501/235* (2013.01); *C12N 2501/33* (2013.01); *C12N 2506/02* (2013.01); *C12N 2506/45* (2013.01)

(58) Field of Classification Search
CPC ............ C12N 5/0607; C12N 2501/235; C12N 2501/33; C12N 2506/02; C12N 2506/45
See application file for complete search history.

(56) References Cited

U.S. PATENT DOCUMENTS

| | | |
|---|---|---|
| 8,962,322 B2 | 2/2015 | Shi et al. |
| 2010/0330677 A1 | 12/2010 | Smith et al. |
| 2013/0189775 A1 | 7/2013 | Fang et al. |
| 2013/0295579 A1 | 11/2013 | Xie et al. |
| 2014/0010801 A1 | 1/2014 | Niedernhofer et al. |
| 2014/0018415 A1 | 1/2014 | Rinsch et al. |
| 2014/0093486 A1 | 4/2014 | Chiou et al. |
| 2015/0275171 A1 | 10/2015 | Kato et al. |
| 2016/0340642 A1 | 11/2016 | Gundry et al. |
| 2017/0114323 A1 | 4/2017 | Theunissen et al. |
| 2017/0191038 A1 | 7/2017 | Deng et al. |
| 2018/0080009 A1 | 3/2018 | Okano et al. |

FOREIGN PATENT DOCUMENTS

| | | |
|---|---|---|
| WO | 2013/174794 A1 | 11/2013 |
| WO | 2015/196072 A2 | 12/2015 |
| WO | 2016/016894 A1 | 2/2016 |
| WO | 2016/027099 A2 | 2/2016 |
| WO | 2016055519 A1 | 4/2016 |
| WO | 2016079146 A1 | 5/2016 |
| WO | 2016086105 A1 | 6/2016 |
| WO | 2016179243 A1 | 11/2016 |
| WO | 2017127755 A1 | 7/2017 |
| WO | 2017134628 A1 | 8/2017 |

OTHER PUBLICATIONS

Ng et al., A protocol describing the use of a recombinant protein-based, animal product-free medium (APEL) for human embryonic stem cell differentiation as spin embryoid bodies, Nature Protocols, 3(5): 768-776. (Year: 2008).*
Crespo et al., Mitochondrial reactive oxygen species mediate cardiomyocyte formation from embryonic stem cells in high glucose, Stem Cells, 28: 1132-1142. (Year: 2010).*
Van der Valk et al., Optimization of chemically defined cell culture media—Replacing fetal bovine serum in mammalian in vitro methods, Toxicology in Vitro, 24: 1053-1063. (Year: 2010).*
Gafni et al., Derivation of novel human ground state naïve pluripotent stem cells, Nature, 504: 282-286. (Year: 2013).*
Zhou et al., Activation of lysosomal function in the course of autophagy via mTORC1 suppression and autophagosome-lysosome fusion, Cell Research, 23: 508-523. (Year: 2013).*
Tang et al., mTOR, autophagy, and reprogramming, Frontiers in Cell and Developmental Biology, 1(4): 1-2. (Year: 2014).*
Chen, T. et al., Rapamycin and other longevity-promoting compounds enhance the generation of mouse induced pluripotent stem cells, Aging Cell, Jun. 14, 2011, vol. 10, pp. 908-911.
Lamming, D. W., et al., Rapalogs and mTor inhibitors as anti-aging therapeutics, The Journal of Clinical Investigation, Mar. 2013, vol. 123, No. 3, pp. 980-989.
Zullo, A. J., et al., Mammalian target of Rapamycin inhibition and mycobacterial survival are uncoupled in murine macrophages, BMC Biochemistry, Feb. 14, 2014, No. 14, No. 4, pp. 1-10.
Hu, Z., et al., Generation of Naivetropic Induced Pluripotent Stem Cells from Parkinson's Disease Patients for High-Efficiency Genetic Manipulation and Disease Modeling, Stem Cells and Development, Jul. 28, 2015, vol. 24, No. 21, pp. 2591-2604.

* cited by examiner

*Primary Examiner* — Laura Schuberg
*Assistant Examiner* — Joseph Paul Miano
(74) *Attorney, Agent, or Firm* — Hodgson Russ LLP

(57) ABSTRACT

Provided herein are compositions and methods for generation of naive human pluripotent stem cells. The method comprises incubation of iPSCs under 5% $O_2$ in a medium comprising 5% glucose, an MEK inhibitor, a GSK3β inhibitor, human leukemia inhibitory factor (LIF), human insulin and Torin 1. The method does not need any other inhibitors or transgene expression. The naive human pluripotent cells can be used to generate a large amount of mature human cells from all three germ layers in host non-human animals.

2 Claims, 36 Drawing Sheets
Specification includes a Sequence Listing.

k l m a naive H9, passage 12, 46 XX b naive RUES2, passage 15, 46 XX

| a | First Round | | Second round | | Third Round | |
|---|---|---|---|---|---|---|
| Naive hPSC | nRUES2 | nRUES2::GFP | nRUES2 | nRUES2::GFP | nC005::GFP | nN004::GFP |
| Blastocysts injected | 18 | 18 | 18 | 19 | 14 | 18 |
| Gestation duration (d) | 10.5 | 10.5 | 17.5 | 17.5 | 17.5 | 17.5 |
| Embryos retrieved | 11 | 0 | 4 | 14 | 4 | 3 |
| Chimera (by PCR) | 0 | 0 | 0 | 14 | N.D. | N.D. |
| Chimera (by staining) | N.D. | 0 | N.D. | 13 out of 13 | 4 out of 4 | 3 out of 3 |

N.D.: Not Determined

METHOD OF PRODUCING NAIVE PLURIPOTENT STEM CELLS

CROSS-REFERENCE TO RELATED APPLICATIONS

This application claims priority to U.S. Provisional Application No. 62/415,870, filed on Nov. 1, 2016, the disclosure of which is incorporated herein by reference.

BACKGROUND OF THE INVENTION

Mouse embryonic stem cells (mESCs) are in naive pluripotency that represents the ground state of development, from which all cells in the mouse embryo are derived. In contrast, human embryonic stem cells (hESCs) are in a primed state of pluripotency with many different properties. Despite intense efforts to generate naive human pluripotent stem cells (hPSCs), it has heretofore not been possible to derive and maintain naive hPSCs that can be used to generate a large amount of mature human cells in a non-human animal.

SUMMARY OF THE DISCLOSURE

The present disclosure provides methods for producing naive human pluripotent stem cells, which can be used to generate a substantial amount of desired types of human cells in host non-human animals. The method comprises exposing human iPSCs or human ESCs to Torin1 for a short period of time, in the presence of MEK inhibitor, a GSK inhibitor, leukemia inhibitory factor (LIF) and insulin. It is preferable to use low glucose culture medium (containing about 5% glucose) under an environment of about 5% oxygen. After the short exposure to Torin1, the cells can be continued in culture and after about 5 days, naive hPSCs can be obtained.

The naive hPSCs can be used to generate substantial amounts of desired human cells (of all three germ layers) by implanting the cells in the blastocyst of a non-human animal to form chimeras. The generated human cells or tissues can then be isolated from the host animals and used.

The present disclosure also provides a cell, or a population of cells produced by the methods of the present disclosure.

The present disclosure also provides a culture medium comprising Torin 1. The culture medium is a serum-free medium comprising about 5% glucose and further comprising or consisting essentially of a MEK inhibitor, a GSK3 inhibitor, LIF, insulin and Torin1.

The present disclosure also provides a method of producing mature human cells in a non-human animal thereby generating chimeras. The method comprises: generating human iPSCs from somatic cells of an individual, contacting the human iPSCs in culture with a culture medium comprising 5% glucose, an MEK inhibitor, a GSK3β inhibitor, LIF, insulin (termed herein as 2iLI medium) and Torin 1 for a short period of time (such as from 1 to 24 hours), and under an environment comprising about 5% $O_2$. Following treatment with Torin 1, the cells are continued to be cultured in a medium of the same composition as 2iLI medium, but without added Torin 1 to generate naive human pluripotent stem cells. In about to 7 days, colonies of naive human pluripotent stem cells can be collected and stored for later use (including storage by freezing) or can be implanted into a blastocyst of a non-human animal. The blastocyst is then allowed to grow leading to growth of chimeras in which a substantial amount of human cells can be identified.

(2005)). (d-e) SNP-based biallelic expression analysis of X-inactivated genes (d) and X-escaped genes (e) in naive H9 (nH9) and primed H9 (H9).

Figure 4:
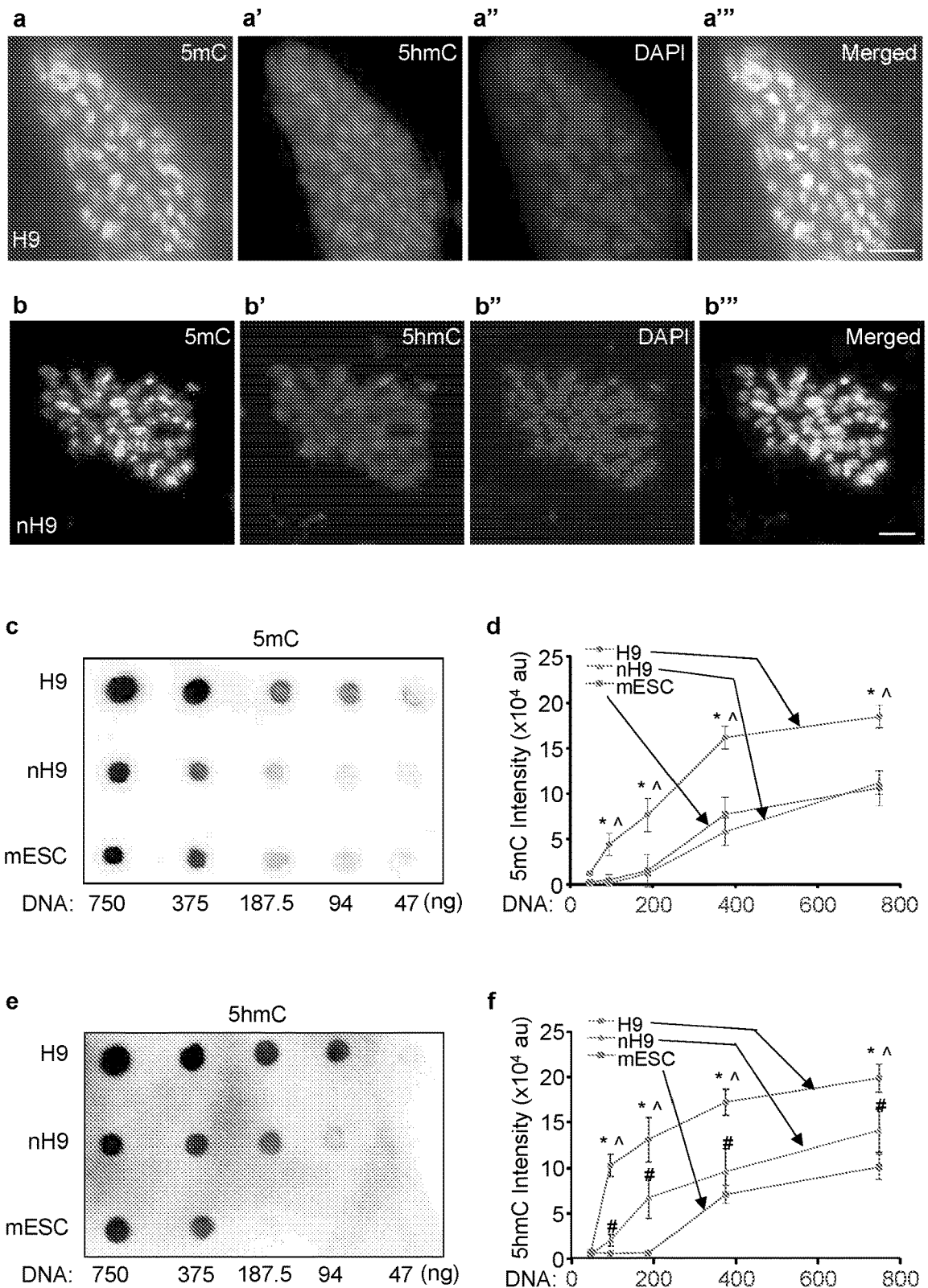
Figure 4:
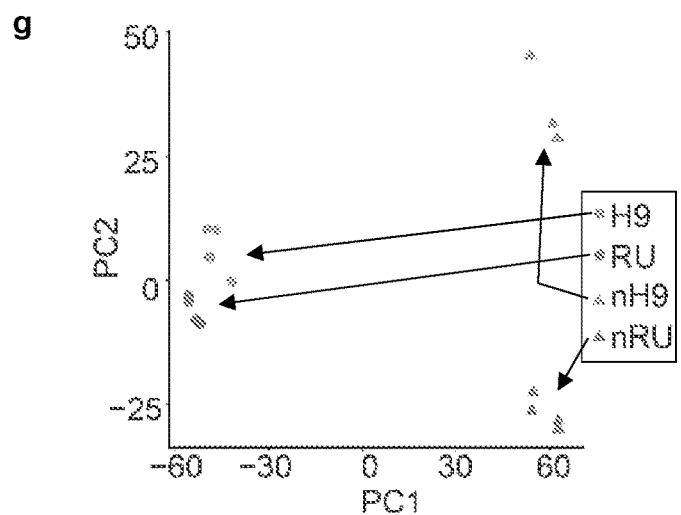
Figure 4:
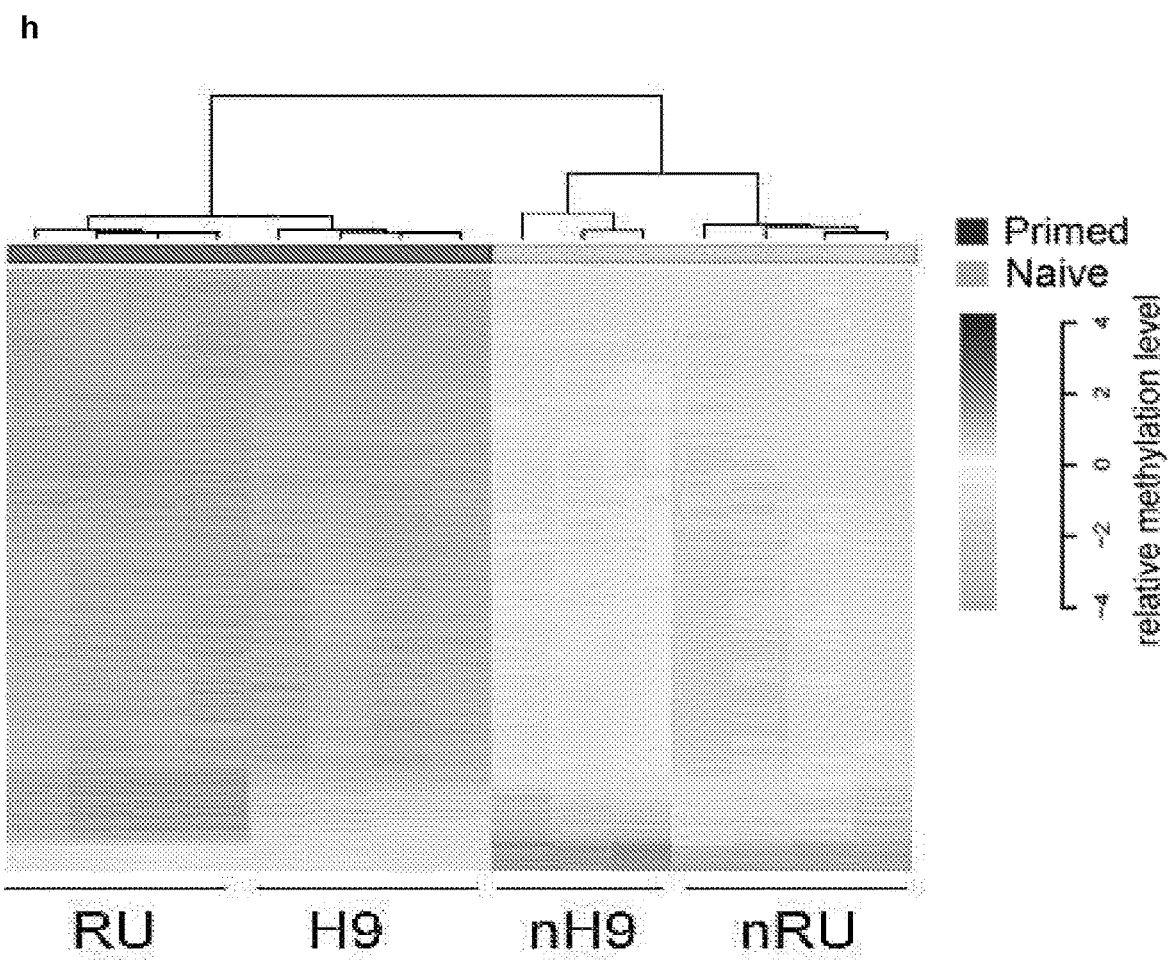
Figure 4:
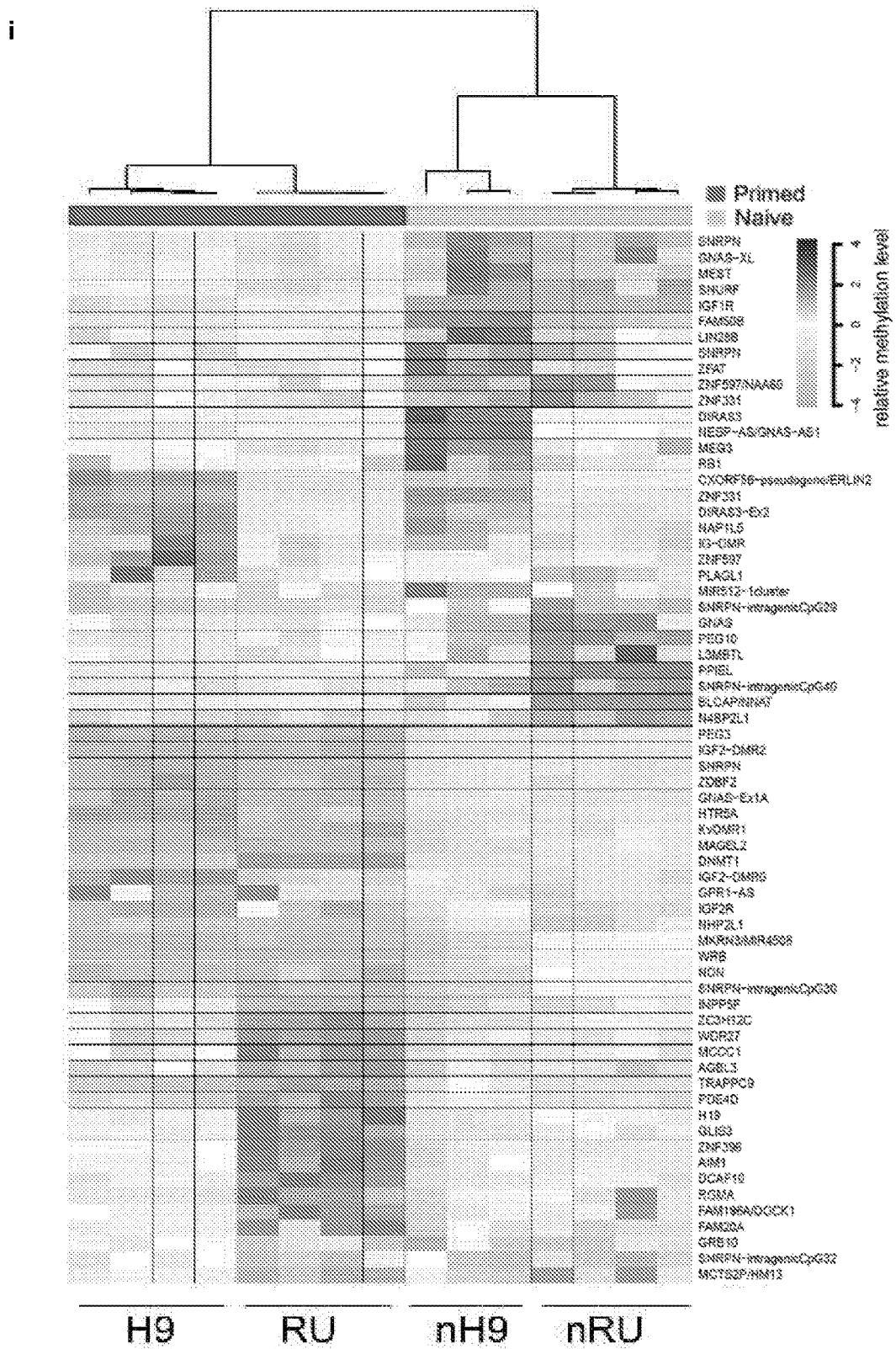

FIG. 4. Decreased DNA methylation in naive hPSCs. (a-b''') Costaining for 5mC (a, b), 5hmC (a', b') and DAPI (a'', b'') in primed H9 (a-a''') and naive H9 (b-b'''). Bars, 10 μm. (c-f) Dot blots (c, e) and quantification (d, f) of 5mC (c, d) and 5hmc (e, f) levels in genomic DNA isolated from primed and naive H9, and AB2.2 mouse ESC. *, H9 vs. mESC; ˆ, H9 vs. nH9; #, nH9 vs mESC, all at p<0.05, n=3, unpaired, two-tailed t-test. (g) PCA analysis of genome-wide DNA methylation in primed and naive H9 and RUES2 using 3 values of all probes in Infinium MethylationEPIC BeadChip. (h) Comparison of DNA methylation levels in the 128,383 tiling regions that were differentially methylated between primed and naive H9 and RUES2. (i) Comparison of DNA methylation levels in imprinted regions (Cour et al., *Genome Res.* 24, 554-569 (2014) between primed and naive H9 and RUES2. H9, primed H9; nH9, naive H9; RU, RUES2; nRU, naive RUES2.

Figure 5:
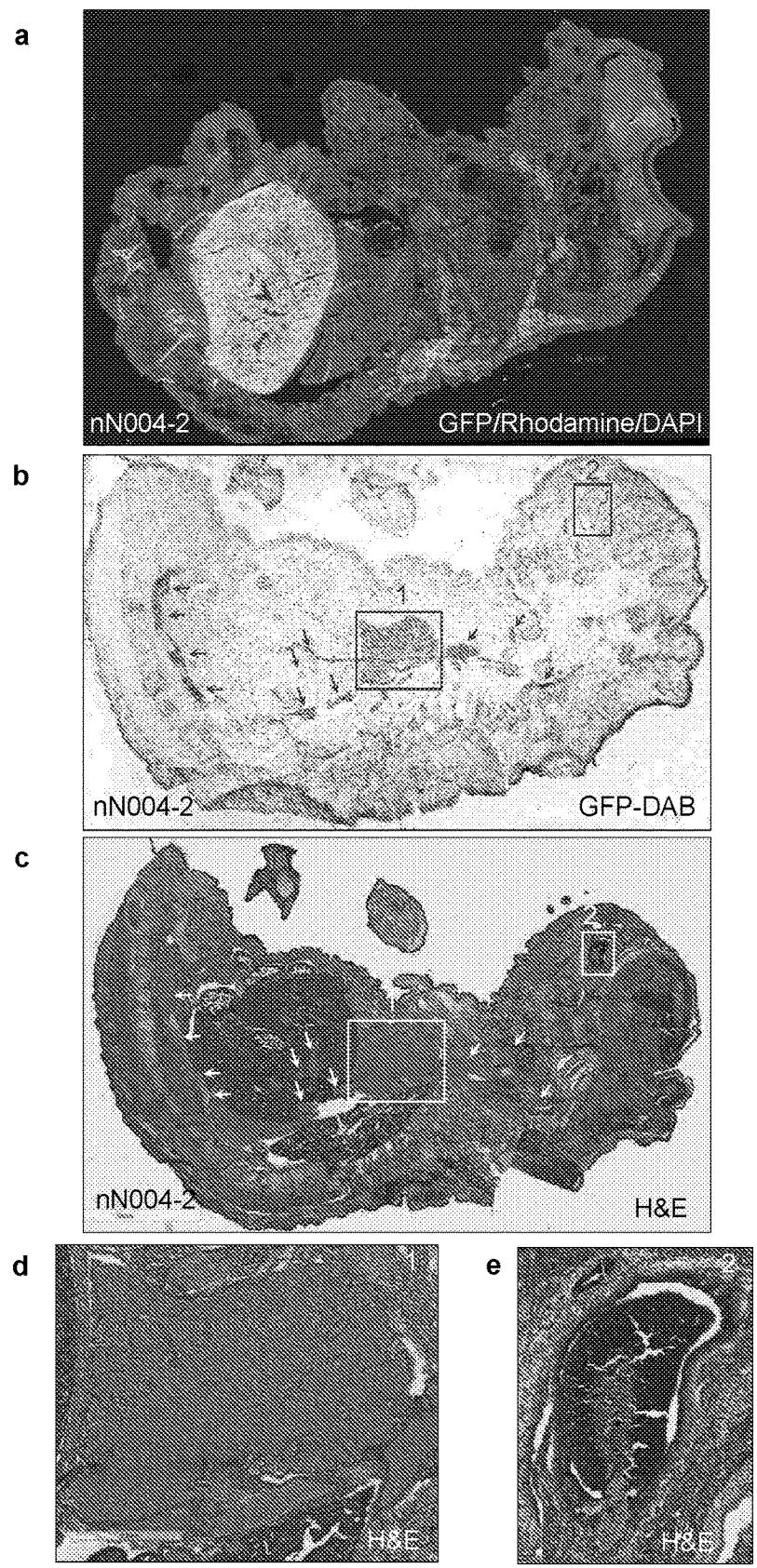
Figure 5:
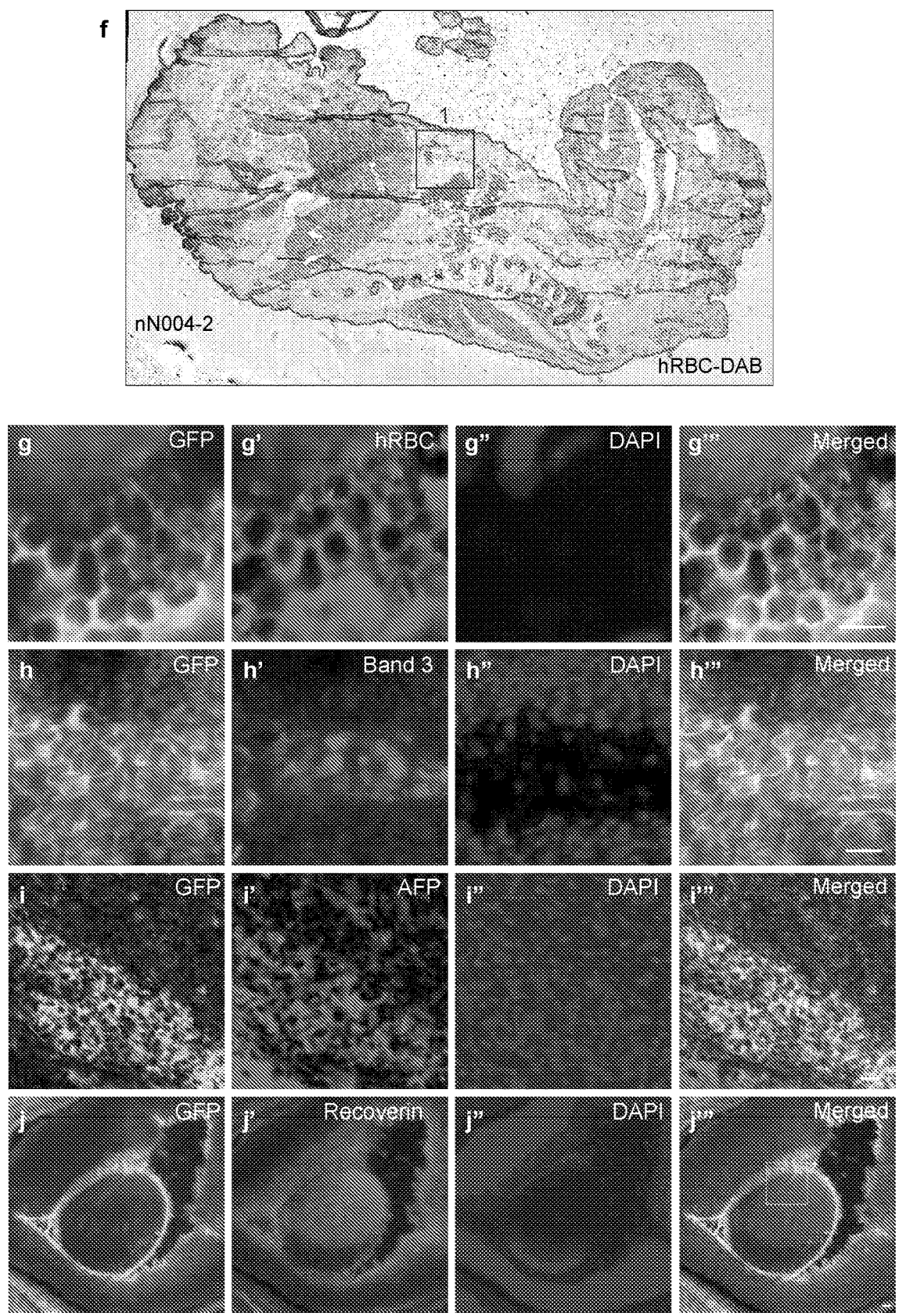
Figure 5:
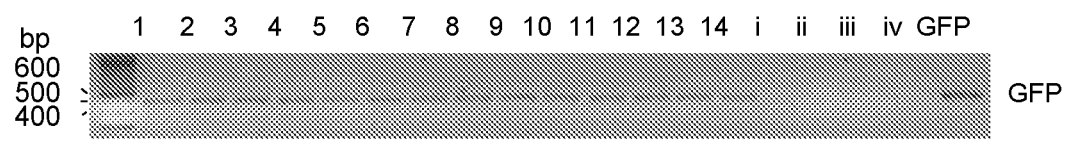
Figure 5:
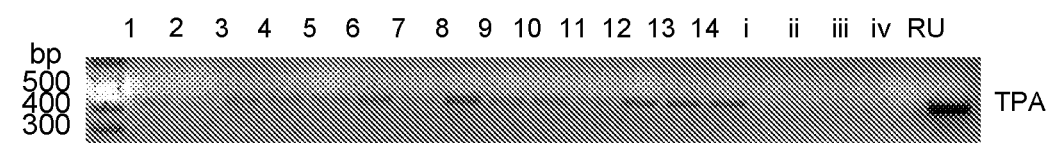
Figure 5:
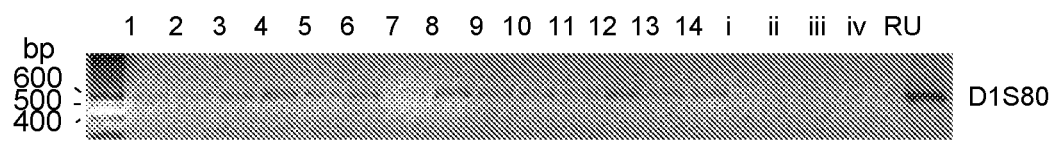

FIG. 5. Robust formation of mouse-human chimeric embryos. (a) Large amounts of GFP+ human cells were found in a mouse embryo (nN004-2) derived from blastocysts injected with GFP-labeled naive N004 iPSCs. See Supplementary FIG. 8a-d for separate channels. (b-e) At a different z-level from (a), two neighboring sections of this embryo were DAB-stained with anti-GFP (b) or stained with H&E (c). Boxes 1 and 2 in (b) correspond to boxes 1 and 2 in (c), which are enlarged in (d) and (e), respectively. Areas highlighted by arrows and box 1 contained GFP+ (b) red blood cells (RBC) (c, d). Box 2 contained GFP+ (b) retinal pigmented epithelium (c, e). (f-j''') Different sections of this embryo were DAB-stained with antibody against human Red Blood Cells (hRBC) (f) or immunostained for GFP (g, h, i, j), hRBC (g', mesoderm), the RBC marker Band 3 anion transporter (h', mesoderm), AFP (i', endoderm), the photoreceptor marker recoverin (j', ectoderm). Note the lack of DAPI in enucleated human RBC (g'', h''). g-g''' correspond to boxed areas of FIG. 13c-c'''. Boxed area in j''' is enlarged in FIG. 13d. Bars, 10 μm. (k-m) PCR detection of GFP (k) or human-specific DNA using DNA fingerprinting primers TPA-25 (l) or D1S80 (m) in genomic DNA isolated from mouse embryos derived from mouse blastocysts injected with GFP-labeled naive RUES2 (embryos 1-14) or unlabeled naive RUES2 (embryos i-iv). GFP, GFP plasmid as positive control; RU, genomic DNA from RUES2.

Figure 6:
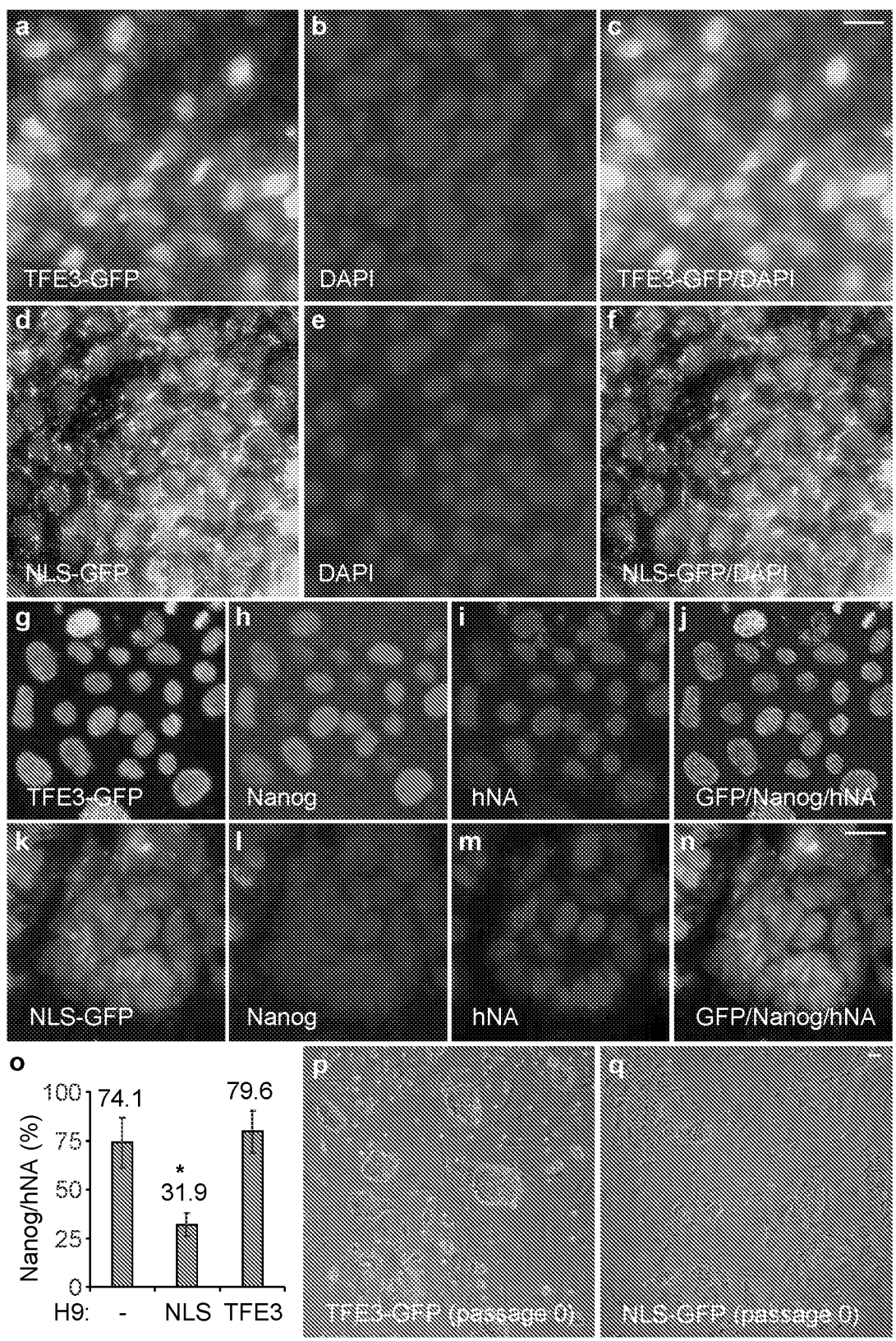

FIG. 6. Nuclear localization of TFE3 is critical for converting primed to naive pluripotency. (a-f) Primed H9 hESCs stably expressing TFE3-GFP fusion proteins (a-c) or nuclear localization signal mutated TFE3-GFP (NLS-GFP) (d-f) were costained for GFP (a, c, d, f) and DAPI (b, e). (g-q) Primed H9 hESCs stably expressing TFE3-GFP (g-j) or NLS-GFP (k-n) went through the conversion protocol in FIG. 1j and were stained at day 5 for GFP (g, k), Nanog (h, l), hNA (i, m). Merged images (j, n) were quantified for the percentage of Nanog+ cells in human Nuclear Antigen (hNA+) cells (o). *, p<0.05, n=4, one-way ANOVA, vs. control H9. Phase contrast images of H9 expressing TFE3-GFP (p) or NLS-GFP (q) were acquired at day 5 of conversion. Bars, 10 μm.

Figure 7:
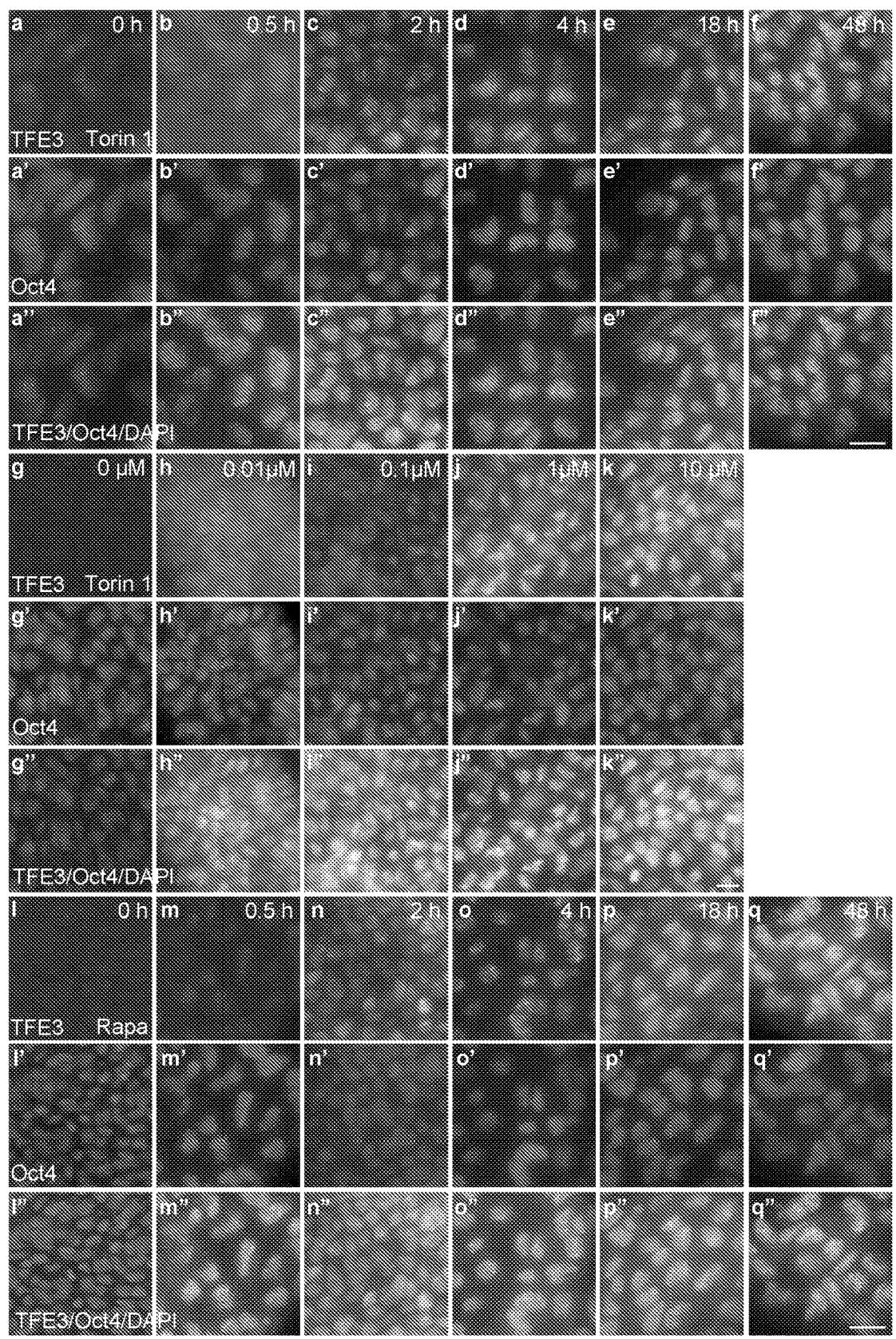

FIG. 7. Torin1 or rapamycin induces nuclear translocation of TFE3. (a-f'') Subcellular localization of TFE3 in primed H9 hESCs treated with 10 mM Torin1 at the indicated time points (a-f). Localization of Oct4 (a'-f') is merged with that of TFE3 and DNA (a''-f''). (g-k''') Subcellular localization of TFE3 in primed H9 hESCs treated with Torin1 for 10 hr at the indicated concentrations (g-k). Localization of Oct4 (g'-k') is merged with that of TFE3 and DNA (g''-k''). (l-q'') Subcellular localization of TFE3 in primed H9 hESCs treated with 10 mM Rapamycin at the indicated time points (l-q). Localization of Oct4 (l'-q') is merged with that of TFE3 and DNA (l''-q''). Bars, 10 mm.

Figure 8:
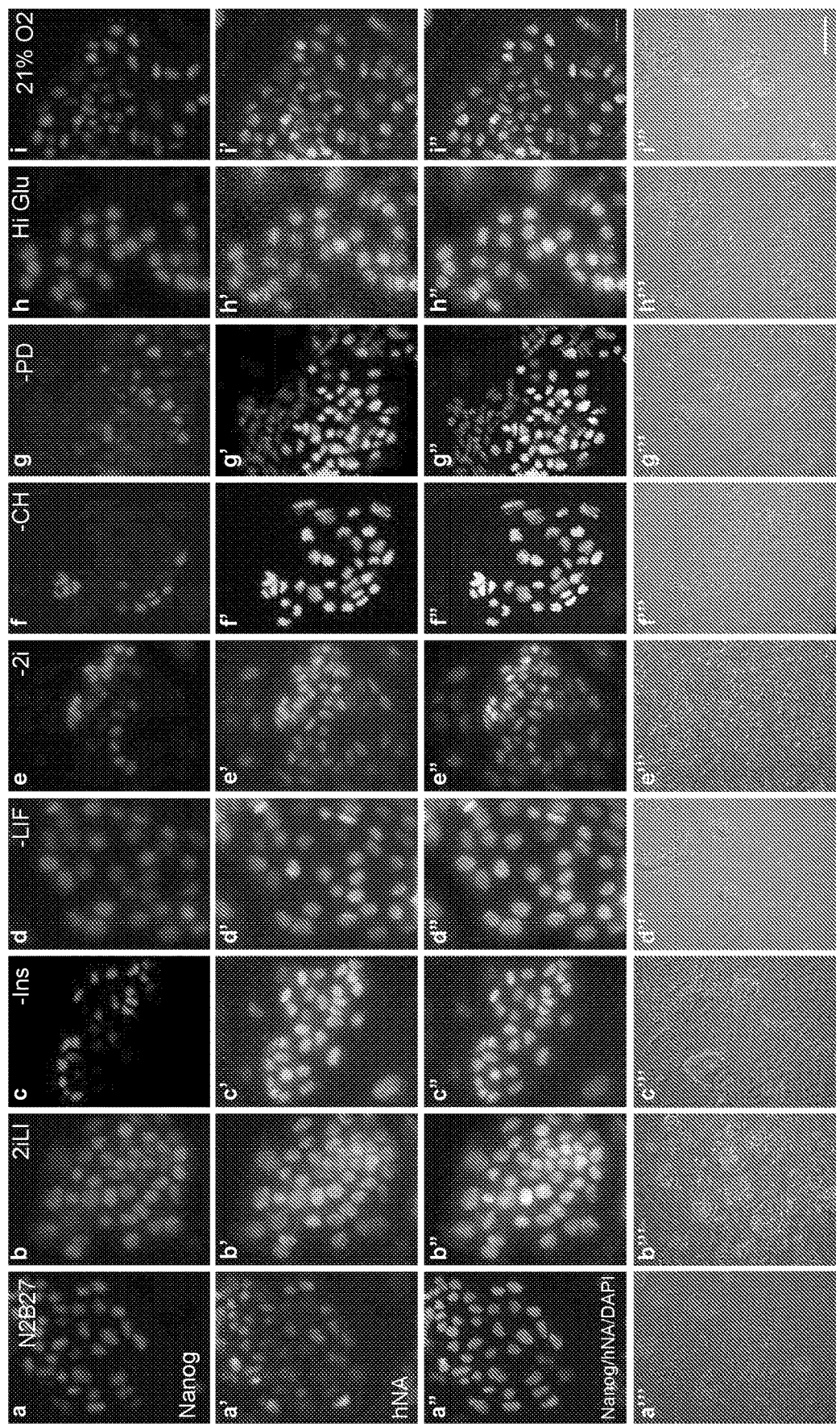
Figure 8:
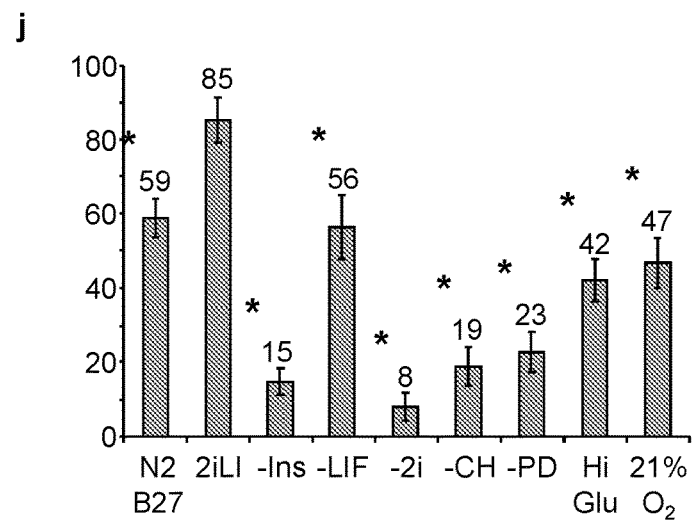
Figure 8:
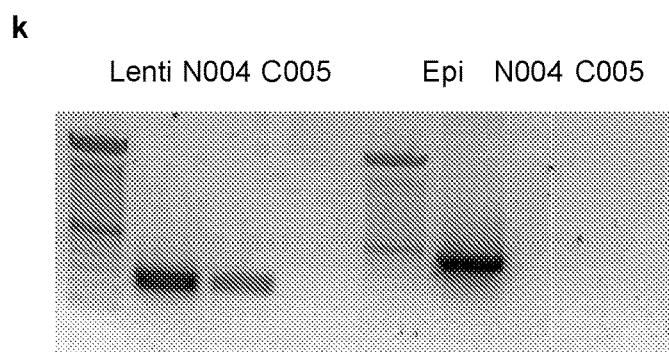
Figure 8:
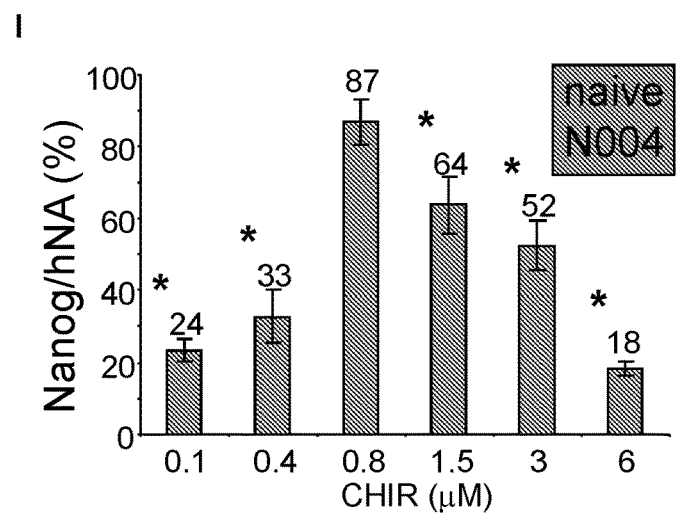

FIG. 8. Optimal conditions for converting primed hPSCs to naive state. (a-i''') After primed hPSCs were treated in 2iLI medium with Torin1 for 3 hr, trypsinized single cells were plated on MEF and cultured in the indicated conditions for 5 days and stained for Nanog (a-i), human nuclear antigen (hNA) (a'-i'), and DNA (a''-i''), or imaged under phase contrast (a'''-i'''). Red bar, 10 mm; white bar, 100 mm. (j) The percentage of human cells (hNA+) that were Nanog+ was quantified for each condition. N2B27: naive mESC medium with N2 and B27 supplements and 21.25 mM glucose; 2iLI: 1 mM PD0325091+3 mM CHIR99021+20 ng/ml hLIF+18 mg/ml human Insulin in 5 mM glucose medium and 5% $O_2$; LIF, human Leukemia Inhibitory Factor; 2i: PD0325091+CHIR99021; CH: CHIR99021; PD: PD0325091; Ins: human Insulin; Hi Glu: high glucose (21.25 mM). *, p<0.05, n=5, one-way ANOVA, vs. 2iLI. (k) PCR of N004 and C005 iPSCs for the detection of lentiviral transgenes (Lenti) or episomal plasmids (Epi). (l) Titration of optimal concentration of CHIR99021 (CHIR) for the derivation of naive N004 iPSCs by quantifying the percentage of human cells positive for Nanog. All other conditions remained the same as in 2iLI medium. *, p<0.05, n=5, one-way ANOVA, vs. 0.8 mM.

Figure 9:
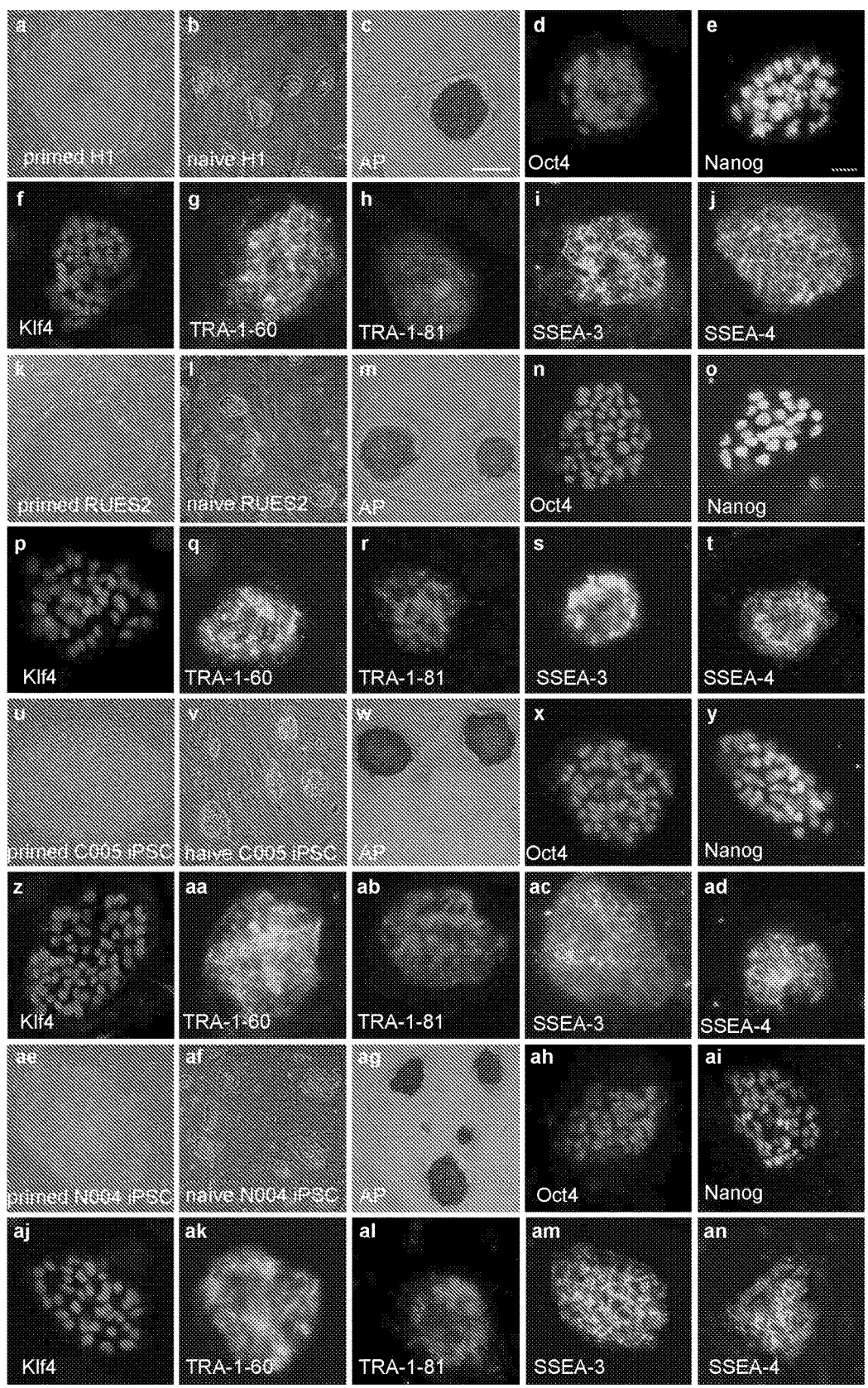

FIG. 9. Additional hPSCs are converted from primed to naive state. (a-j) H1 hESCs were converted from primed state (a) to naive state (b), which was examined by staining for the indicated pluripotency markers (c-j). (k-t) RUES2 hESCs were converted from primed state (k) to naive state (l), which was examined by staining for the indicated pluripotency markers (m-t). (u-ad) C005 human iPSCs were converted from primed state (u) to naive state (v), which was examined by staining for the indicated pluripotency markers (w-ad). (ae-an) N004 human iPSCs were converted from primed state (ae) to naive state (af), which was examined by staining for the indicated pluripotency markers (ag-an). Grey bar, 10 mm; white bar, 100 mm.

Figure 10:
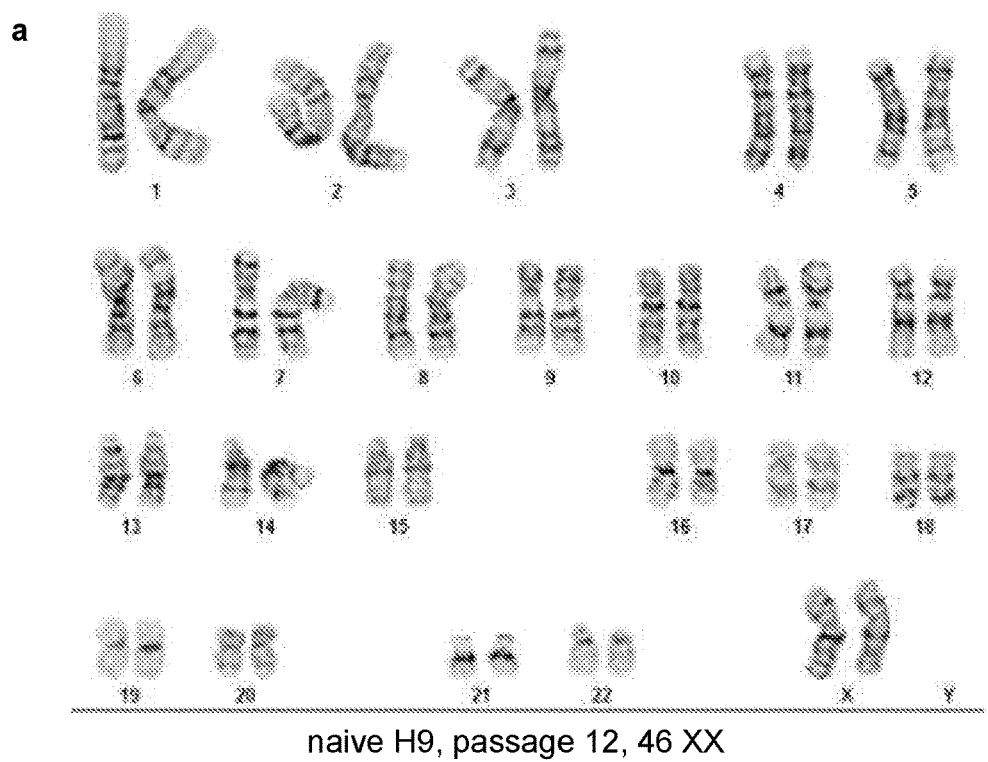
Figure 10:
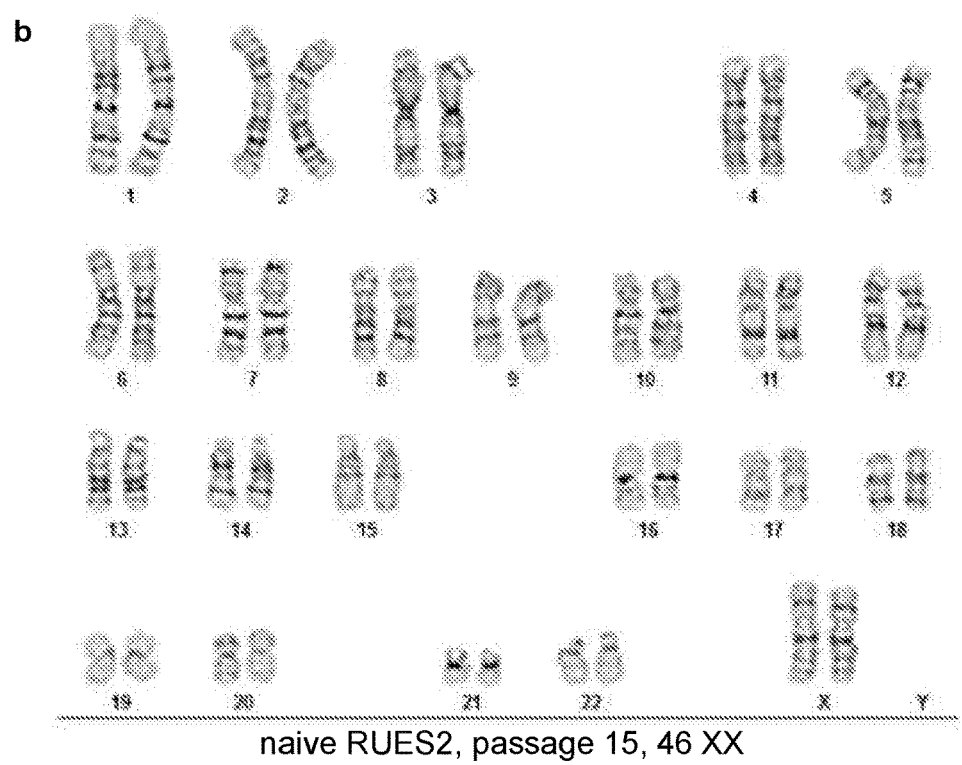

FIG. 10. Karyotype of naive hESCs. (a) Normal karyotype of naive H9 at passage 12. (b) Normal karyotype of naive RUES2 at passage 15.

Figure 11:
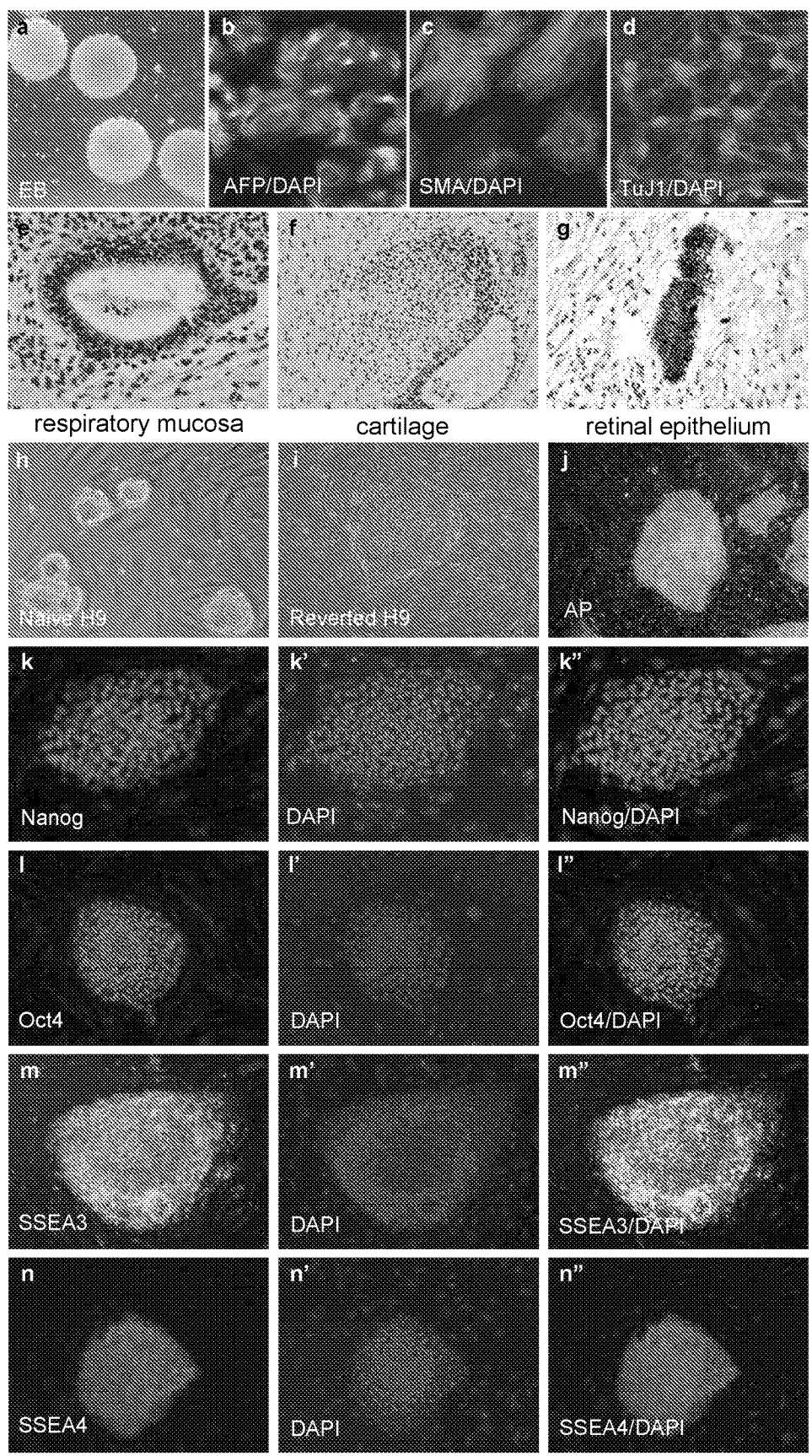
Figure 11:
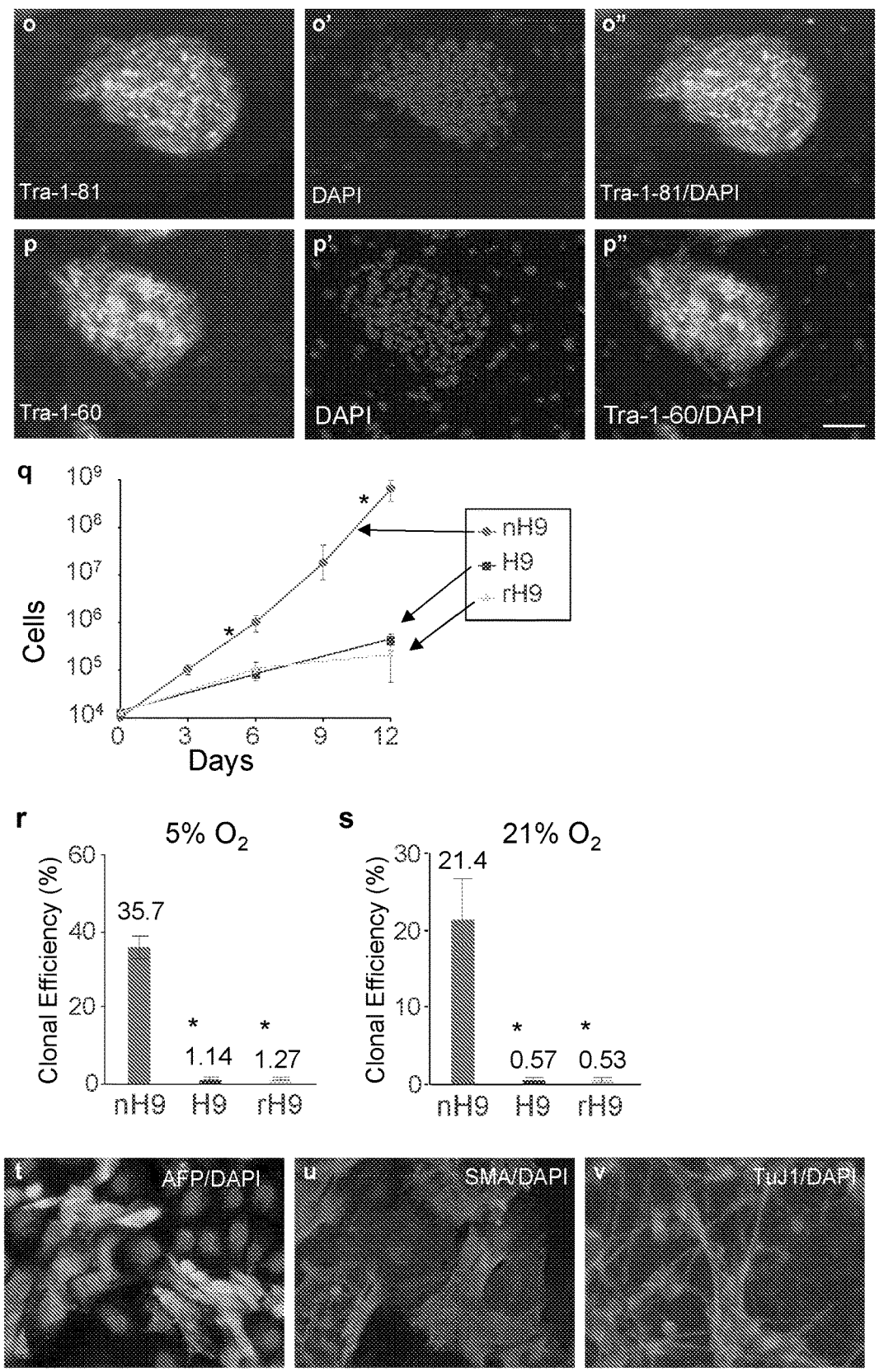

FIG. 11. Spontaneous differentiation, teratoma formation and reversion of naive H9. (a-d) Spontaneous differentiation of naive H9 in vitro through embryoid bodies (EB) (a) to cells positive for a-fetoprotein (AFP, endoderm) (b), smooth muscle actin (SMA, mesoderm) (c) and β3-tubulin (TuJ1, ectoderm) (d). (e-g) Naive H9 grafted in kidney capsules of SCID mice produced teratomas with endoderm (e), mesoderm (f) and ectoderm (g) tissues. (h-p'') Naive H9 (h) was reverted to primed H9 (rH9) (i), which was stained for pluripotency markers AP (j), Nanog (k-k''), Oct4 (l-l''), SSEA3 (m-m''), SSEA4 (n-n''), Tra-1-81 (o-o''), Tra-1-60 (p-p''). Bar, 100 mm. (q) Growth curve of naive H9 (nH9), H9 and reverted H9 (rH9). *, p<0.05, n=3, nH9 vs. H9 or rH9. (r-s) Clonal efficiency of naive H9 (nH9), H9 and reverted H9 (rH9) in 5% $O_2$ (r) and 21% $O_2$ (s). *, p<0.05, n=6, vs. nH9. (t-v) Spontaneous differentiation of reverted H9 to cells of all three germ layers.

Figure 12:
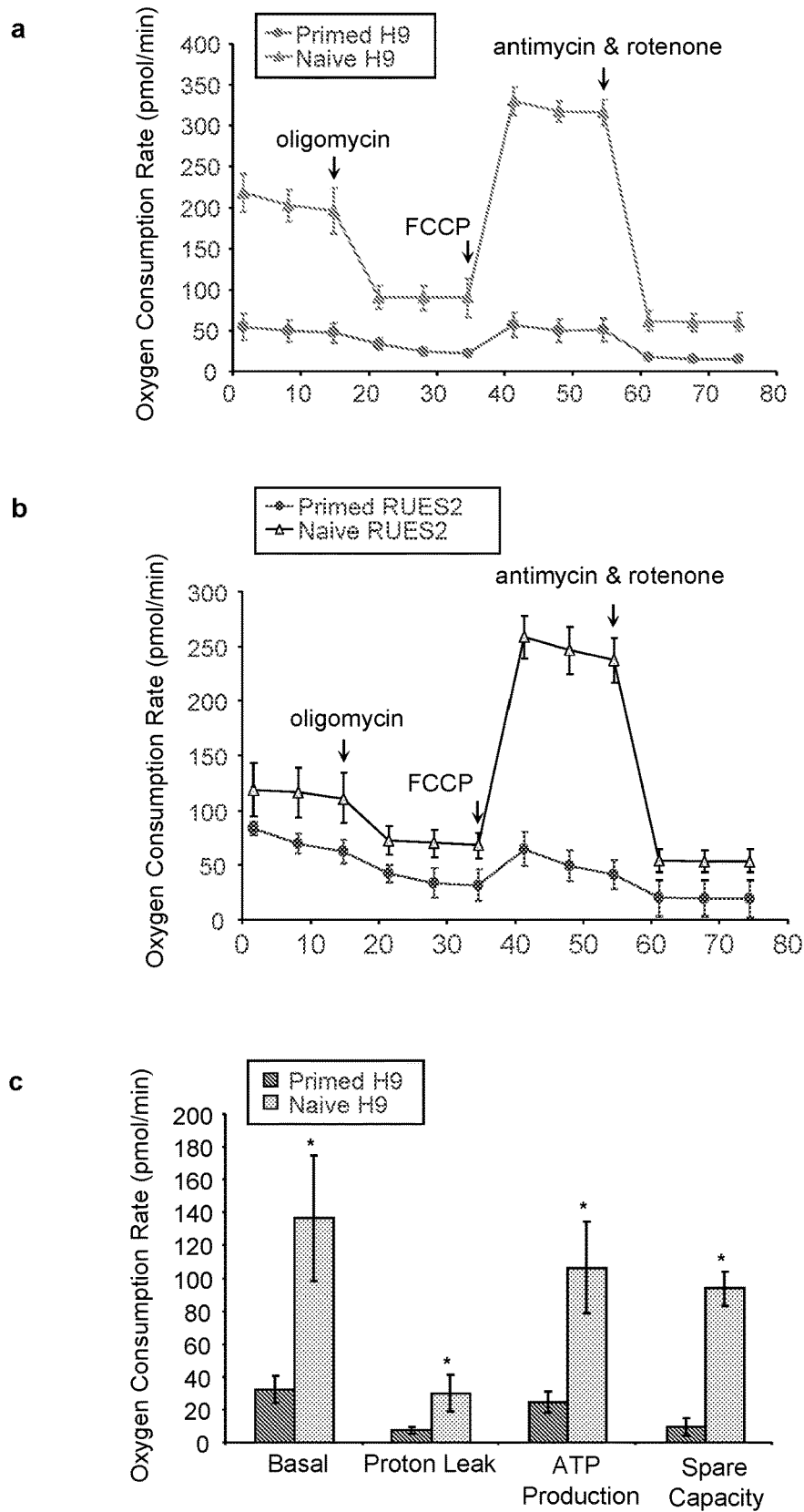
Figure 12:
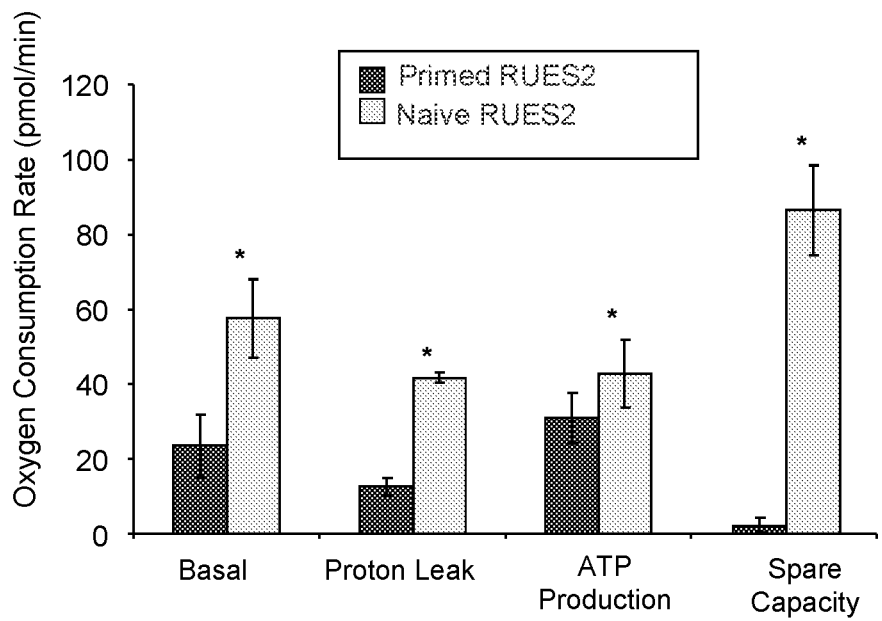
Figure 12:
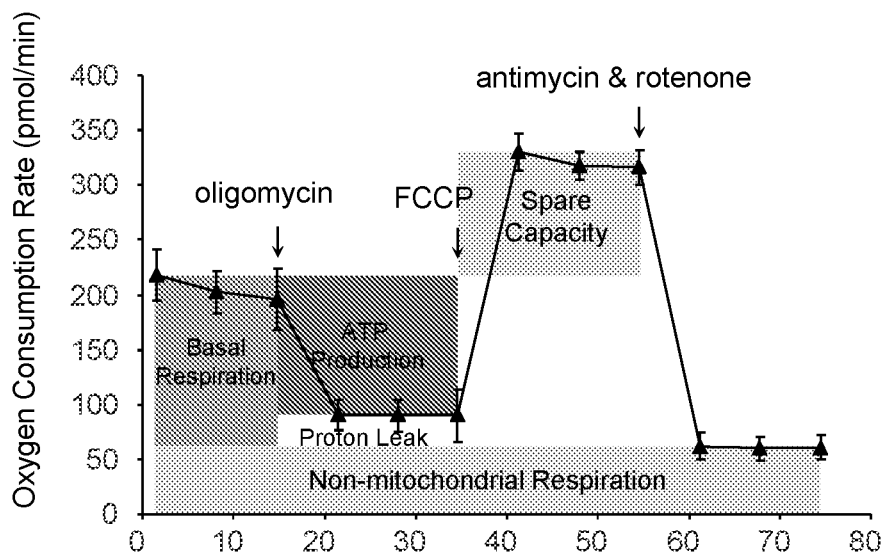

FIG. 12. Metabolic profiles of primed vs. naive hESCs. (a-b) Mitochondrial respiration in primed vs. naive H9 (a) or RUES2 (b) hESCs. (c-d) Key parameters of mitochondrial respiration in primed vs. naive H9 (c) or RUES2 (d) hESCs were quantified based on data in a-b, respectively. *, p<0.05, n=3, unpaired, two-tailed t-test, vs. primed state. (e) Graphic illustration of how various parameters are calculated.

Figure 13:
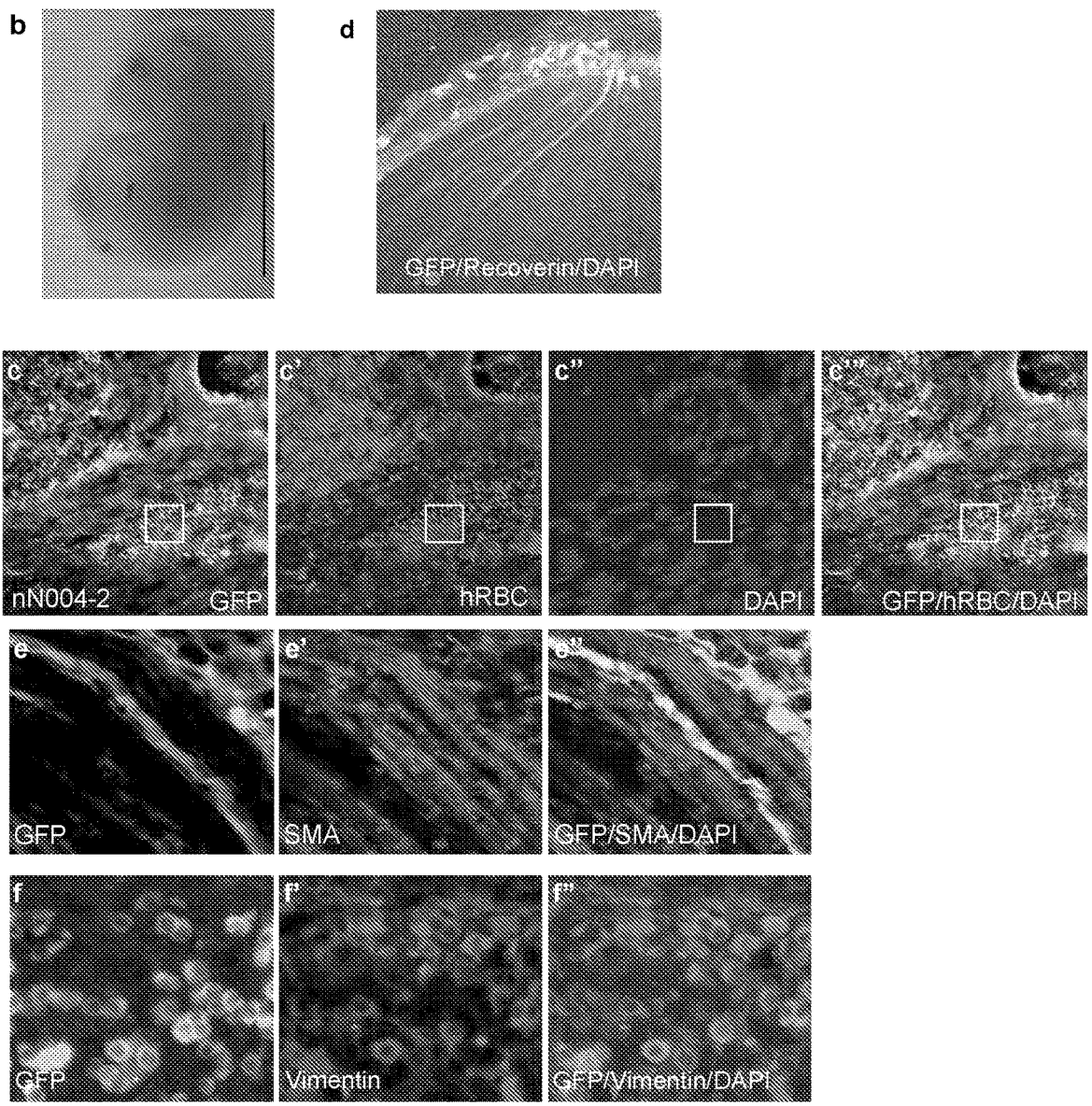
Figure 13:
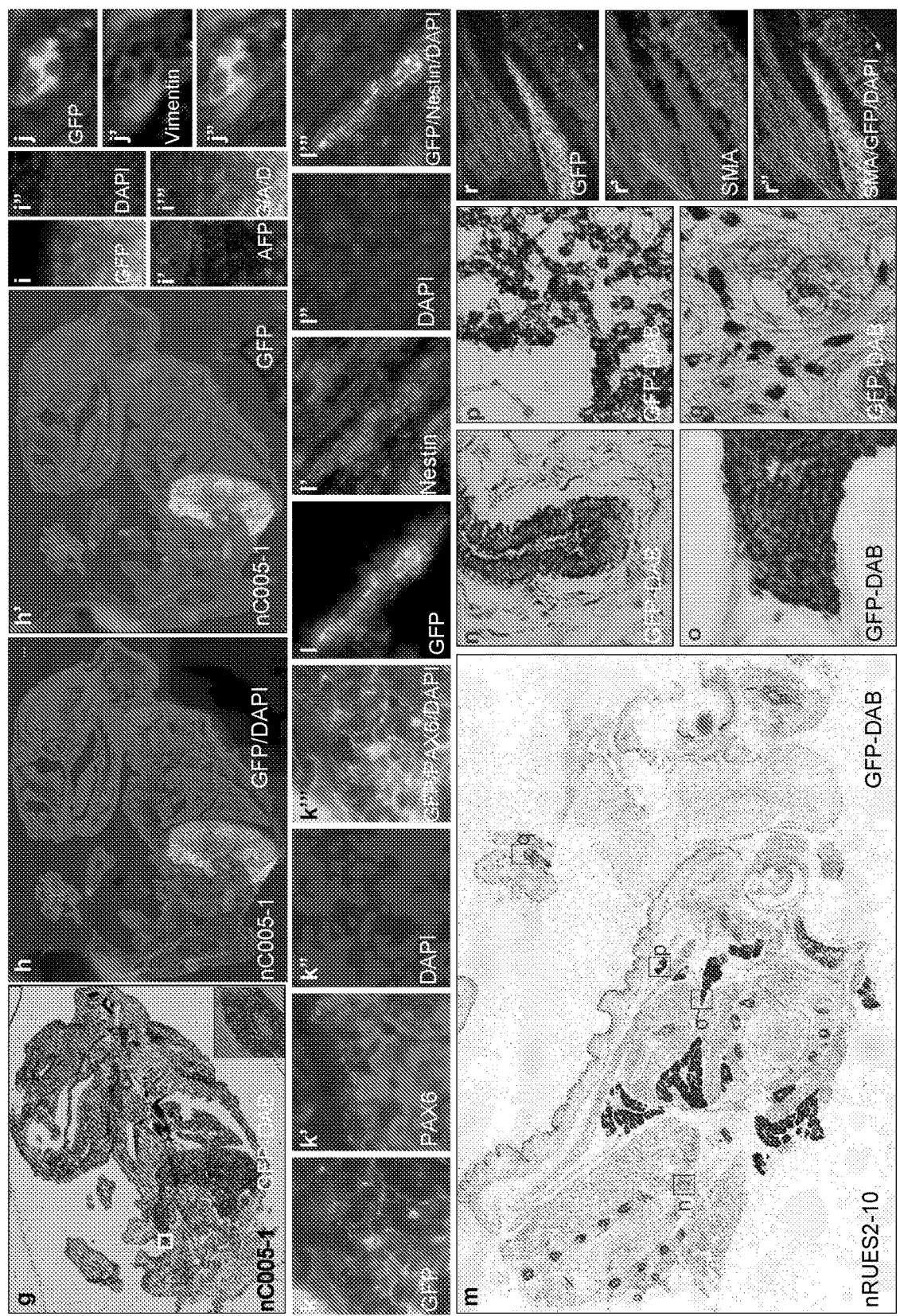

FIG. 13. Incorporation of naive hPSC-derived human cells in mouse embryos. (a) Details on injection of naive hPSCs to mouse blastocysts and analyses of mouse embryos. (b) Apparently normal gross morphology of mouse embryos at 17.5 days of gestation. Bar, 1 cm. (c-f″) A mouse embryo (nN004-2) derived from blastocysts injected with GFP-labeled naive N004 iPSCs was immunostained as indicated. White box in c-c″ was enlarged in FIG. 5m-m″. d, Enlarged image of boxed area in FIG. 5p″. (g-l″) DAB staining with GFP antibody (g), GFP fluorescence (h-h') and immunostaining (i-l″) of a mouse embryo (nC005-1) derived from blastocysts injected with naive C005 iPSCs that were labeled with lentivirus expressing GFP under EF1a promoter. (m-r″) A mouse embryo (nRUES2-10) derived from blastocysts injected with GFP-labeled naive RUES2 hESC was DAB-stained with anti-GFP (m-q) or immunostained as indicated (r-r″). Boxed areas in m were enlarged in n-q, respectively.

Figure 14:
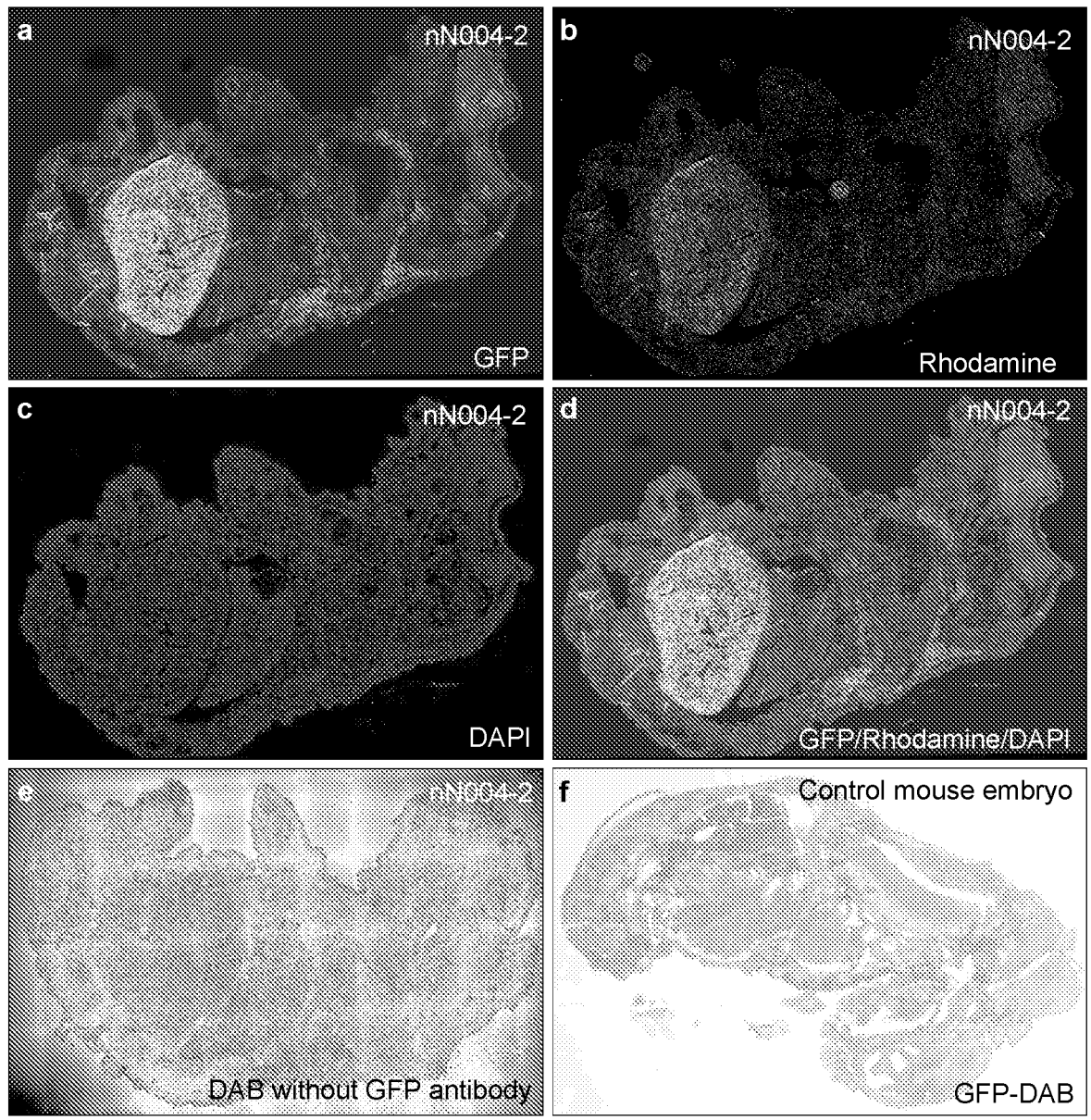

FIG. 14. Specificity of GFP fluorescence and GFP-DAB staining. (a-d) A sagittal section of a mouse embryo (nN004-2) derived from blastocysts injected with GFP-labeled naive N004 iPSCs was imaged on a fluorescence microscope. Fluorescence from GFP (a), rhodamine (b) and DAPI (c) channels was merged in (d). The lack of significant signal in rhodamine channel (b) and the high signal/noise ratio for GFP (a) showed that GFP fluorescence was specific, not from autofluorescence. (e) Another section from N004-2 embryo was DAB-stained without primary GFP antibody and only with secondary antibody. (f) A control mouse embryo with no human cell was DAB-stained with anti-GFP. Both (e) and (f) demonstrate the lack of specific GFP signal and thus the specificity of GFP-DAB staining in FIG. 13.

Figure 15:
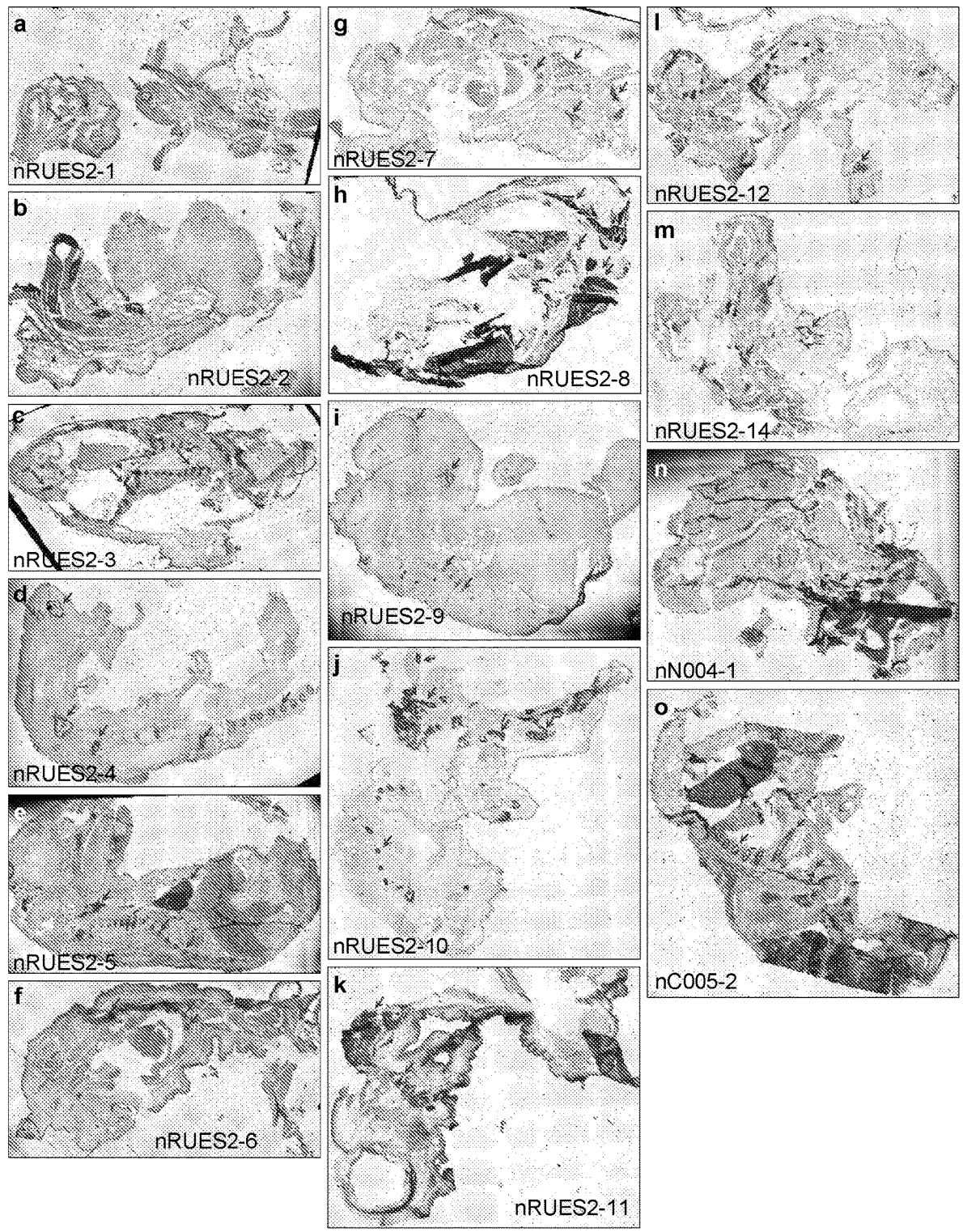

FIG. 15. Additional mouse embryos with GFP+ human cells. (a-o) Sections from additional mouse embryos were DAB-stained with anti-GFP to identify human cells. Many embryos were previously cut in half for extraction of DNA and were thus distorted in frozen sections. Arrows highlight some of the GFP+ human cells.

Figure 16:
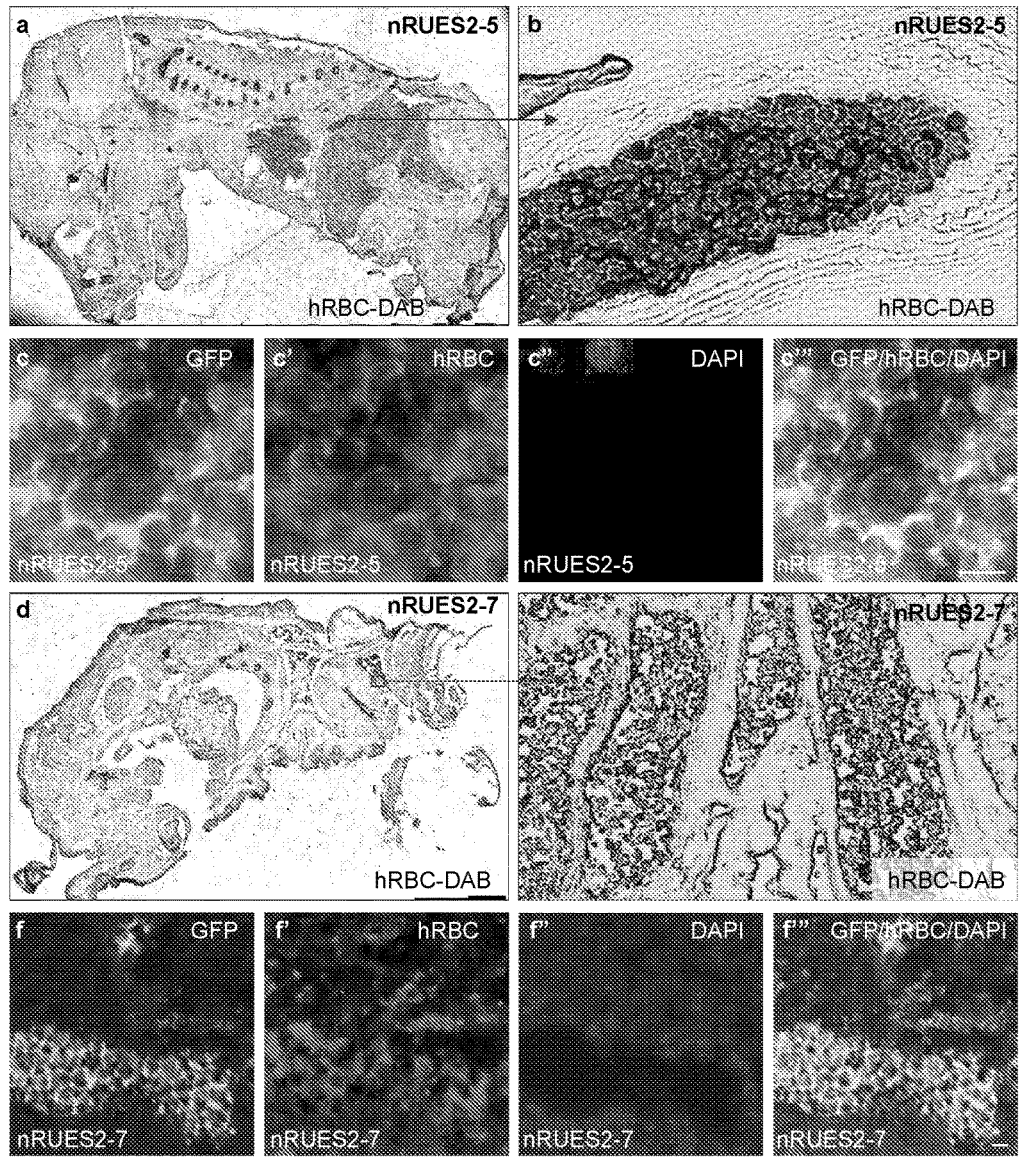

FIG. 16. hRBC staining of additional embryos. (a-c″) Sections from nRUES2-5 mouse embryo were DAB-stained with an antibody against human Red Blood Cells (hRBC) (a, with boxed area enlarged in b), or costained for GFP (c), hRBC (c'), DAPI (c″) for the merged image (c″). (d-f″) Sections from nRUES2-7 mouse embryo were DAB-stained with anti-hRBC (d, with boxed area enlarged in e), or costained for GFP (f), hRBC (f'), DAPI (f″) for the merged image (f″). Bars, 10 μm.

Figure 17:
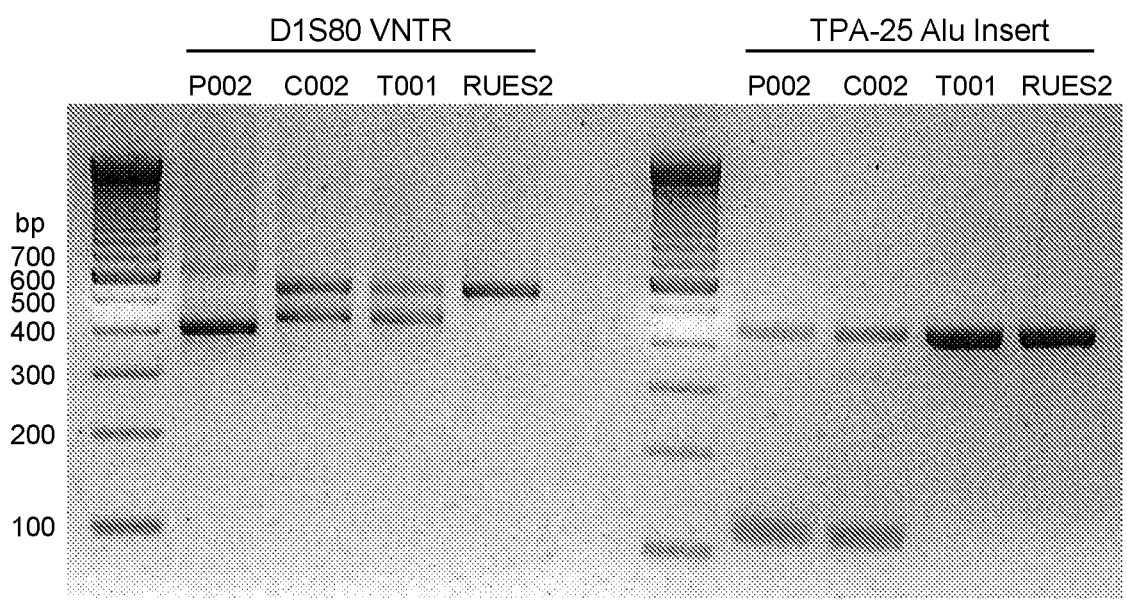

FIG. 17. Specificity of DNA fingerprinting. DNA fingerprinting was performed on genomic DNA isolated from iPSCs of three different individual and RUES2, using the indicated primer sets. Each individual had a unique combination of PCR bands.

Figure 18:
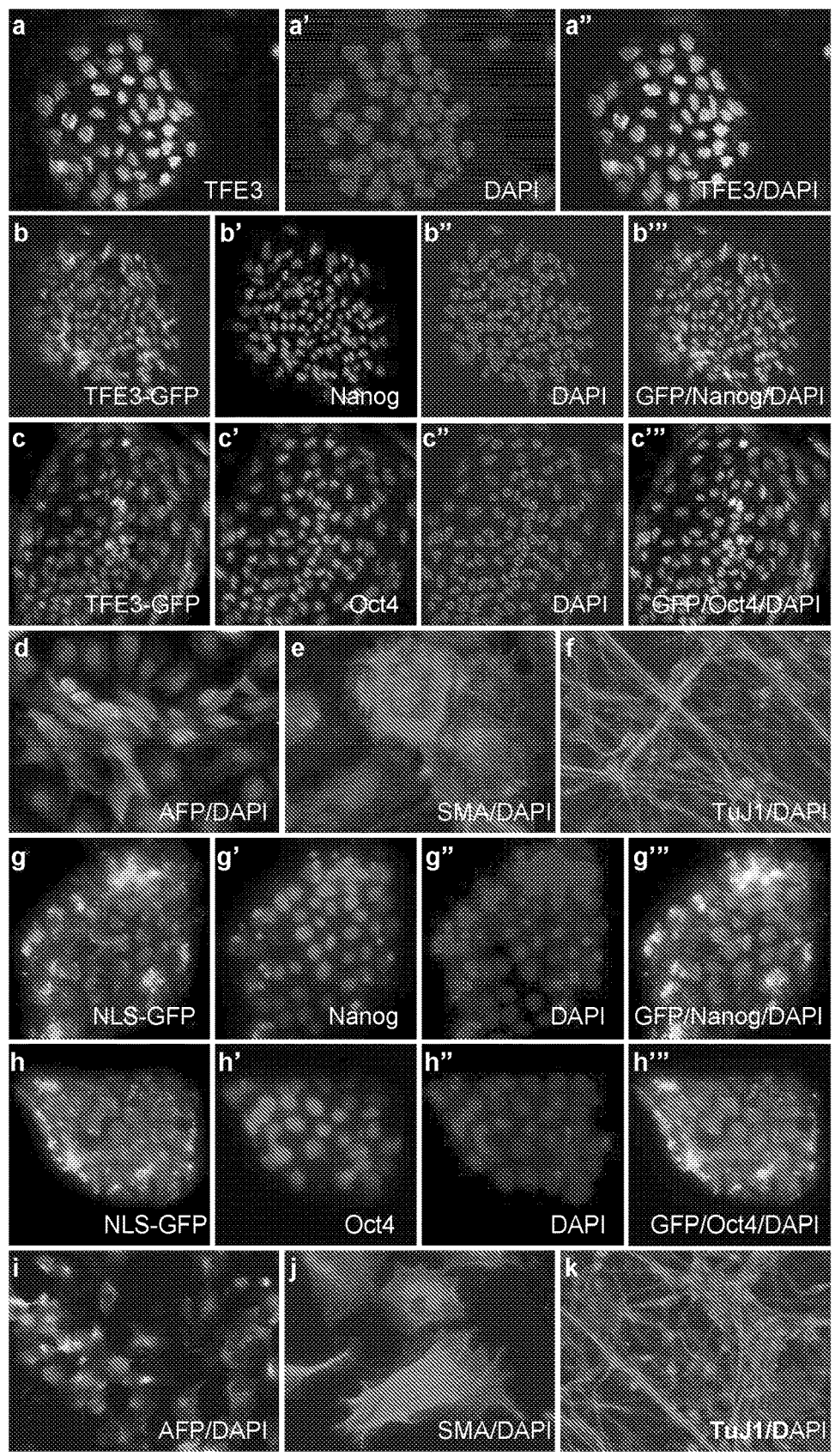

FIG. 18. Properties of TFE3. (a-a″) Immunostaining of naive H9 for TFE3 (a) and DAPI (a'). Merged image (a″) showed nuclear localization of TFE3 in naive hPSC. (b-f) Primed H9 hESCs stably expressing TFE3-GFP were costained as indicated to show that the expression of pluripotency markers was unaffected (b-c″). These cells were differentiated spontaneously to cells of all three germ layers (d-f). (g-k) Primed H9 hESCs stably expressing TFE3 with mutated Nuclear Localization Signal (NLS-GFP) were costained as indicated to show that the expression of pluripotency markers was unaffected (g-h″). These cells were differentiated spontaneously to cells of all three germ layers (i-k).

Figure 19:
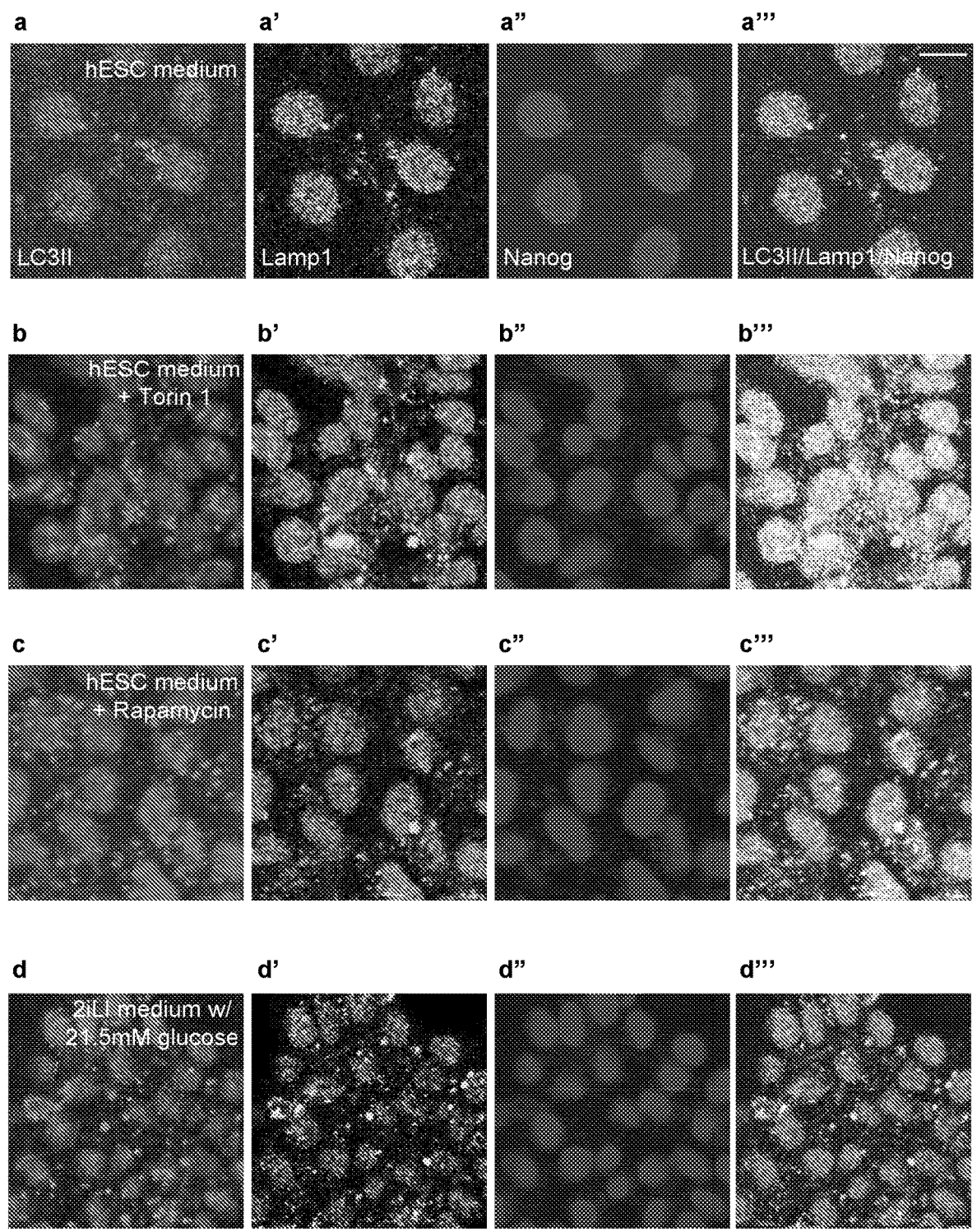
Figure 19:
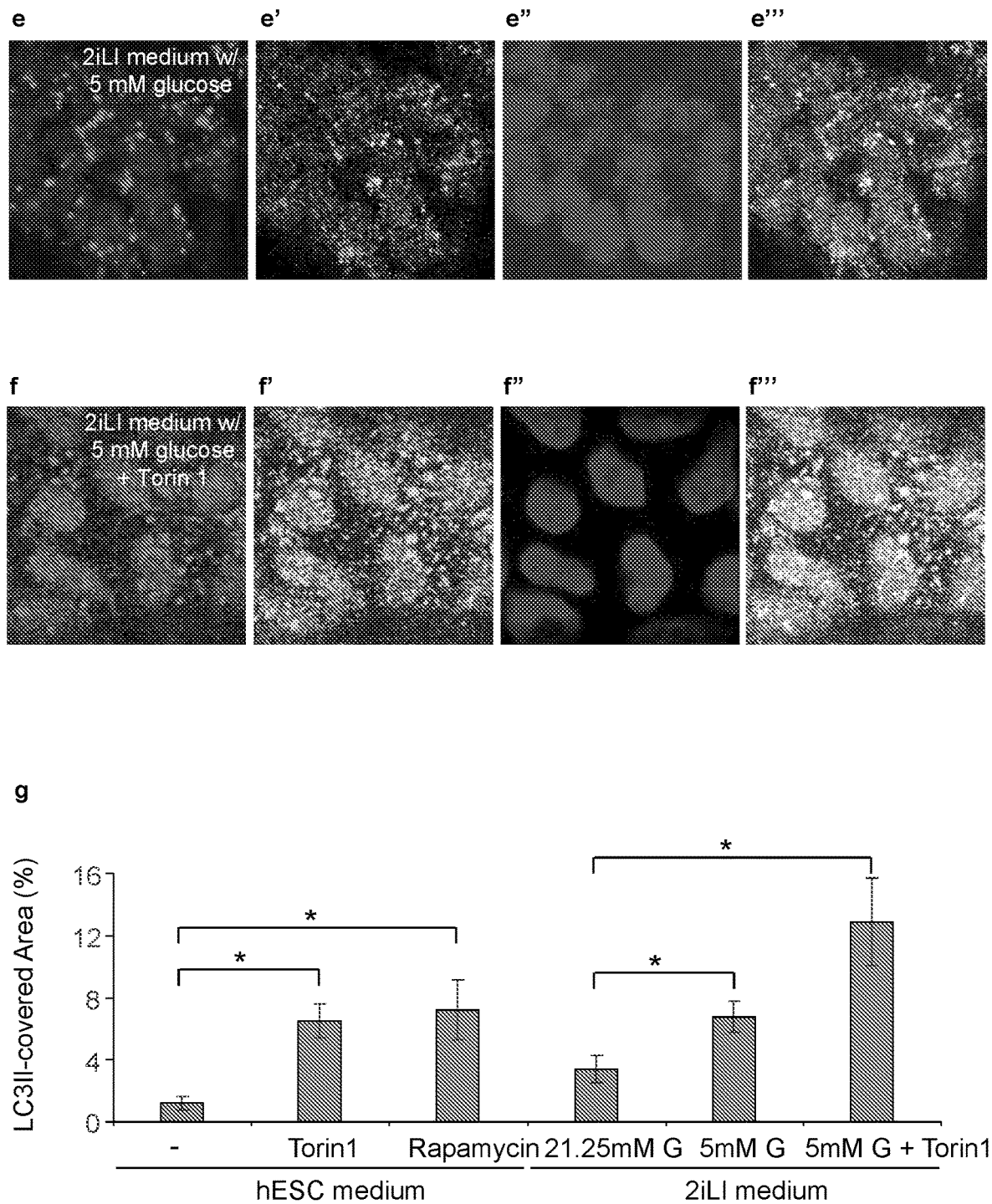

FIG. 19. Conversion conditions trigger autophagy in hPSCs. (a-f″) Primed H9 hESCs were treated for 3 hours in hESC medium (a-a″), hESC medium with 10 mM Torin1 (b-b″), hESC medium with 10 mM Rapamycin (c-c″), 2iLI medium with 21.5 mM glucose (d-d″), 2iLI medium with 5 mM glucose (e-e″), or 2iLI medium with 5 mM glucose and 10 mM Torin1 (f-f″). Cells were fixed and stained for the autophagy marker LC3II (a-f), the lysosome marker Lamp1 (a'-f'), and the pluripotency marker Nanog (a″-f″). Merged images are shown in a‴-f‴. bar, 10 mm. (g) The percentage of cell area covered by LC3II puncta was quantified. *, $p<0.05$, n=8 to 10 cells for each conditions, unpaired, two-tailed t-test.

Figure 20:
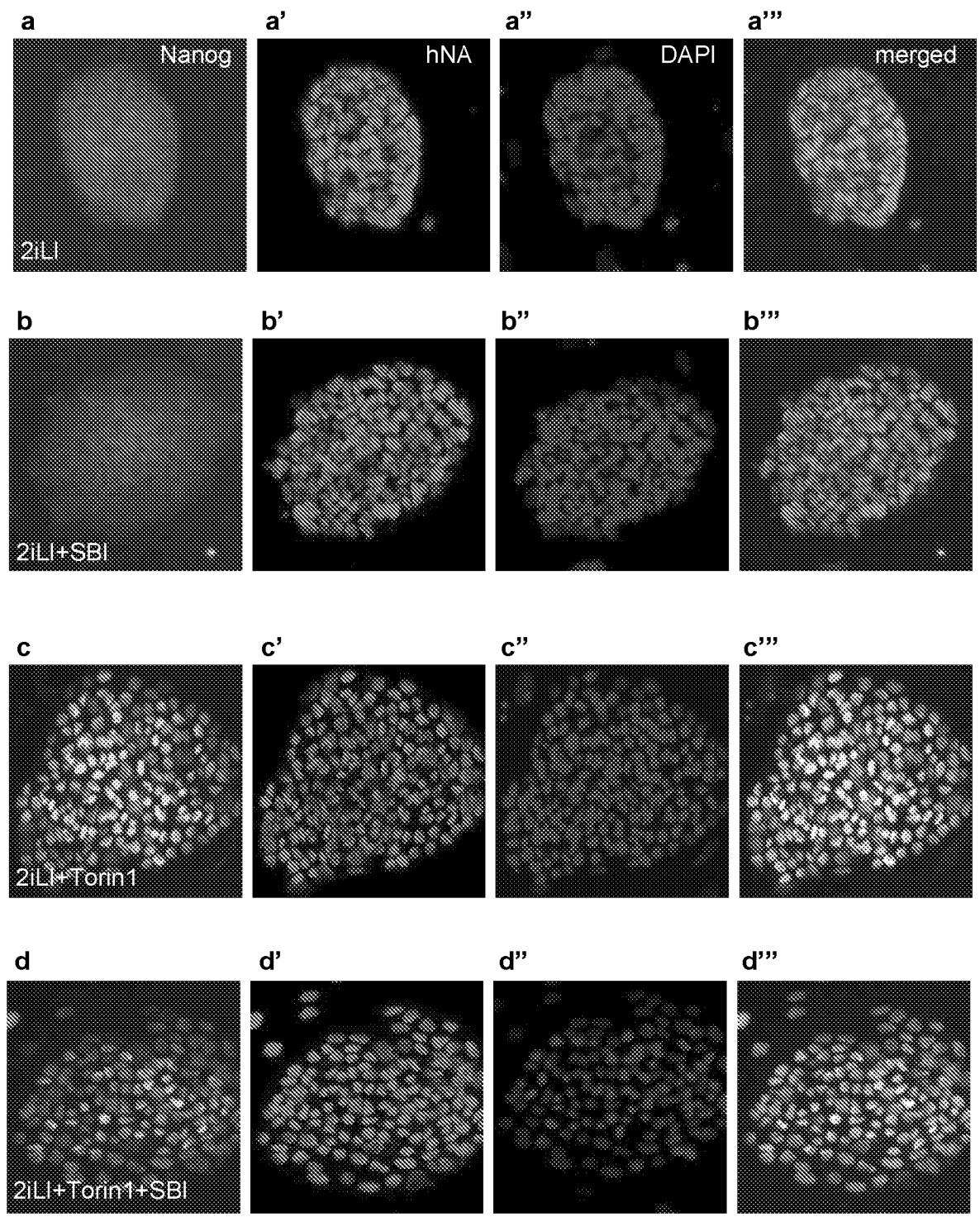
Figure 20:
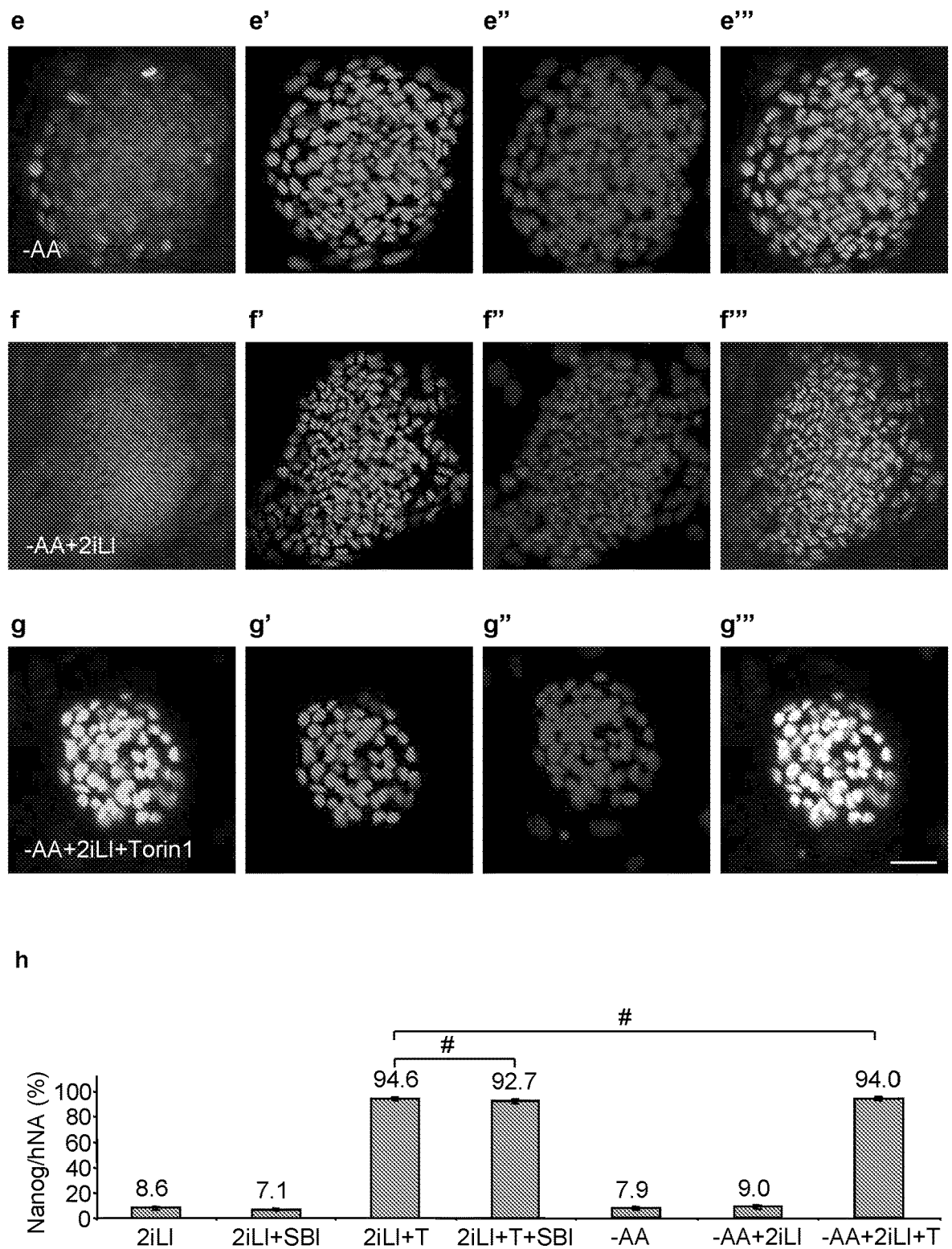

FIG. 20. Conversion is unaffected by manipulations of autophagy. (a-g‴) Primed H9 hESCs were treated for 3 hr in 2iLI (a-a‴), 2iLI plus the Ulk1 inhibitor SBI-0206965 (SBI) to block autophagy (b-b‴), 2iLI and Torin1 (c-c‴), 2iLI and Torin1 plus SBI (d-d‴), amino acids withdrawal (−AA) in HBSS to induce autophagy (e-e‴), amino acid withdrawal in HBSS plus 2iLI (f-f‴), amino acid withdrawal in HBSS plus 2iLI and Torin1 (g-g‴). The cells were dissociated and plated on MEF in 2iLI media for five days, before they were fixed and stained for Nanog (a-g), hNA (a'-g'), and DAPI (a″-g″), for merged images (a‴-g‴). Bar, 50 mm. (h) The percentage of human cells (hNA+) that were Nanog+ was quantified for each condition. #, $p>0.05$, n=6 from 3 independent experiments, each with 2 wells, unpaired, two-tailed t-test.

Figure 21:
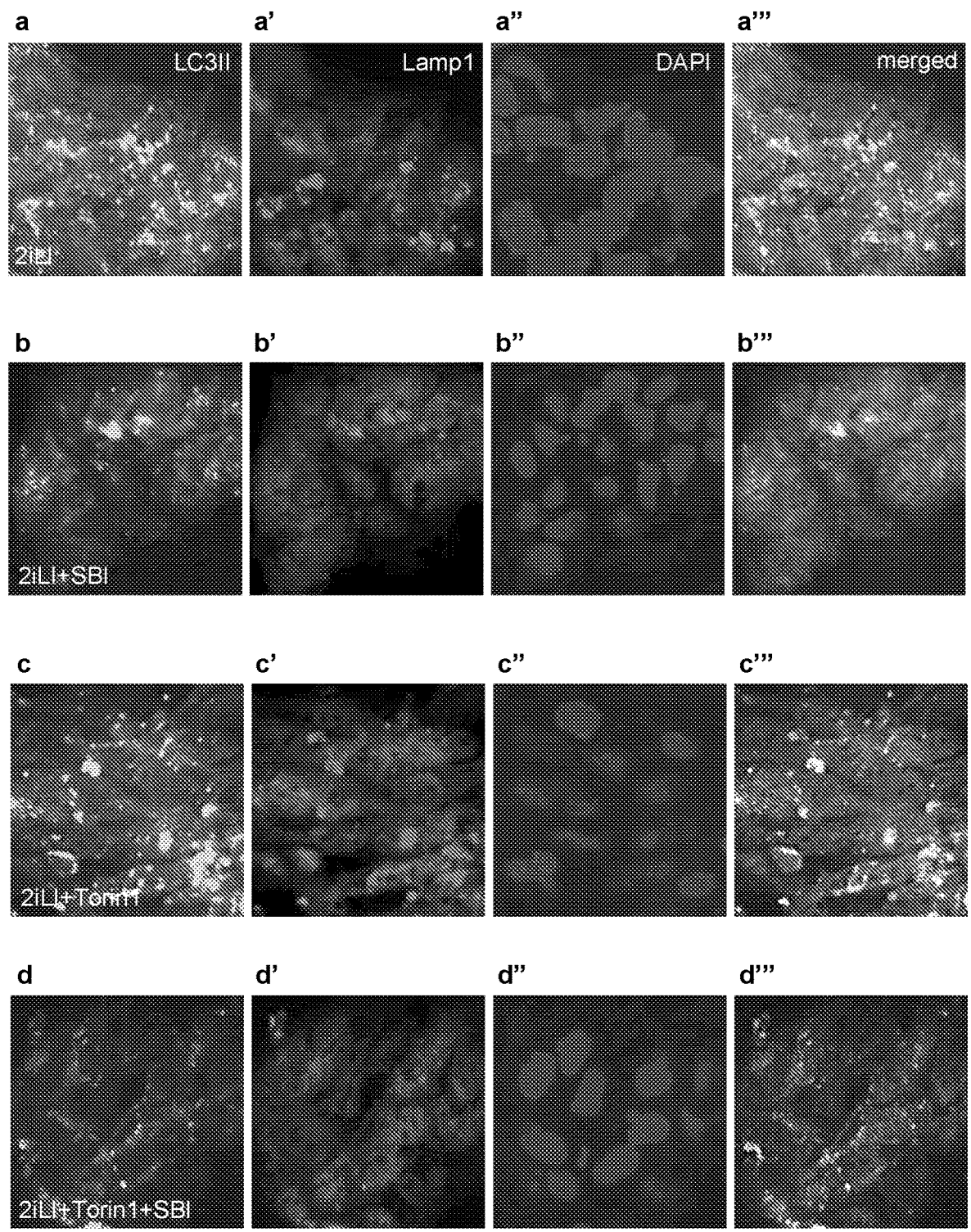
Figure 21:
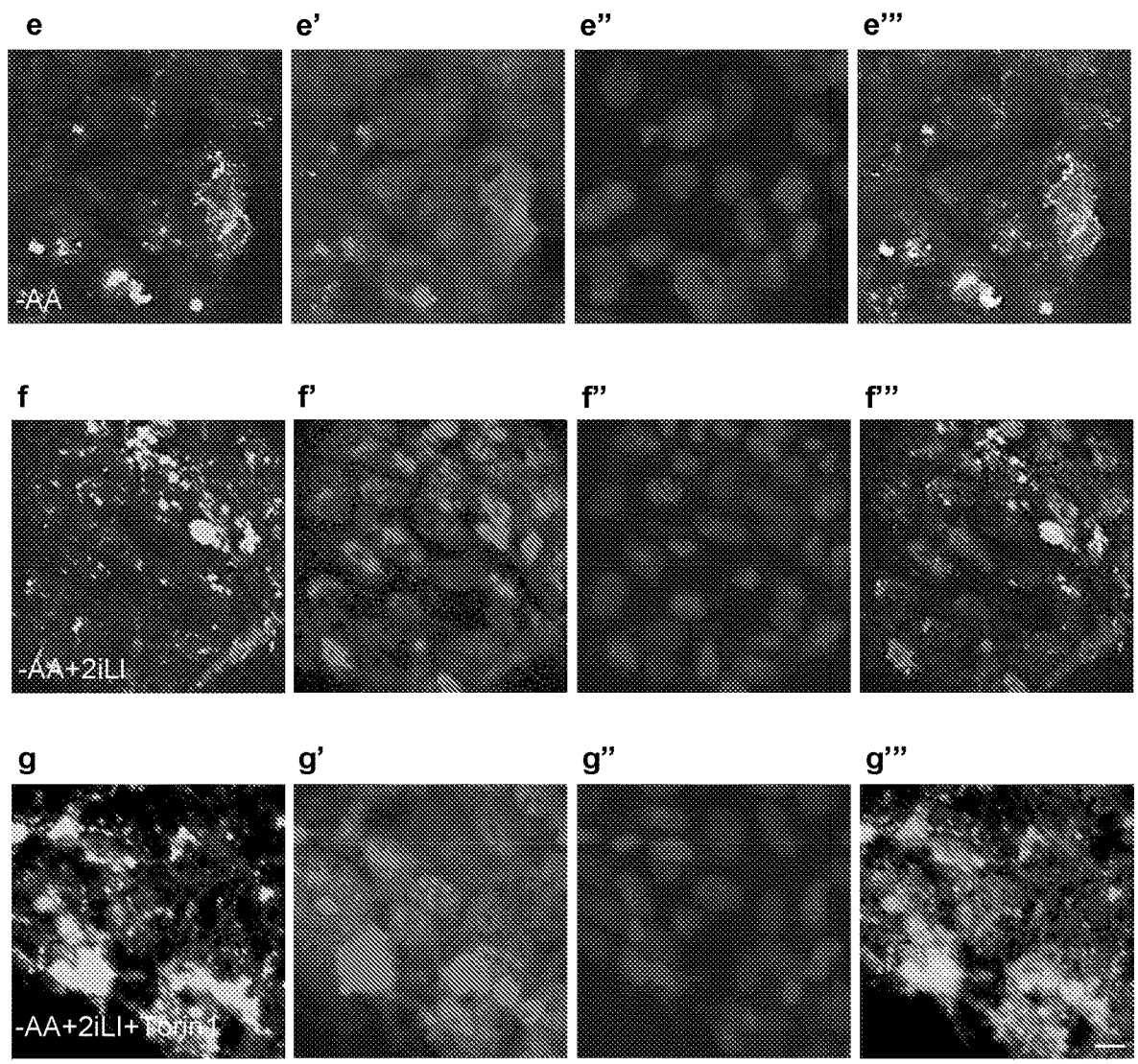
Figure 21:
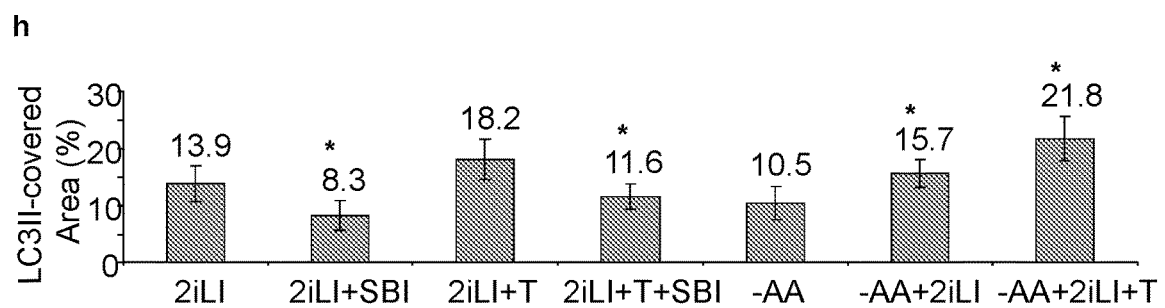

FIG. 21. Levels of autophagy induced by treatments in Supplementary FIG. 13. (a-g‴) Primed H9 hESCs were treated for 3 hr in 2iLI (a-a‴), 2iLI plus the Ulk1 inhibitor SBI-0206965 (SBI) to block autophagy (b-b‴), 2iLI and Torin1 (c-c‴), 2iLI and Torin1 plus SBI (d-d‴), amino acids withdrawal (−AA) in HBSS to induce autophagy (e-e‴), amino acid withdrawal in HBSS plus 2iLI (f-f‴), amino acid withdrawal in HBSS plus 2iLI and Torin1 (g-g‴). Cells were fixed and stained for LC3II (a-g), Lamp1 (a'-g'), and DAPI (a″-g″). Merged images are shown in a‴-g‴. bar, 10 mm. (h) The percentage of cell area covered by LC3II puncta was quantified. *, vs. the preceding bar, $p<0.05$, n=8 to 10 cells for each conditions, unpaired, two-tailed t-test.

DETAILED DESCRIPTION OF THE DISCLOSURE

The present disclosure provides compositions and methods for making naive human pluripotent stem cells in vitro. The disclosure is based on the present observations that transient treatment with a selective inhibitor of mTor, can convert hPSCs from primed to naive pluripotency. Naive pluripotency reflects the pluripotent state of the inner cell mass of the blastocysts. Using mouse as an example, when cells in the inner cell mass or their equivalent in vitro counterparts, such as mouse embryonic stem cells, are transferred to a mouse blastocyst, they can contribute to cells of all three germ layers and thus form chimeric mouse embryos. In contrast, primed pluripotency reflects the pluripotent state of post-implantation epiblasts. When primed pluripotent stem cells are injected into a mouse blastocyst, they are unable to generate chimera. A more detailed discussion on primed and naive pluripotency can be found in De Los et al., Nature 525, 469-478 (2015), incorporated herein by reference. By the method of the present disclosure, naive hPSCs can be generated which can be transferred to a non-animal blastocyst (such as a mouse blastocyst) and they have the ability to contribute to the formation of human cells (of all three germ layers) in the non-human animal.

The naive hPSCs then can be maintained in vitro in the same or similar conditions as typically used for mouse embryonic stem cells (ESCs). The naive hPSCs generated by the present method can be maintained in a culture medium comprising two inhibitors (MEK inhibitor and GSK3β inhibitor), LIF and insulin. The culture or incubation medium is termed herein as 2iLI (2 inhibitors [MEK inhibitor and GSK3β inhibitor], LIF and Insulin). MEK is mitogen-activated protein kinase kinase, also called MAPK kinase. GSK is Glycogen Synthase Kinase. The terms GSK3β inhibitor and GSK3 inhibitor refer to the same inhibitor and the terms are used interchangeably in this disclosure. The naive hPSCs of the present disclosure exhibited high clonal efficiency, rapid cell proliferation, active mitochondrial respiration, X chromosome activation, DNA hypomethylation, and transcriptomes more similar to those of human blastocysts than primed hESCs. It is considered that one or more of these improved characteristics enable naive hPSCs to generate chimera when they are transferred to mouse blastocysts. In contrast to the hPSCs generated by methods described previously, the present naive hPSCs can significantly contribute to mouse embryos by generating a large amount of mature human cells of many different kinds, when the naive hPSCs are transferred to mouse blastocysts. Further, in contrast to previous hPSCs, the present hPSCs do not need to be maintained in various chemical inhibitors or forced expression of transgenes. In one embodiment, the only inhibitors used to produce the naive hPSCs and maintain them in culture are a MEK inhibitor, a GSK3 inhibitor and LIF. In one embodiment, the only inhibitors used to produce the naive hPSCs are one or more MEK inhibitors, one or more GSK3 inhibitors and LIF. The generation of naive hPSCs and the maintenance of the generated naive hPSCs can be carried out under serum-free conditions. Thus, no serum is added to the culture medium.

As used in this disclosure including the claims, the singular forms "a", "an", and "the" include plural references unless the context clearly dictates otherwise. Thus, for example, references to "the method" includes one or more methods, and/or steps of the type described herein, which will be apparent to those persons skilled in the art having the benefit of this disclosure.

The term "pluripotent stem cell" (also referred to as "PSC") herein used refers to a cell having an ability to differentiate into any type of cell of an adult (pluripotency) and also having self-renewal capacity which is an ability to maintain the pluripotency during cell division. The "PSCs" include Embryonic Stem Cells (ESCs), which are derived from inner cell mass of blastocysts, and induced PSCs, which are cells converted from somatic cells by a variety of methods, such as a transient overexpression of a set of transcription factors. The PSCs may be a cell of any species with no limitation, and preferably a mammalian cell. It may be a rodent or primate cell. For example, it may be a monkey, mouse or a human pluripotent stem cell.

In one aspect, the present disclosure provides a process of making naive human pluripotent stem cells comprising incubating human primed PSCs or iPSCs with an mTor inhibitor, for a sufficient, but limited period of time to generate naive pluripotent cells in culture. In this disclosure, PSCs are termed as "primed" is they have not been exposed to Torin 1 as described herein. In one embodiment, the present disclosure provides a process of making naive human pluripotent stem cells comprising incubating primed PSCs or iPSCs with an agent that induces the nuclear translation of TFE3, such as an mTor inhibitor, in culture. In one embodiment, the present disclosure provides a process of making naive human pluripotent stem cells comprising incubating primed or iPSCs with an mTor inhibitor to form a culture. The mTor inhibitor may be an inhibitor of mTORC1 or mTORC2 or both.

The mTor inhibitor can be Torin1 (available, e.g. from Tocris). Its chemical formula is $C_{35}H_{28}F_3N_5O_2$ (CAS no. 1222998-36-8). In one embodiment, the Torin1 is present in an amount of 1-20 µM and the incubation is performed for a time period of about 1 to about 24 hours, including all integers and ranges in between. In a preferred embodiment, the time period is about 3 hours. The concentration of Torin 1 can be 1, 2, 3, 4, 5, 6, 7, 8, 9, 10, 11, 12, 13, 14, 15, 16, 17, 18, 19 or 20 µM. In various embodiments, the time period can be 2 to 20 hours, a to 20 hours, 2 to 10 hours, 1 to 10 hours, 2 to 5 hours, and 2-4 hours and the like and all times from 1 to 24 hours. In one embodiment, the mTor inhibitor exposure is for 3 hours.

The mTor inhibitor can be rapamycin (available, e.g., from Sigma Aldrich). In one embodiment, the rapamycin is present in an amount of 1-20 µM and the incubation is performed for a time period of about 1 to about 24 hours, including all integers and ranges in between.

The mTor inhibitor can be temsirolimus (CCI-779), everolimus (RAD001), deferolimus (AP-23573), ridaforolimus (AP-23573), dactolisib, BGT226, SF1126, PKI-587, sapanisertib (INK128), AZD8055, and AZD2014, AZD3147, Compound 401, KU 0063794, PF 05212384, or PP242.

The incubation medium can have one or more mTor inhibitors described here or combinations of any other mTor inhibitors.

The present method comprises deriving primed PSCs or iPSCs and then generating naive pluripotent stem cells from the primed PSCs or the iPSCs.

The PSC or iPSC is a mammalian PSC or mammalian iPSC. In one embodiment, the PSC or iPSC is a human PSC or human iPSC. In another embodiment, the PSC or iPSC is porcine PSC or porcine iPSC. In a further embodiment, the PSC or iPSC is monkey PSC or monkey iPSC.

The iPSCs can be generated from any adult cell. For example, suitable cells include, but are not limited to, keratinocytes, dermal fibroblasts, leukocytes derived from peripheral blood, and cells obtained in urine. The iPSCs are generated by methods known in the art. For example, iPSCs can be generated by reprogramming adult cells using lentivirus or plasmids.

Any human somatic cells (e.g. skin fibroblasts or cells flushed out in urine) can be reprogrammed to iPSC using lentivirus (Maherali et al. *Cell Stem Cell* 3, 340-345 (2008)) or plasmids (Okita et al. *Nat. Methods* 8, 409-412 (2011)). For example, human dermal fibroblasts (such as $1 \times 10^5$) can be infected for a suitable period of time (such as 16 hr) with lentiviruses to express the following: hOct4, hSox4, hKlf4 and hNanog each at MOI 15, c-Myc at MOI 6, and M2rtTA at MOI 30 in the presence of 4 µg/ml polybrene. Infected cells can be plated on feeder cells in culture medium containing a suitable amount of serum, L-Glutamine, antibiotics (such as penicillin and streptomycin). After incubation (such as overnight), media can be changed to hESC media and the transgenes can be induced by the addition of doxycycline. After initial appearance and death of transformed cells, clones with hESC morphology generally appear between day 24 and 40 days. They can be picked and expanded under hESC culture condition. These iPSCs can be converted to naive state using the methods and compositions of the present disclosure.

The iPSCs or primed PSCs can be derived from the patient who is the intended recipient of the generated cells, tissue or organ, or can be derived from an individual that is matched with the patient with respect to histocompatibility considerations.

For the conversion of the iPSCs to naive state, the cells are incubated in 2iLI medium containing one or more mTor inhibitors. In one embodiment, the cells are incubated in a culture medium containing an MEK inhibitor, a GSK3β inhibitor, LIF (leukemia inhibitory factor) and insulin. In one embodiment, the MEK inhibitor is PD0325091 (e.g., PD, available from EMD Millipore). In an embodiment, the GSK3β inhibitor is CHIR99021 (available, e.g., from Stemgent). In a preferred embodiment, the insulin is human insulin.

In a preferred embodiment, the LIF is human LIF. In one embodiment, the human LIF is recombinant human LIF. In a preferred embodiment, the LIF is present at a concentration of about 4 to 40 ng/ml, and all values therebetween and all ranges between 4 and 40 ng/ml.

In an embodiment, the insulin is present in an amount from about 1 μg/ml to about 100 μg/ml. It can be 5 μg/ml to about 100 μg/ml, including all integers and ranges in between. In one embodiment, the insulin is present in an amount of about 1-50 μg/ml. For example, insulin can be from 10 to 25 ng/ml. In one example it is about 18 μg/ml. B27 and N2 supplements, which contain undisclosed amount of insulin, can be used, however, that introduces unknown components that are not needed and may be deleterious. Therefore, it is preferable to not use B27 or N2 or other similar supplements.

The components in the 2iLI medium are preferably isolated and purified. The components of the 2iLI media can be made from chemicals or recombinant proteins.

In one embodiment, the present disclosure provides a cell culture medium comprising or consists essentially of Torin 1, an MEK inhibitor, a GSK3β inhibitor, LIF, and insulin. The base medium for the present cell culture medium is any standard culture medium such as Dulbecco's Modified Eagle's Medium (DMEM). In one embodiment, the medium comprises or consists essentially of Torin 1, an MEK inhibitor, a GSK3β inhibitor, LIF, and insulin, and does not contain supplements such as N2, B27 or other similar supplements. In one embodiment, the only inhibitors in the medium are an MEK inhibitor, a GSK3β inhibitor, and LIF. In one embodiment, the cell culture medium is a DMEM based medium comprising or consisting essentially of MEK inhibitor is PD0325091, GSK3β inhibitor is CHIR99021, LIF, insulin, Torin 1 and does not contain any supplements such as N2 or B27 or any other defined or undefined supplements. The amount of glucose in the DMEM may be similar to physiological levels, which is generally termed as low glucose for culture media purposes.

Instead of DMEM, other culture media can also be used. Alternatives of additions include F12, Neural Basal Medium and the like. For example, in one embodiment, the medium can be a combination of glucose-free DMEM/F12 and glucose-free Neural Basal Medium. Glucose can be added to the media to provide 5 mM glucose (i.e, at physiological levels). The media are available commercially (such as from Life Technologies).

In an embodiment, the present 2iLI media does not contain at least one of N2 supplement or B27 supplement. In another embodiment, the 2iLI media does not contain N2 supplement and does not contain B27 supplement. In another preferred embodiment, the 2iLI media comprises about 5 mM glucose.

The cells can be cultured under an environment comprising 4-6% $O_2$. For example, the cells can be cultured under about 5% $O_2$. It was observed that the reduced level of $O_2$ (more closely approximating the physiological levels that cells are exposed to) was better for generating the naive PSCs than the usual about 21% $O_2$.

In one aspect, the present disclosure provides a method for generating naive human pluripotent stem cells. A naive human pluripotent stem cell (hPSC) is characterized by the ability to significantly contribute to cells of all three germ layers when a naive hPSC is transferred to a mouse blastocyst. Naive hPSCs can be maintained in culture in the same media as typically mouse ESCs are maintained and exhibit similar properties to mouse ESCs in high clonal efficiency, rapid cell proliferation, active mitochondrial respiration, X chromosome activation, DNA hypomethylation, and transcriptomes.

The method of the present disclosure comprises generating human iPSCs, culturing human iPSCs on a feeder layer (such as mouse embryonic fibroblasts that have lost the ability to proliferate), exposing the human iPSCs to about 5% $O_2$ to a culture medium containing about 5% glucose, an MEK inhibitor, a GSK3β inhibitor, human LIF, human insulin and Torin 1 for a limited period of time (such as from 1 to 24 hours, preferably 3 to 5 hours), continuing to grow the cells in the medium of same composition, but lacking Torin 1, further continuing to grow the cells in the medium lacking Torin 1, and collecting the naive pluripotent stem cells after about 5-7 days. The presence of naive human pluripotent stem cells can be identified based on high clonal efficiency, rapid cell proliferation, active mitochondrial respiration, X chromosome activation, DNA hypomethylation, and transcriptomes more similar to those of human blastocysts than primed hESCs. More importantly, when naive human pluripotent stem cells are transferred to mouse blastocysts, they significantly contribute to cells of all three germ layers, robustly producing mouse-human chimeric embryos (also termed chimeras in this disclosure).

The naive pluripotent stem cells can be used for implanting into animal models for the purpose of growing human cells, tissues or organs. The naive pluripotent stem cells of the present disclosure are truly naive in the sense that they can lead to generation of cells of all three germ layers—endoderm, mesoderm and ectoderm. Prior to implantation, the naive pluripotent stem cells can be proliferated in culture. It was observed that these cells can be passaged up to at least 50 passages without losing their characteristic features such as high clonal efficiency, rapid cell proliferation, active mitochondrial respiration, X chromosome activation, DNA hypomethylation, and transcriptomes similar to those of human blastocysts than primed hESCs.

The cells can be used fresh after culture or can be frozen for later use. Culture media can be removed or reduced from the cells by repeated washings with an appropriate buffer.

The naive hPSCs can be implanted into host animals. For example, naive hPSCs cultured in 2iLI media can be dissociated to single cells (such as with trypsin (TrypLE)) for a few minutes (such as 5-6 minutes) and placed in suitable culture dishes (such as 10 cm dishes for 45 minutes) to remove feeder cells (MEF) cells through attachment. The supernatant, which contains the naive hPSCs, can be removed from the dish and centrifuged at low speed (such as for 10 min at 2000 rpm). Cells in the pellet can be resuspended in buffer (termed Mouse Blastocysts Injection Buffer (HEPES-buffered DMEM with 5% FBS)). A few cells (such as 10-12 naive hPSCs) can be injected to suitable animal host recipient blastocyst (such as C57BL/6J mouse blastocyst, which can be obtained by superovulation from 3-4 week old C57BL/6J female mice). Injected blastocysts can be transferred bilaterally to uterus of pseudopregnant CD-1 female mice at 7-9 weeks of age, with 14-18 blastocysts transferred per mouse. After 17.5 days of gestation, mouse embryos can be retrieved and further analyzed for detection of human cells in the embryos. The differentiation of naive hPSCs to cells of all three germ layers in mouse embryos is stochastic, driven by the developmental cues in the mouse embryos. The cells do not need to be treated prior to being transferred to mouse blastocysts.

In one embodiment, single cells (iPSCs) can be obtained from the culture and plating the single cells on feeders, such as MEF feeders, in 2iLI media. In one embodiment, the single cells are obtained by trypsinization. In an embodiment, the plating is performed for a time period from about 4 to about 7 days, including all integers and ranges in between, such as about 4 to about 5 days, about 5 to about 7 days and about 5 days.

In an embodiment wherein the GSK3β inhibitor is CHIR99021, the CHIR99021 is present at about 3 µM in a preferred embodiment. When the iPSCs are N4 iPSCs and the GSK3β inhibitor is CHIR99021, the CHIR99021 is present at about 0.8 µM. In an embodiment wherein the MEK inhibitor is PD0325091, the PD0325091 is present at about 1 µM.

When a batch of naive hPSCs are generated as described herein, a few cells can be tested for the ability to generate chimeras. The remaining naive hPSCs from the batch can be stored (for example, the cells can be frozen) for later use in the generation of a substantial number of cells of desired germ layer as needed for implantation into a human. The human may be the donor from which the original iPSCs were obtained, or may be a matched donor based on histocompatibility considerations.

This disclosure demonstrates that a transient treatment with Torin 1, a selective inhibitor of mTor, converted hPSCs from primed to naive pluripotency. The naive hPSCs were maintained in the same condition as mESCs in medium with 2iLI (2 inhibitors [MEK inhibitor and GSK3β inhibitor], LIF and Insulin). Like mESCs, the naive hPSCs exhibited high clonal efficiency, rapid cell proliferation, active mitochondrial respiration, X chromosome activation, DNA hypomethylation, and transcriptomes similar to those of human blastocysts than primed hESCs. Our naive hPSCs significantly contributed to mouse embryos when transferred to mouse blastocysts. This is an important distinction from previous published studies, which only generated so-called "naive" hPSCs that must be maintained in various chemical inhibitors or by forced expression of transgenes. The inhibitor-dependent so-called "naive" hPSCs do not significantly contribute to mouse embryos when they are injected into mouse blastocysts or morulas. These published works cannot be adapted to generate human organs in chimeric animals. Additionally, in at least some of these previous studies, the media cannot be used to culture mouse ESCs. Such media trap hPSCs in a state that is not the same as the naive state of pluripotency in which the mouse ESCs exit.

Furthermore, we found that mTor inhibition induced nuclear translocation of TFE3, TFE3 with mutated nuclear localization signal blocked the conversion from primed to naive pluripotency. Without being bound by any theory, it appears that by mimicking diapause at the cellular level, naive pluripotency in human can be readily attained from primed hPSCs, thus establishing the unified ground state of pluripotency in mammals.

All tables appearing in this application, regardless of location, are also fully a part of this application. Likewise, all methods and other text appearing in this application, regardless of location, are fully a part of this application.

The following examples are provided as illustrative examples and are not intended to be restrictive in any way.

Example 1

This example describes generation of N004 iPSC with the lentivirus method (Maherali et al. *Cell Stem Cell* 3, 340-345, 2008). For this method, human dermal fibroblasts ($1 \times 10^5$) were infected for 16 hr with the following six kinds of lentiviruses (hOct4, hSox4, hKlf4 and hNanog each at MOI 15, c-Myc at MOI 6, and M2rtTA at MOI 30) in the presence of 4 µg/ml polybrene. One day later, infected cells were plated at $1 \times 10^5$ cells on MEF feeders in 10 cm dishes in DMEM containing 10% FBS, 2 mM L-Glutamine, 50 U/ml penicillin and 50 mg/ml streptomycin. Next day, the media were changed to hESC media and the transgenes were induced by the addition of doxycycline. Doxycycline (1 µg/ml) was added for at least 10 days and later at 0.5 µg/ml until hESC-like clones appeared. VPA (0.5 or 1 mM) was added for 7 days with DOX in the beginning. After initial appearance and death of transformed cells, clones with hESC morphology appeared between day 24 and 40. They were picked and expanded under hESC culture condition.

C005 iPSC were generated using plasmids (Okita et al. A more efficient method to generate integration-free human iPS cells. *Nat. Methods* 8, 409-412, 2011). For this method, we electroporated the three plasmids (pCXLE-hOCT3/4-shp53-F, pCXLE-hSK (hSOX2+KIF4), and pCXLE-hUL (Lin28+Lmyc)) to $1 \times 10^6$ human dermal fibroblasts. After electroporation, cells were plated on MEF feeders and cultured in DMEM with 10% serum for 6 days, with media change every two days. On day 7, the media was changed to hES media and changed daily. iPS colonies emerged around day 14 and were manually picked around day 20-30 for expansion.

These iPSCs were converted to naive state.

Example 2

Results

Transient Torin1 Treatment Converts hPSCs to Naive State

We found that inhibition of mTor by Torin1 (FIG. 1*a-h*, FIG. 7*a-k"*) or rapamycin (FIG. 7*l-q"*) induced rapid translocation of TFE3 from cytoplasm to nucleus in primed H9 hESCs. TFE3, a transcription factor linking nutrient-sensing, stress and autophagy is located in the cytoplasm of mouse epiblast cells (Betschinger et al., *Cell* 153, 335-347 (2013)) and primed hESCs (Gafni et al., *Nature* 504, 282-286 (2013)) and human iPSCs (Hu et al., *Stem Cells Dev.* 24, 2591-2604 (2015)), but resides in the nucleus in naive mESCs (Betschinger et al., *Cell* 153, 335-347 (2013)) and naive hESCs maintained in chemical inhibitors (Gafni et al., *Nature* 504, 282-286 (2013)) or by transgenes. We found that inhibition of mTor by Torin1 (FIG. 1*a-h*, FIG. 7*a-k"*) or rapamycin (7*l-q"*) induced rapid translocation of TFE3 from cytoplasm to nucleus in H9 hESCs or other hPSCs.

Information on antibodies used in the study is shown in Table 1.

TABLE 1

| Antibody | Vendor | Dilution |
| --- | --- | --- |
| SSEA-3 | Millipore | 1:500 |
| SSEA-4 | Millipore | 1:500 |
| TRA-1-60 | Millipore | 1:1000 |
| TRA-1-81 | Millipore | 1:1000 |
| Oct4 | Millipore | 1:1000 |
| Nanog | Millipore | 1:1000 |
| Klf-4 | Millipore | 1:1000 |
| TFE3 | Sigma | 1:1000 |
| a-1-Fetoprotein (AFP) | Dako | 1:1000 |
| a-Smooth Muscle antibody (SMA) | Sigma | 1:800 |
| b3-tubulin (TuJ1) | BioLegend | 1:1000 |
| 5-methylcytosine (5mC) | Active motif | 1:1000 |
| 5-hydroxymethylcytosine (5hmC) | Active motif | 1:1000 |
| Histone H3K27me3 | Millipore | 1:2500 |
| Green Fluorescent Protein (GFP) | Millipore | 1:1000 |
| Green Fluorescent Protein (GFP) | DSHB/University of Iowa | 1:200 |
| LC3 | Santa Cruz | 1:1000 |
| Lamp-1 | DSHB/University of Iowa | 1:1000 |
| human red blood cells (hRBC) | Rockland | 1:4000 |
| Vimentin | Santa Cruz Biotechnology | 1:1000 |
| SLC4A1 (Band 3 anion transporter) | DSHB/University of Iowa | 1:1000 |
| Recoverin | Millipore | 1:1000 |

Based on the time course (FIG. 7a-f''') and dose response (FIG. 7g-k'') of Torin1-induced nuclear translocation of TFE3, we treated primed H9 hESCs with Torin1 (10 µM for 3 hr) in medium that is used for naive mESCs (Ying et al., Nature 453, 519-523 (2008) [50%/50% DMEM/F12: Neural Basal with 2i (1 µM PD0325901 and 3 µM CHIR99021), human LIF, N2 and B27 supplements], then dissociated the cells with TrypLE for replating on MEF feeders in the same medium without Torin1. After about 5 days, refractive, domed shaped colonies containing Nanog$^+$ cells were observed (FIG. 8a-a'''). Replacing N2 and B27 supplements, which contained undisclosed amount of insulin and many other components, with human insulin (18 µg/ml) produced much higher percentage of Nanog$^+$ cells among all human cells (hNA$^+$) grown on MEF feeders (FIG. 8b-b''' and j). We named this medium 2iLI. Removing human insulin from the 2iLI medium drastically reduced Nanog$^+$ cells and mESC-like colonies (FIG. 8c-c''' and j), so was the removal of human LIF, 2i, or one of the 2i (CH or PD) (FIG. 8d-g''' and j). High glucose concentration (21.25 mM) in the naive mESC medium or 21% O$_2$ markedly decreased the conversion (FIG. 8h-i''' and j), compared to 2iLI medium with physiological glucose concentration (5 mM) and O$_2$ tension (5%).

After primed H9 hESCs (FIG. 1i) were converted with the optimized condition (FIG. 1j), many colonies with mESC morphology were seen (FIG. 1k), picked and maintained in 2iLI medium (without Torin1) with 5 mM glucose and 5% O$_2$ for at least 56 passages without significant differentiation (FIG. 1l). In this condition, naive H9 maintained the expression of pluripotency markers such as Oct4, Nanog, Klf4, AP, TRA-1-60, TRA-1-81, SSEA-4 and SSEA-3 (FIG. 1m-t). In contrast, primed H9 failed to maintain pluripotency in 2iLI medium (FIG. 1u-x). Using the same method in FIG. 1j, we also converted H1 and RUES2 hESCs, and C005 human iPSCs to naive state (FIG. 9). The original C005 primed iPSCs were generated with non-integrating episomal plasmids (Okita et al., Nat. Methods 8, 409-412 (2011) (FIG. 8k). To test whether human primed iPSCs derived with integrating methods can also be converted to naive state, we used N004 iPSCs, which were generated with DOX-inducible lentiviruses expressing Oct4, Sox2, Klf4, c-Myc and Nanog (Jiang et al., Nat. Commun. 3, 668 (2012)) (FIG. 8k). By optimizing CHIR99021 concentration to 0.8 µM, N004 iPSCs were converted to naive state with the same method, without turning on transgenes (FIG. 8l and FIG. 9ae-an). The need to titrate CHIR99021 level may reflect slightly different epigenetic states of different iPSCs or the presence of transgenes.

Naive H9 and naive RUES2 exhibited a normal karyotype at passages 12 and 15, respectively (FIG. 10). Naive H9 was spontaneously differentiated in vitro to cells of all three germ layers (FIG. 11a-d). Teratomas containing cells of all three germ layers were formed when naive H9 cells were grafted under kidney capsules of SCID mice (FIG. 11e-g). Naive H9 cells were readily reverted to the primed state after the 2iLI medium was switched to hESC medium for 7 to 10 days (FIG. 11h-i). The reverted H9 (rH9) cells expressed pluripotency markers (FIG. 11j-p''), had growth rate (FIG. 11q) and clonal efficiency (FIG. 11r-s) similar to those of the original primed H9, but significantly lower than those of naive H9. The reverted H9 was differentiated spontaneously to cells of all three germ layers (FIG. 11t-v).

Cellular and Transcriptomic Properties of Naive hPSCs

Naive H9 and naive RUES2 had much higher clonal efficiency than their parental primed hESCs (FIG. 2a-d). Naive state also conferred significantly faster cell proliferation (FIG. 2e). Cell doubling time of naive H9 (14.9+3.6 hr) and naive RUES2 (12.9+4.1 hr) were much shorter than those of primed H9 (35.0+5.3 hr) and primed RUES2 (33.5+6.4 hr) (FIG. 2e inset). Mitochondrial respiration as revealed by the mitochondrial membrane potential indicator TMRE was nearly absent in primed H9 (FIG. 2f), and became very prominent in naive H9 (FIG. 2g). Seahorse analyzer showed that mitochondrial respiration was essentially absent in primed H9 and primed RUES2, but became very prominent in naive H9 and naive RUES2 (FIG. 12). Compared to primed H9, naive H9 had significantly higher utilization of Oct4 distal enhancer, and significantly lower reliance on Oct4 proximal enhancer (FIG. 2j). Principal Component Analysis (PCA) of RNAseq data (FIG. 2k) showed that our naive hESCs (HuN: triangles) bear similarities to single cells from human late blastocysts (Yan et al., Nat. Struct. Mol. Biol. 20, 1131-1139 (2013)) (Ya_LB: triangles) and the equivalent E5 to E7 preimplantation human embryos (Petropoulos et al., Cell 165, 1012-1026 (2016)) (PeE5, PeE6, and PeE7: pink, yellow and brown pluses, respectively), as well as naive hESCs established with various chemicals inhibitors (Takashima e al., Cell 158, 1254-1269 (2014); Sahakyan et al., Cell Stem Cell 20, 87-101 (2017); Grow et al., Nature 522, 221 225 (2015)). They were well separated from the parental primed hESCs (HuP, circles) and other hESCs, which were similar to each other. Clustering analysis of the RNAseq data (FIG. 2l) showed that our naive hESCs (HuN, two branches for nH9 and nRUES2) were similar to naive hPSCs from several other groups (GrN, Sa a and Ta N), but were quite different from out primed hESCs (Hu_P, two branches for H9 and RUES2 and other primed hPSCs. The 1811 coding genes that were differentially expressed between our naive and primed hPSCs showed similar differential expression patterns in naive and primed hPSCs from other groups (FIG. 2m). Primed-to-naive conversion increases the expression of some transposable elements. We analyzed the expression of transposable elements in the RNAseq data and found that the 889 transposable elements differentially expressed between our naive and primed hPSCs had similar differential expression patterns in naive and primed hPSCs from other groups (FIG. 2n). The expression levels of HERVK and LTR5_Hs were significantly increased in naive hPSCs including ours (Hu_*, filled boxes) (FIG. 2O).

Female Naive hPSCs Reactivate X-Inactivated Genes

Figure 3:
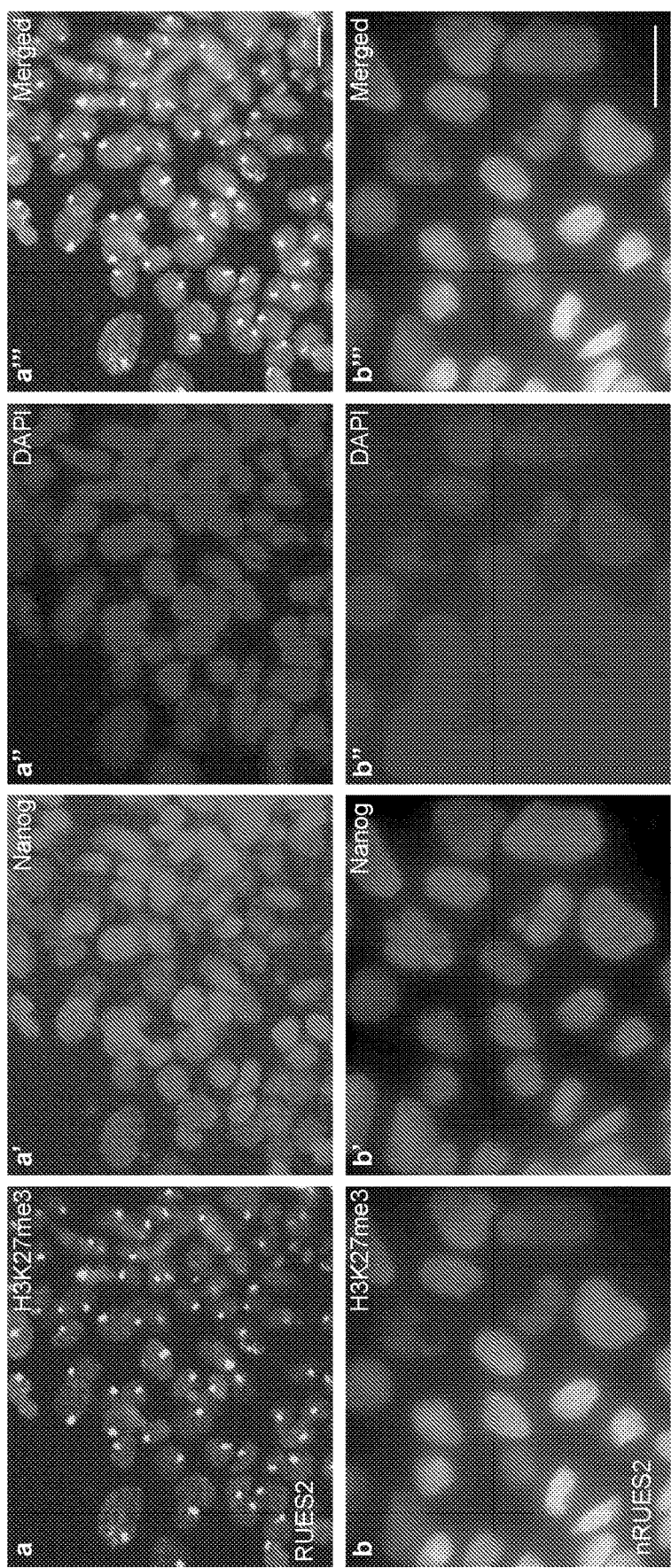
FIG. 3. Reactivation of x-inactivated genes in naive hPSCs. (a-b''') X chromosome inactivation in primed RUES2 (a-a''') and reactivation in naive RUES2 (b-b''') as revealed by costaining for H3K27me3 (a, b), Nanog (a', b') and DAPI (a'', b''). (c) Ratio of the expression level of genes on each chromosome in naive vs. primed hPSCs. $X_i$, X-inactivated genes (Carrel et al., *Nature* 434, 400-404 (2005)); $X_e$, X-escaped genes (Carrel et al., *Nature* 434, 400-404
Figure 3:
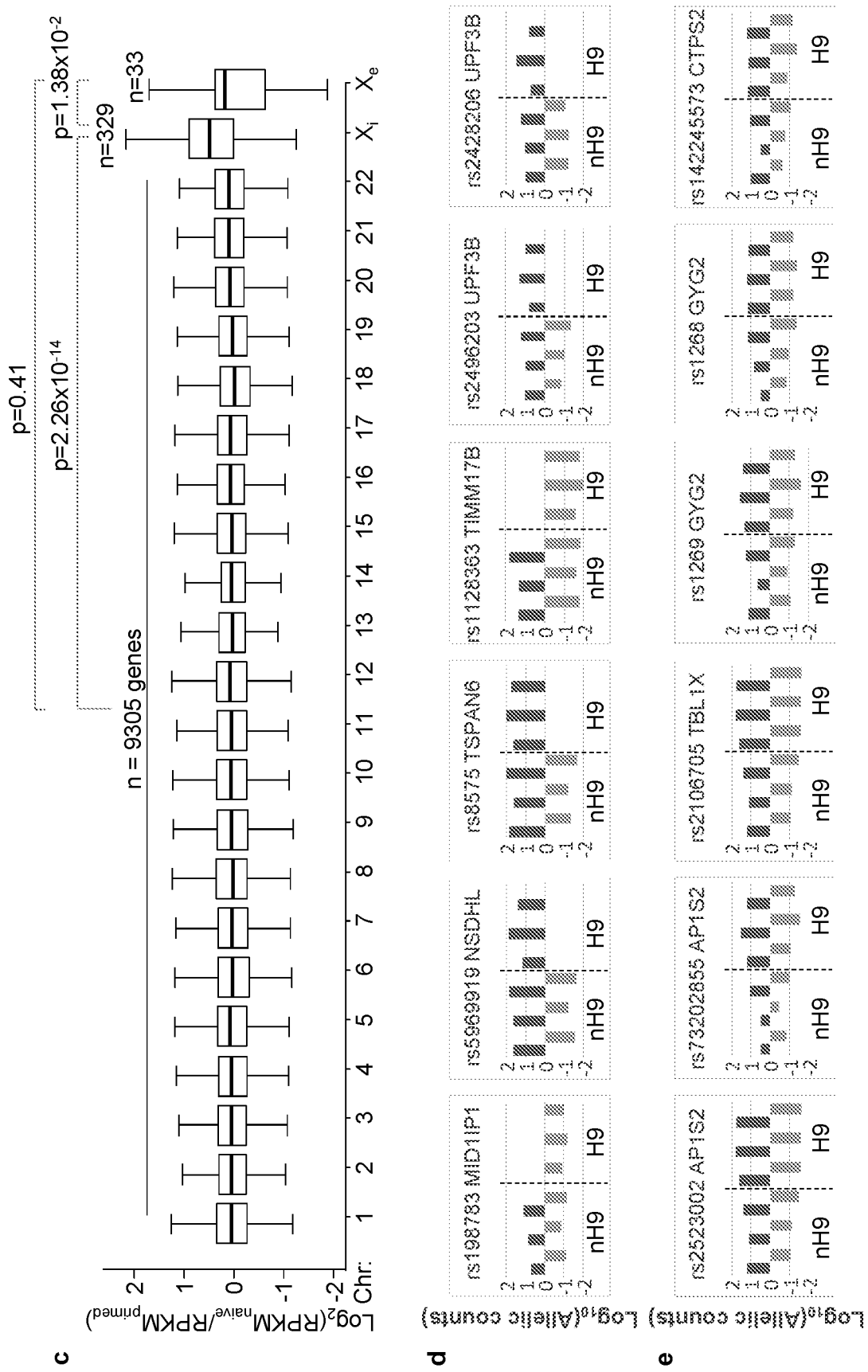

Naive pluripotency in female cells is characterized by two active X chromosomes (XaXa), instead of the inactivation of one X-chromosome in primed pluripotency (XaXi) (Boroviak et al., Development 144, 175-186 (2017)). We used an antibody against histone H3K27me3 to probe the X-inactivation status and found a single spot in the nucleus of RUES2 cells (FIG. 3a-a''') and diffuse staining in the nucleus of naive RUES2 cells (FIG. 3b-b'''). We analyzed our RNAseq data for the expression levels of genes on the 22 autosomes, X-inactivated ($X_i$) genes and X-chromosome genes that escaped X-inactivation ($X_e$). The ratio of gene expression levels between naive H9 and primed H9 was significantly increased for the X-inactivated genes, but not for the X-escaped genes or autosomal genes (FIG. 3c). By identifying Single Nucleotide Polymorphisms (SNPs) in our RNAseq data from primed H9 and naive H9, we analyzed the allelic expression of X-chromosome genes. A number of X-inactivated genes that were monoallelically expressed in primed H9 became biallelically expressed in naive H9 (FIG. 3d). In contrast, a sample of X-escaped genes were biallelically expressed in both primed H9 and naive H9 (FIG. 3e).

DNA Hypomethylation in Naive hPSCs

The levels of 5mC (FIG. 4a,b) and 5hmC (FIG. 4a',b') were markedly decreased when primed H9 (FIG. 4a-a''') were converted to the naive state (FIG. 4b-b'''). Dot blot analysis of genomic DNA isolated from primed H9, naive H9 (nH9) and AB2.2 mESCs showed that 5mC levels were significantly reduced from H9 to nH9, to levels similar to those in mESCs (FIG. 4c-d). Significant decrease in 5hmC levels was also found from H9 to nH9 (FIG. 4e-f). We examined genome-wide methylation state in primed and naive H9 and RUES2 using Infinium MethylationEPIC Beadchip from Illumina. Principle component analysis showed a large separation between primed and naive hESCs along principal component 1 (PC 1), explaining 79% of total variance (FIG. 4g). This indicates that primed and naive hESCs have distinct DNA methylation signatures. Further analysis identified 128,383 tiling regions (out of a total of 251,092), 24,812 promoters (out of a total of 44,854) and 24,692 gene bodies (out of a total of 34,931) that were differentially methylated between naive and primed hESCs. More than 93% of the differentially methylated regions (96.1% of tiling regions, 93.5% of promoters, 96.8% of gene bodies) were demethylated in primed-to-naive conversion. The information is illustrated in the heatmap of the 128,383 differentially methylated tiling regions in primed and naive hPSCs, which showed clearly different patterns of DNA methylation (FIG. 4h). We observed different DNA methylation patterns in imprinted regions between primed and naive hESCs. Some imprinted regions decreased DNA methylation, while other imprinted regions increased DNA methylation during the conversion of hPSCs from primed to naive state (FIG. 4i).

Naive hPSCs Generate Large Amounts of Mature Human Cells in Mouse Embryos

We transferred naive hPSCs to mouse blastocysts in three rounds of experiments (FIG. 13a). In the two successful rounds, 17.5 days after the injected blastocysts were transferred to pseudopregnant mice, we retrieved mouse embryos, which appeared normal (FIG. 13b). In an embryo from mouse blastocysts injected with naive N004 iPSCs (nN004-2), we found a large amount of GFP+ human cells (FIG. 5a). The specificity of GFP fluorescence and GFP-DAB staining is shown in FIG. 14. At a z-level away from that in FIG. 5a, two neighboring sections of nN004-2 embryo were DAB-stained with anti-GFP (FIG. 5b) or stained with Hematoxylin and Eosin (H&E) (FIG. 5c, with boxes 1 and 2 enlarged in FIG. 5d, e, respectively) for tissue identification. The GFP+ human cells in areas highlighted by arrows and box 1 (FIG. 5b) contained red blood cells (RBC) (FIG. 5c, d). The GFP+ human cells in box 2 (FIG. 5b) corresponded to retinal pigmented epithelium (FIG. 5c, e). At a z-level between FIG. 5a and FIG. 5b, a section of this embryo was DAB-stained with an antibody against human red blood cells (hRBC). A large amount of cells, including those corresponding to box 1 in FIG. 5b,c and to the large block of GFP+ cells in FIG. 5a, were human red blood cells (mesoderm) (FIG. 5f). Costaining for GFP, hRBC and DAPI confirmed that the GFP+ human cells were enucleated RBCs (FIG. 5g-g'''), which correspond to boxes in FIG. 13c-c''' for a zoomed-out view). The striking finding was substantiated by costaining for GFP, the RBC-specific Band 3 protein and DAPI (FIG. 5h-h'''). We also found that some GFP+ human cells were AFP+ endoderm cells (FIG. 5i-i'''). Costaining for GFP, recoverin (a protein expressed in photoreceptors) and DAPI identified a large amount of human photoreceptors (ectoderm) (FIG. 5j-j'''), with the box enlarged in FIG. 13d), which corresponded to the GFP+(FIG. 5b) retinal cells (FIG. 5c) in box 2 (FIG. 5e). Additional costaining found that some of the GFP+ human cells were SMA+ mesoderm cells (FIG. 13e-e'') and vimentin+ cells (FIG. 13f-f''). Thus, the nN004-2 embryo contained human cells of all three germ layers. Similarly, the nC005-1 embryo also contained human cells of all three germ layers (FIG. 13g-l'''). The nRUES2-10 embryo contained large amounts of GFP+ cells, some of which were SMA+ (FIG. 13m-r''). GFP-DAB staining was shown for all available embryos (FIG. 15). Identification of large amounts of human red blood cells was shown for two representative nRUES2 embryos (FIG. 16).

We detected GFP DNA in genomic DNA isolated from the 14 mouse embryos derived from blastocysts injected with GFP-labeled nRUES2 (1-14), but not from the 4 embryos from unlabeled nRUES2 (i-iv) (FIG. 5k, see FIG. 13a, second round). Individual-specific human genomic DNA was detected in embryos 1-14, but not i-iv, using DNA fingerprinting primers for the TPA-25 Alu insert (FIG. 5l) or the D1S80 variable number tandem repeats (VNTR) (FIG. 5m). Embryos i-iv apparently did not contain significant amount of human cells originated from nRUES2. The detection of a single copy DNA fragment in human genomic DNA is a much more stringent test than the detection of human mitochondrial DNA, which has on average $10^3$ to $10^4$ copies in a cell. The ability of DNA fingerprinting to distinguish different individuals was confirmed in Supplementary FIG. 11.

Primed-to-Naive Conversion is Dependent on Nuclear Translocation of TFE3

To explore the mechanism of the conversion, we generated primed H9 hESCs stably overexpressing TFE3-GFP fusion proteins (FIG. 6a-c) or GFP-tagged TFE3 with mutated Nuclear Localization Signal (NLS), which largely resided in the cytoplasm as puncta (FIG. 6d-f). When both lines of primed hESCs were treated with Torin1 (10 µM for 3 hr) in the conversion protocol (FIG. 1j), TFE3-GFP was enriched exclusively in the nucleus (FIG. 6g-j), while NLS-GFP remained largely in cytoplasm (FIG. 6k-n). Nanog+ naive hESC colonies were readily obtained from H9 cells expressing wild-type TFE3 (FIG. 6g-j, o-p), but not its NLS mutant (FIG. 6k-o, q). The small percentage of Nanog+ cells with the NLS mutant TFE3 did not exhibit mESC morphology and very quickly differentiated. We were unable to establish naive hESC line from primed H9 overexpressing NLS-GFP with the same condition that readily generated naive H9 hESC overexpressing TFE3-GFP. Overexpression of the TFE3 NLS mutant apparently acted in a dominant negative manner to block the action of endogenous TFE3, as the activation of TFE3 requires dimerization.

TFE3 is localized in the nucleus in naive hPSCs, which were cultured in 2iLI media without Torin1 (FIG. 18a-a″). Expression of wild-type TFE3 (FIG. 18b-f) or its NLS mutant (FIG. 18g-k) did not appreciably affect the pluripotency of primed H9 cells, as shown by the expression of pluripotency markers and their in vitro spontaneous differentiation to cells of all three germ layers. It suggests that TFE3 NLS mutant does not have non-specific toxicity.

Costaining for LC3 and Lamp1 showed that mTor inhibition for 3 hr by Torin1 (FIG. 19b-b‴) or rapamycin (FIG. 19c-c‴) induced autophagy in primed H9 cultured in hESC medium (FIG. 19a-a‴). Autophagy was slightly induced when hESC medium was changed to 2iLI medium for 3 hr (but maintaining 21.25 mM glucose) (FIG. 19d-d‴). Reducing glucose level from 21.25 mM to 5 mM in 2iLI medium significantly increased autophagy further (FIG. 19e-e‴). The combined treatment in 2iLI medium with 5 mM glucose and 10 μM Torin1 for 3 hr induced autophagy most prominently (FIG. 19f-f‴), as quantified in FIG. 19g. However, primed-to-naive conversion was not significantly affected by blocking autophagy with the Ulk1 inhibitor SBI-0206965 or by inducing autophagy with amino acid deprivation (FIG. 20). It suggests that Torin1-induced autophagy is not critical for the conversion. Changes in autophagy in response to treatments in FIG. 20 were shown in FIG. 21.

Discussion

Figure 1:
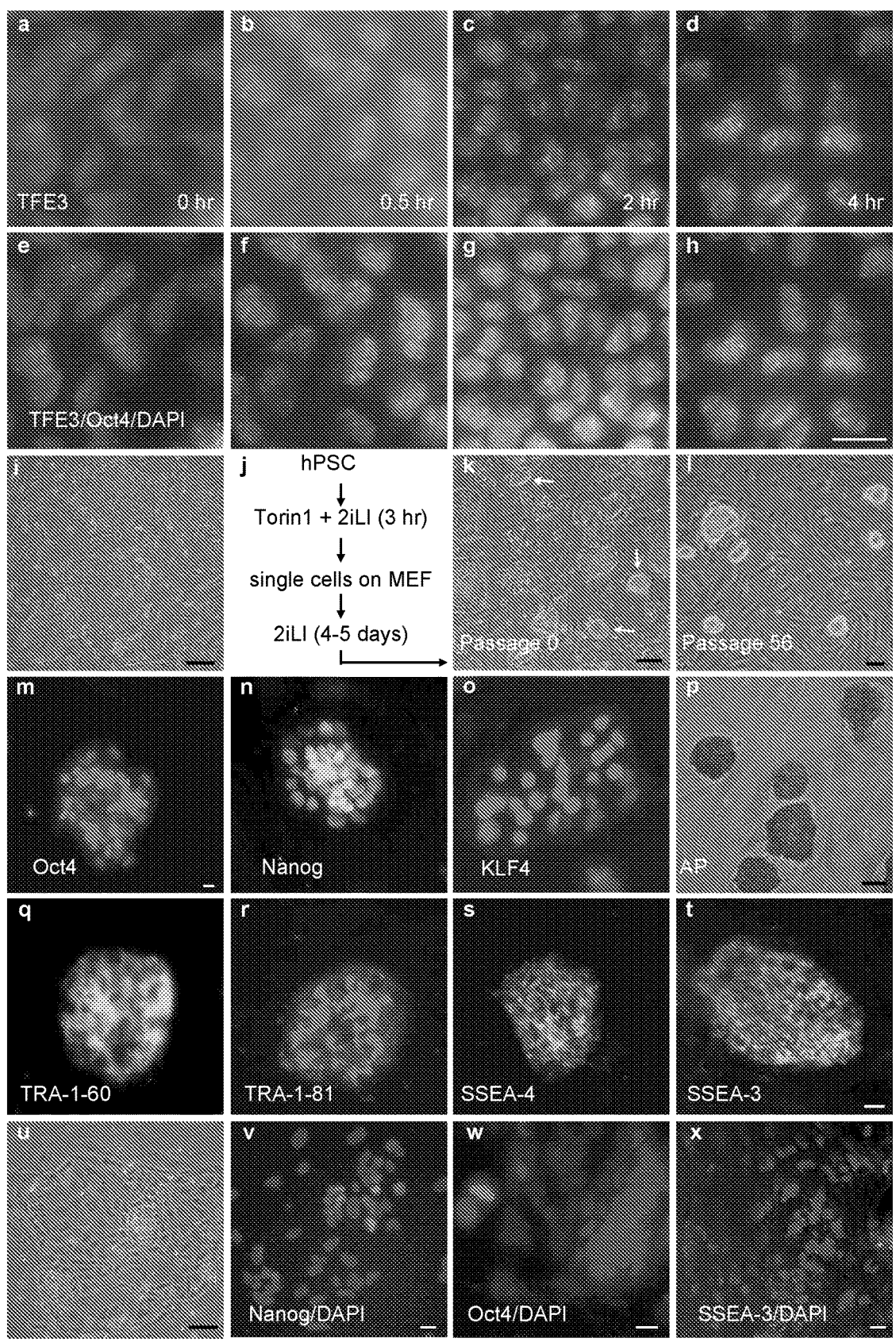
FIG. 1. Converting hPSCs from primed to naive pluripotency. (a-h) Localization of TFE3 in primed H9 hESCs treated with 10 µM Torin1 for the indicated durations. (i-l) Primed H9 (i) were converted with the protocol in (j) to dome-shaped colonies (k, arrows), which were picked and passaged (l). (m-t) Expression of pluripotency markers in naive H9 cultured in 2iLI medium. (u-x) In 2iLI medium, primed H9 differentiated (u) and lost the expression of pluripotency markers (v-x). White bars, 10 µm; black bars, 100 µm.
Figure 2:
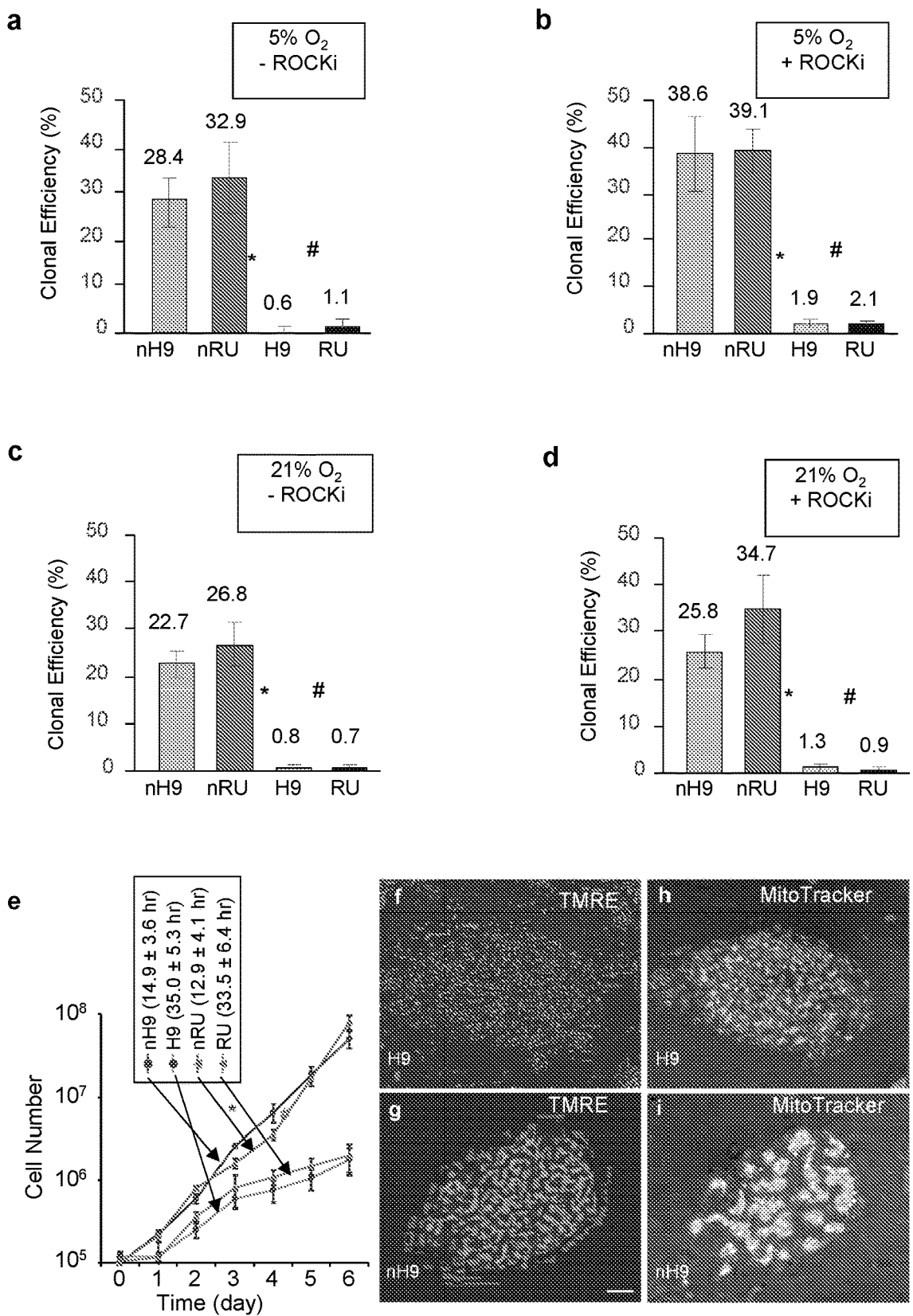
FIG. 2. Cellular and transcriptomic properties of naive hPSCs. (a-d) Clonal efficiencies of naive and primed H9 and RUES2 cultured in 5% $O_2$ (a, b) or 21% $O_2$ (c, d), in the absence (a, c) or presence (b, d) of ROCK inhibitor. *, #, $p<0.05$, n=3, unpaired, two-tailed t-test, vs. naive H9 (nH9) or naive RUES2 (nRU), respectively. (e) Growth curve and cell doubling time of primed and naive H9 and RUES2. *, #, $p<0.05$, n=4, repeated measures ANOVA, vs. primed H9 or primed RUES2 (RU), respectively. (f-i) Primed H9 and naive H9 were live-stained with TMRE to detect mitochondrial inner membrane potential (f, g) or MitoTracker to locate mitochondria (h, i). (j) H3K27Ac CHIP assays showing the utilization of Oct4 Distal Enhancer (DE) and Proximal Enhancer (PE) in primed H9 and naive H9. $p<0.05$, n=6, vs. H9. (k-l) PCA analysis (k) and clustering analysis (l) of RNAseq data from naive (Hu_N) and primed (Hu_P) H9 and RUES2 against data on single cells from human late blastocysts (Yan e al., *Nat. Struct. Mol. Biol.* 20, 1131-1139 (2013)) (Ya_LB), human E5, E6, E7 embryos (Petropoulos et al., *Cell* 165, 1012-1026 (2016)), (Pe_E5, Pe_E6, Pe_E7), hESCs (Yan e al., *Nat. Struct. Mol. Biol.* 20, 1131-1139 (2013)), (Ya_ESC), or bulk RNAseq data from naive hPSCs maintained in chemical inhibitors (Sa_N (Sahakyan et al., *Cell Stem Cell* 20, 87-101 (2017)), Ta_N (Takashima et al., *Cell* 158, 1254-1269 (2014)), Ch_N (Chan et al., *Cell Stem Cell* 13, 663-675 (2013)), Gr_N (Grow et al., *Nature* 522, 221-225 (2015)) and their parental primed hPSCs (Sa_P (Sahakyan et al., *Cell Stem Cell* 20, 87-101 (2017)), Ta_P (Takashima et al., *Cell* 158, 1254-1269 (2014)), Ch_P (Chan et al., *Cell Stem Cell* 13, 663-675 (2013)), Gr_P (Grow et al., *Nature* 522, 221-225 (2015))). (m) Coding genes that were differentially expressed between our naive (underlined light grey) and primed (underlined dark grey) H9 and RUES2, as compared to expression patterns in other naive and primed hPSCs. (n) Transposable elements that were differentially expressed between our naive (underlined light grey) and primed (underlined dark grey) H9 and RUES2, as compared to expression patterns in other naive and primed hPSCs. (o) Increased expression of transposable elements such as HERVK and LTR5_Hs in our naive cells (Hu_*, filled boxes) and other naive cells (open boxes), as compared to their corresponding primed hPSCs.
Figure 2:
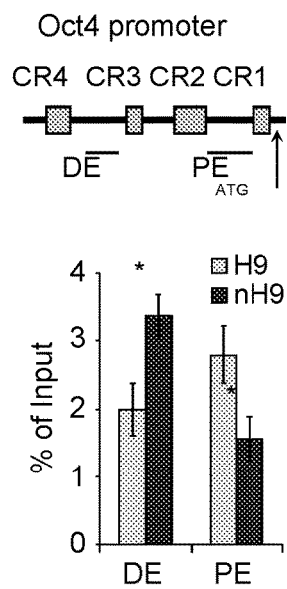
Figure 2:
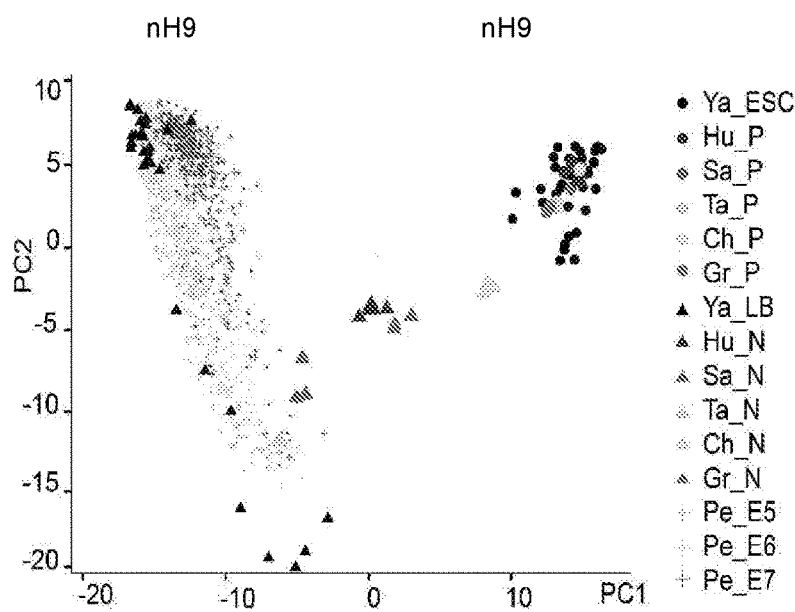
Figure 2:
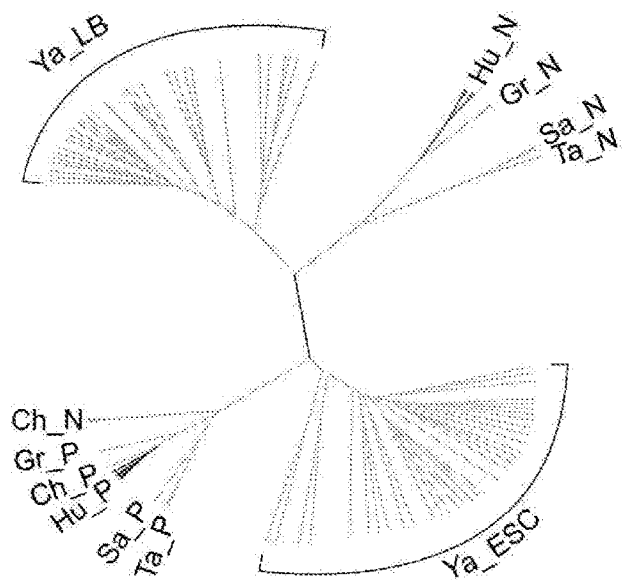
Figure 2:
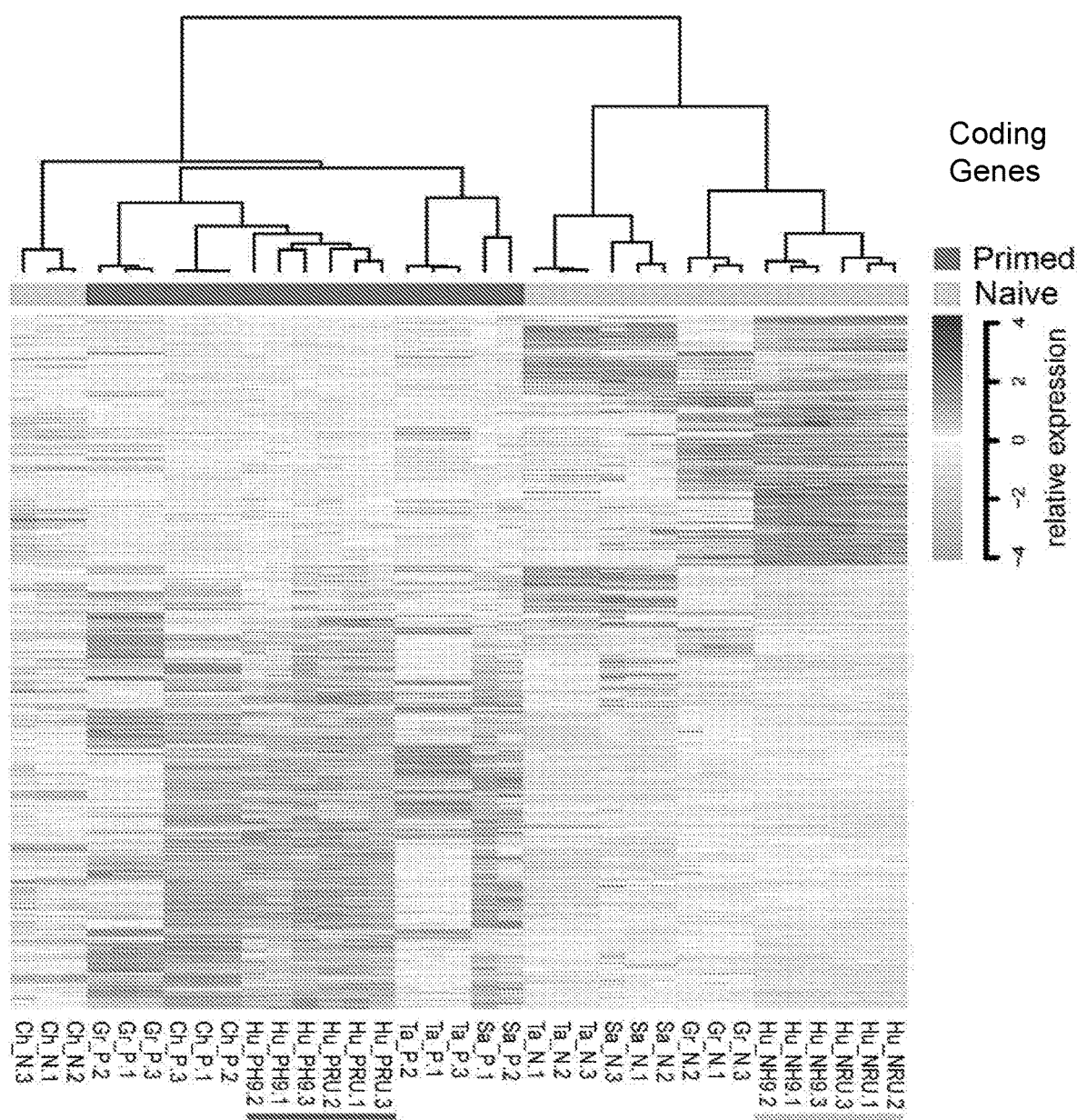
Figure 2:
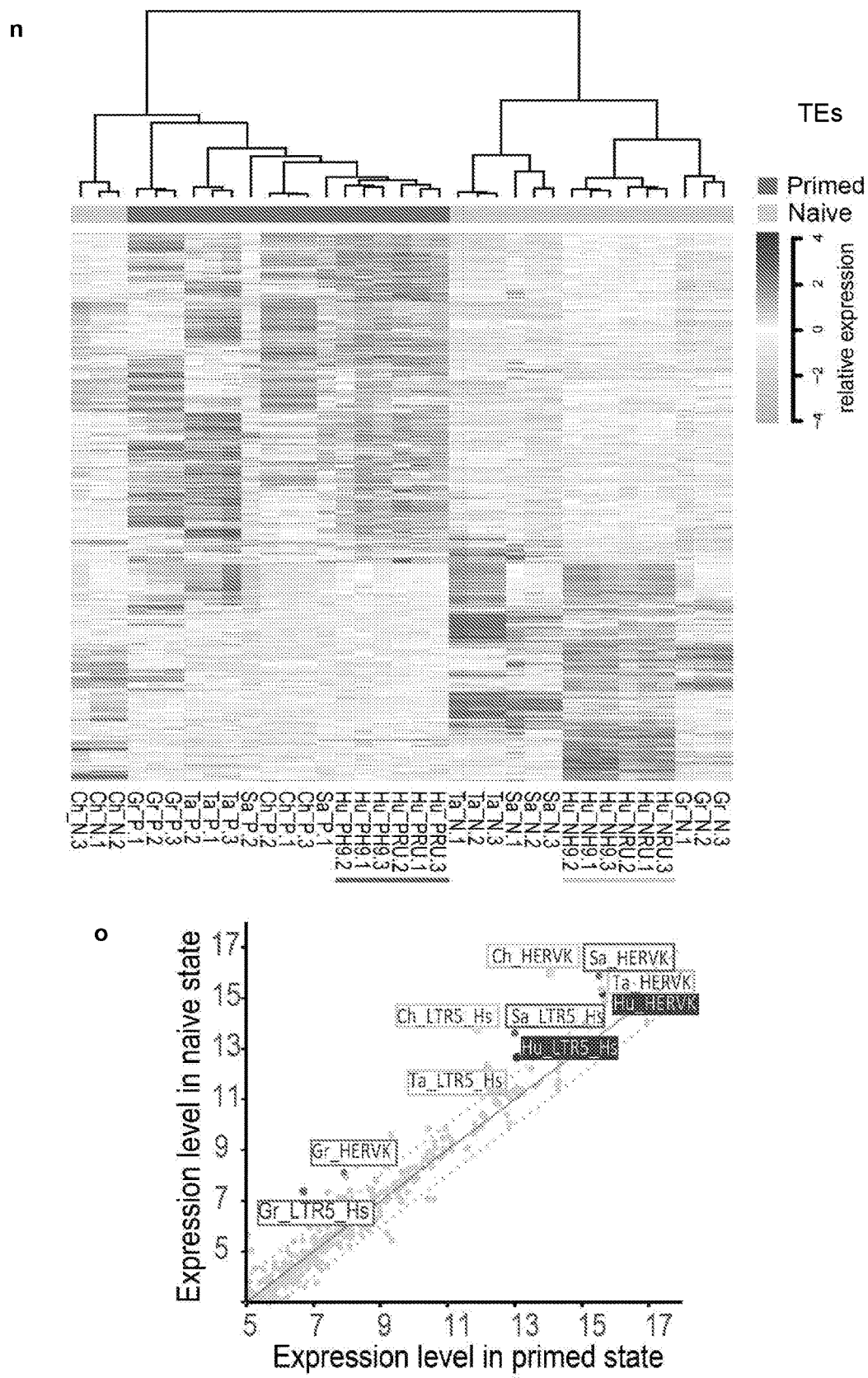

In this study, it was found an efficient method for the conversion of hPSCs from primed to naive pluripotency by a 3 hr treatment with Torin1 (FIG. 1). The conversion of the cells and their subsequent culture were in defined medium essentially similar to that used for maintaining mESCs in naive pluripotency (Ying et al., Nature 453, 519-523 (2008)). The only differences, which markedly improved the derivation of naive hPSCs, were the replacement of undefined N2 and B27 supplements with human insulin, as well as the reduction of glucose concentration and $O_2$ tension to physiological levels (FIG. 8). The naive hPSCs, which can be derived from either hESCs or hiPSCs, passed generally accepted criteria for naive pluripotency (De Los et al., Nature 525, 469-478 (2015); Boroviak et al., Development 144, 175-186 (2017)) (FIGS. 2-5, FIGS. 12-17), except for germline transmission and tetraploid complementation, which cannot be tested for ethical reasons. It appears that the nuclear translocation of TFE3 induced by Torin1 underlies the facile conversion from primed to naive pluripotency (FIG. 6). Torin1-induced nuclear translocation of TFE3 activates transcription events that lead to the conversion from primed to naive pluripotency. Although the exact mechanistic details await further studies, blocking or inducing autophagy did not significantly affect Torin1-induced conversion (FIGS. 20-21).

By confining the culture condition of naive hPSCs to that of mESCs, we unified the ground state of pluripotency in mammals. Indeed, the most striking finding of the study is the robust contribution of naive hPSCs to human cells of all three germ layers in chimeric mouse-human embryos (FIG. 5 and FIGS. 13-17). The identification of large amounts of enucleated human red blood cells and photoreceptors after 17.5 days of gestation showed that the development of naive hPSCs was markedly accelerated to match the mouse embryos. Human embryos at this stage do not have such mature cells. The derivation of chimera-competent naive hPSCs may enable many applications previously impossible in the human system, such as selection-driven heterologous organ generation in chimeric animals.

Methods

Regulatory Approvals

All mouse embryos were euthanized immediately upon retrieval from mice at E10.5 or E17.5 by immersing them in 4% paraformaldehyde (PFA). Animal welfare is not affected in this process. We did not detect contribution of human cells to germ line tissues. In nC005-1 embryo, we detected Nestin+ or PAX6+ human neural cells (FIG. 13k-l‴). In nN004-2 embryo, we detected significant amounts of human cells in the retina (FIG. 5j-j‴ and FIG. 13d). This did not affect the function or welfare of the pregnant mice or the embryos, because the embryonic eye was not capable of vision yet and the embryonic brain probably contained too few human neural cells to affect embryonic mouse brain functions.

Culture of Primed State Human Pluripotent Stem Cells

Human pluripotent stem cells (hPSCs), including human embryonic stem cell (hESC) lines H1 at passages 40-42 (WiCell), H9 at passages 31-35 (WiCell), RUES2 at passages 30-33 (Rockefeller University) and human induced pluripotent stem cell (iPSC) lines C005 at passages 25-28 and N004 at passages 21-25 were maintained on mitomycin C-treated mouse embryonic fibroblast (MEF) feeders in hESC medium (DMEM/F12 containing 20% knockout serum replacement, 2 mM glutamine, 1% nonessential amino acids (NEAA), 100 U/ml penicillin, 100 μg/ml streptomycin (Life Technologies), 0.1 mM β-mercaptoethanol (Sigma), and 4 ng/mL bFGF (PeproTech). Medium was changed daily and cells were passaged every 6-7 days using dispase (1 mg/mL, Life Technologies). Unless indicated otherwise, all primed and naive hPSCs were cultured in 5% $O_2$ and 5% $CO_2$. All cells were tested regularly for mycoplasma contamination by PCR. No mycoplasma was detected.

Converting hPSCs from Primed State to Naive State

Primed hPSCs were treated with 10 μM ROCK inhibitor Y27632 (Abcam) overnight in hESC medium. After being washed twice in phosphate-buffered saline (PBS), primed hPSCs were cultured in 2iLI medium with 10 μM Torin1 (Tocris) for 3 hours. 2iLI medium contained 50% glucose-free DMEM/F12 (Life Technologies) and 50% glucose-free Neurobasal (Life Technologies), 5 mM glucose, 1 mM glutamine, 1% NEAA, 0.1 mM 3-mercaptoethanol, 100 U/ml penicillin, 100 μg/ml streptomycin, 5 mg/mL bovine serum albumin (Sigma) to maintain osmolarity, 20 ng/mL recombinant human LIF (Millipore), 18 g/ml human insulin (Sigma), 1 μM PD0325901 (PD, EMD Millipore), and 3 μM CHIR99021 (CH, Stemgent). For N004 iPSCs, 2iLI medium with 0.8 μM CHIR99021 was used instead. Then hPSCs were trypsinized into single cells using TrypLE (Life Technologies) for 5 min at 37° C. The single cells were plated on MEF feeders ($5-6 \times 10^4/cm^2$) in 2iLI medium (without Torin1), which was changed daily. For N004 iPSCs, 2iLI medium with 0.8 μM CHIR99021 was used instead. Small, bright, dome-shaped colonies appeared in 4-5 days and were picked manually at day 5-7 for dissociation by TrypLE into single cells, which were plated on fresh MEF cells. After several manual passages, mouse ESC-like colonies were uniformly seen and passaged every 3 days with TrypLE and maintained in 2iLI media (without Torin1).

Immunostaining

Immunostaining was performed using standard protocol to detect various antigens in cultured cells or frozen tissue sections. Briefly, cells or tissue sections were fixed in 4% paraformaldehyde (Sigma) for 20 min, treated with 0.1% Triton X-100 for 15 min at room temperature for permeabilization, blocked in 3% BSA for 1 hour at room temperature, and then incubated with the indicated primary antibodies (Table S1) overnight at 4° C. and secondary antibodies for 1 h at 37° C. Secondary antibodies were AlexaFluor 488, 594, and 647 (1:1,000, Thermo fisher Scientific). Alkaline phosphatase (AP) staining was performed using the Alkaline Phosphatase Kit (Millipore). Diaminobenzidine (DAB) staining was also used to detect GFP expression in frozen embryo sections according to manufacturer's protocol (Vector Laboratories). Briefly, the frozen sections on slides were thawed at room temperature for 5 min. Then the slides were treated with 0.3% $H_2O_2$ solution in PBS at room temperature for 10 min to block endogenous peroxidase activity, and then treated with 3% BSA for 45 min for blocking. The sections were incubated with primary antibody (anti-GFP) in 0.1% BSA for 30 min at room temperature, rinsed briefly in PBS 3 times (5 min each), and then incubated with biotinylated secondary antibody for 30 min followed by PBS rinsing for 3 times (5 min each). The sections were incubated with VECTASTAIN ABC reagent (Vector Laboratories) for 30 min, washed with PBS for 5 min. The sections were incubated with 100 µl peroxidase substrate solution (Sigma, D4293) on the slide under microscope until desired staining intensity and then washed with PBS to remove the substrate solution. For live imaging of mitochondria, primed or naive hPSCs were incubated in prewarmed hESC medium (for primed hPSCs) or 2iLI medium (for naive hPSCs) containing 50 nM MitoTracker Green FM or 100 nM TMRE (Life Technologies) for 15 min at 37° C. Then the staining medium was replaced with the corresponding prewarmed medium without dyes. Cells were then imaged on a Leica DMI6000B fluorescence microscope. Quantification of LC3II puncta was performed using NIH ImageJ with the AUTOCOUNTER pluggin, which calculates the percentage of cell area covered by LC3II puncta.

Measurement of Clonal Efficiency

Naive hESCs (nH9 and nRUES2) or primed hESCs (H9 and RUES2) were trypsinized into single cells and replated on MEF feeders in 2iLI medium or hESC medium without or with the ROCK inhibitor Y27632 (10 µM). They were cultured in incubators with 21% or 5% $O_2$ for three days for naive hESCs or seven days for primed hESCs. The numbers of naive or primed hESC colonies were counted by alkaline phosphatase (AP) staining to quantify clonal efficiency, which is the ratio of AP+ colonies over the number of single cells plated, expressed in percentage.

Measurement of Cell Doubling Time

Cell doubling time was measured as previously described by plating $1\times10^5$ naive or primed hPSCs on MEF cells in 24-well plates. The numbers of hPSCs in triplicate wells were counted using trypan blue exclusion on a hemocytometer at day 1, 2, 3, 4, 5, and 6 day after plating. Cell doubling time was calculated using the calculator at doubling-time.com/compute.php.

Reversion of Naive hPSCs to the Primed State

Naive hPSC colonies were picked manually, washed once in DMEM/F12 medium, and then plated on MEF feeders in hESC medium. Typical flat hESC colonies appeared in the culture in 7-10 days. These reversed primed state hPSCs were passaged every 5-7 days using dispase (1 mg/ml).

Spontaneous Differentiation of Naive hPSCs In Vitro

Naive hPSCs were dissociated into single cells by TrypLE treatment for 5 min at 37° C. and cultured in suspension in ultra-low attachment 96 well plates (Corning) in differentiation medium (DMEM/F12 with 10% FBS, 1% nonessential amino acids, and 1% penicillin/streptomycin) for 4-6 days to form embryoid bodies, which were plated on gelatin-coated 24-well plates in differentiation medium for another 2-4 weeks of attachment culture.

Teratoma Formation Assay

Teratoma formation assay was performed by the Mouse Tumor Model Resource at Roswell Park Cancer Institute following approved protocol. All animal experiments were done by staff members in core facilities in blinded fashion. The persons who performed the animal procedures only knew the codes assigned to the cells, not what kind of cells they were. Briefly, 1 million naive hPSCs were mixed with collagen at 1:1 ratio to form 10 µl mixture, which was plated on parafilm to solidify at room temperature for 1 h. Three such pellets were grafted under the renal capsule of each kidney in a male SCID mouse (C.B-Igh-1bIcrTac-Prkdcscid/Ros) around 17 weeks of age. Animals were monitored for palpable tumors around the kidney area. Large tumors (~1 cm in size) were generally found 2-3 months after grafting. Tumors were harvested and dissected into small pieces and fixed for 24 h in 10% formalin and processed for paraffin embedding. Tissue sections (5 µm) were stained with Hematoxylin and eosin for histological identification.

Mitochondrial Respiration

Mitochondrial respiration in naive hPSCs was assessed by measuring oxygen consumption rate (OCR) in a Seahorse XFe24 analyzer according to the manufacturer's protocol. Briefly, naive hPSCs were dissociated with TrypLE and replated at $8\times10^5$/ml in 2iLI medium in 100 µl volume on laminin-coated XF24 cell culture plates (Seahorse Bioscience) and cultured overnight at 37° C. in 5% $O_2$ and 5% $CO_2$. Culture medium was replaced with XF Base Medium (Seahorse Bioscience) supplemented with 2 mM pyruvate and 5 mM glucose at pH7.4. Cells were incubated at 37° C. in the machine for one hour to allow assay medium to pre-equilibrate. Oligomycin (2 µM), FCCP (0.5 µM), antimycin (1 µM) and rotenone (1 µM) were injected during the assay. The results of Cell Mito Stress Test were calculated using the manufacture's software (Seahorse Bioscience).

PCR Detection of Reprogramming Footprint in the Derivation of iPSCs

PCR on was performed to detect EBNA plasmids in genomic DNA isolated from primed C005 human iPSC, which was generated using episomal plasmids or lentiviral transgene expressing Oct4 in genomic DNA isolated primed N004 human iPSC, which was generated using DOX-inducible lentiviruses expressing Oct4, Sox2, Klf4, c-Myc and Nanog. The primers for detecting EBNA plasmids are GCAACATTAGCCCACCGTGCTCTC (SEQ ID NO: 1) and GGTTATTAAGATGTGTCCCAGGC (SEQ ID NO:2). The primers for detecting Oct4 lentivirus were CCCCAGGGCCCCATTTTGGTACC (SEQ ID NO:3) and AAAGCAGCGTATCCACATAGCGTA (SEQ ID NO:4).

Dot Blot Analysis of 5mC and 5hmC

Genomic DNA isolated from different types of cells was denatured at 99° C. for 5 minutes and snap cooled on ice. 5 µl of sample was spotted on positively charged nylon membrane (Bio Rad), air-dried, and cross-linked by UV. The membrane was washed with 2xSSC buffer, blocked with 5% milk in TBST (1xTBS+0.1% Tween-20) for 60 minutes and incubated with 5mC antibody (1:500) or 5hmC antibody (1:500) in blocking solution at room temperature for 1 hour. The membrane was washed 3 to 4 times with TBST at room temperature for 5-10 min per wash, incubated with HRP-conjugated anti-rabbit IgG secondary antibody (1:1000) at room temperature for 60 min, then washed with TBST at room temperature for 4 times (5 minutes each). The membrane was treated with enhanced chemiluminescence reagent (Thermo fisher Scientific). The signals were captured on Gel Imaging Systems (Bio-Rad) and analyzed using the Image Lab software (Bio-Rad).

RNA-Seq and Bioinformatics Analysis

RNA-seq was performed on primed H9 (PH9), naive H9 (NH9), primed RUES2 (PRUES2), and naive RUES2 (NRUES2) with 3 biological replicates for each line. For each sample, colonies of hPSCs were manually picked and homologized in 1 ml TRIzol reagent (Thermo Fisher Scientific). RNeasy Mini Kit (QIAGEN) was used for RNA extraction. Quality of purified RNA was monitored by agarose gel electrophoresis. PolyA$^+$ RNA enrichment, cDNA library preparation, sequencing and RPKM calculation were performed at the University at Buffalo Genomics & Bioinformatics Core Facility using the published pipeline (Sethi et al. BMC Genomics (2015) 16:584, DOI 10.1186/s12864-015-1793-9). All bioinformatics analysis was performed using R language. log RPKM was transformed from RPKM by $\log_2(RPKM+0.05)$. FASTQ data were deposited to GEO under GSE87452. A list containing 1811 genes named "Differentially expressed coding genes between Naive and Prime (DENvP_coding)" was defined by the following criteria: (1) min(log RPKM)>1; (2) |mean(log $RPKM_{naive}$)−mean(log $RPKM_{prime}$)|>1; (3) Benjamini and Hochberg—adjusted p value (FDR) 1%, in two-way ANOVA on the "Naive vs. Prime" factor. RNA-seq data of previously established inhibitor-dependent naive hPSCs (E-MTAB-2857, E-MTAB-2031, GSE87239, GSE63570, and single cell RNA-seq data from primed hESC and human preimplantation embryo (GSE36552, E-MTAB-3929) were downloaded from Gene Expression Omnibus (GEO) or European Bioinformatics Institute (EBI) databases. RPKM were calculated and log transformed by the same pipeline mentioned above. All datasets were merged by gene names, and each sample was quantile normalized to obtain the same distribution. Rank based Z score was calculated as well; it gave the similar PCA and clustering results. Expression level of the genes in DENvP_coding were extracted from the full dataset and used in the following analyses. In PCA analysis, single cell RNA-seq data on pre-implantation human blastocysts and primed hESCs were used to define the two-dimensional principle components space. All the other data points of hPSCs and other cells in early embryonic stage (E5, E6, E7) were projected to this space. Unsupervised clustering was built on spearman correlation matrix. Result was visualized as phylogenic tree using the ape package. Heatmap was generated with heatmap.2 function in gplot package. For the gene expression analysis on different chromosomes in FIG. 3c, |mean(log RPKMnaive)−mean(log RPKMprimed)| was calculated for the genes with min(log RPKM)>1. Genes in autosomes were grouped by the chromosome in which they locate. Genes in X chromosome were grouped into X-inactivated ($X_i$) genes and genes escaped from X inactivation ($X_e$) according to previous report (Court et al., *Genome Res.* 24, 554-569 (2014)). P values in two tailed t-test were adjusted with Benjamini and Hochberg method.

Bioinformatics Analysis of Transposable Element (TE)

Two different mapping and analyzing were performed. First, raw RNA-seq reads were mapped to TE reference map using following command "tophat -g1 --b2-sensitive --no-novel-juncs --no-novel-indels -o $outputdir --transcriptome-index=$transcriptome $index $reads". Counts for individual TE were normalized by number of total reads and transformed by $\log_2$(Normalized-count+1) to generate relative expression level. A list containing 889 TEs named "Differentially expressed transposable elements between Naive and Prime (DENvP_TE)" was defined with the same criteria used in the analysis of coding genes, except that relative expression level was used instead of RPKM. Relative expression level of these TEs in previously established naive and primed hPSCs were extracted following the same pipeline. Heatmap and clustering was built on Spearman correlation matrix using heatmap.2 function in gplot package. Second, raw RNA-seq reads of our own and other naive and primed hPSCs were aligned to repbase consensus sequences (downloaded from RepBase) with bowtie using the command "bowtie -q -p 8 -S -n 2 -e 70-l 28-maxbts 800 -k 1 -best". Counts for individual TE group were normalized by number of total reads and transformed using log 2(Normalized-count+1). Naive and primed hPSCs from the same laboratory were treated as a pair. Each TE group in each naive and primed hPSCs pairs were plotted on a scatter plot in FIG. 2o. Data points corresponding to HERVK and LTR5_Hs were highlighted.

Determination of Allelic Expression

Allelic read counts and heterozygotic SNPs were generated with ASEQ using GENOTYPE mode for X-chromosome SNVs available in dbSNP (build 146). Heterozygtic SNPs were identified as having a total read coverage above 5 with an alternative base frequency between 0.2-0.8. Each RNA-seq dataset was analyzed separately and the union of all heterozygous SNPs was used to examine allelic expression. Allelic expression for representative genes containing significant coverage (>5) per experimental replicate at known X-inactivated or X-escaped genes are shown in FIGS. 3d and e, respectively.

Genome-Wide DNA Methylation Study and Bioinformatics Analysis

Infinium MethylationEPIC Beadchip assay was performed on primed H9 (H9), naive H9 (nH9), primed RUES2 (RUES2), and naive RUES2 (nRUES2) with 4 biological replicates for each line at RPCI Genomics Shared Resource. Genomic DNA was extracted and purified using QIAamp DNA Blood Mini Kit (QIAGEN). DNA methylation was determined using Infinium MethylationEPIC array (Illumina) with the Infinium HD Assay Methylation Protocol. 500 ng of genomic DNA for each samples is bisulfite converted with EZ DNA Methylation-Gold Kit (Zymo Research), then 200 ng of each converted sample is amplified, fragmented, loaded into the Methylation EPIC Bead-Chips and hybridized overnight. Following washing, staining, and addition of a protective coating, the BeadChips are imaged using the Illumina iScan Reader to measure the fluorescence intensity of each probe for both methylation and unmethylated DNA. BeadChip data files are analyzed with Illumina's GenomeStudio (v2011.1) methylation module (v1.9.0) to report control normalization with background subtraction methylation data. Idat files were input into RnBeads package in R with an additional, customized annotation of imprinting region. One sample of naive H9 failed in quality control and was discarded in subsequent analysis. Probes were filtered and signal of each probe was normalized by default pipeline. Principle component analysis (PCA) was a direct output of RnBeads using beta value of all sites. Averaged beta values for each tiling region (5 kb window by default), promoter, gene body and imprinting region were calculated by RnBeads. Differentially methylated regions were defined by FDR<0.01 in two-way ANOVA on "naive vs. primed".

Differentially methylated tiling regions were rank ordered by the differences between mean of beta values of naive and primed hPSCs. The scaled beta values of each region were visualized as heatmap with pheatmap function. Heatmap for the imprinting regions was built on Pearson correlation matrix. For visualization purpose, averaged beta values were rescaled on each imprinting region in heatmap.2 of gplot. Raw data and processed data for DNA methylation study were deposited to GEO under GSE102031.

Incorporation of Naive hPSCs in Mouse Embryos

All animal experiments on the injection of naive hPSCs to mouse blastocysts and the transfer of injected blastocysts to pseudopregnant mice were performed by Gene Targeting and Transgenic Resource of Roswell Park Cancer Institute (RPCI) following IACUC and SCRO approvals. All animal experiments were done by RPCI staff members in the core facility in blinded fashion. The persons who performed the animal procedures only knew the codes assigned to the cells, not what kind of cells they were. The facility had not previously injected any human cells to mouse embryos; we were the only group that requested such service. They did the injection in our absence. Naive hPSCs (nRUES2, nRUES2::GFP, nC005::GFP and nH4::GFP) were plated at $2 \times 10^5$ cells per well on MEF cells in 12-well plates and cultured in 2iLI medium for 2 days. They were dissociated to single cells with TrypLE for 5-6 minutes and placed on 10 cm dishes for 45 minutes to remove MEF cells through attachment. The supernatant, which contained the hPSCs, was removed from the dish and centrifuged for 10 min at 2000 rpm. Cells in the pellet were resuspended in Mouse Blastocysts Injection Buffer (HEPES-buffered DMEM with 5% FBS). 10-12 naive hPSCs were injected to a C57BL/6J mouse blastocyst, which was obtained by superovulation from 3-4 week old C57BL/6J female mice. Injected blastocysts were transferred bilaterally to uterus of pseudopregnant CD-1 female mice at 7-9 weeks of age, with 14-18 blastocysts transferred per mouse. After 10.5 days or 17.5 days of gestation, mouse embryos were retrieved by RPCI staff and immediately euthanized by fixation in 4% paraformaldehyde for us to bring back to our laboratory at SUNY-Buffalo. The embryos were fixed in 4% PFA at 4° C. for 2 days and then transferred to 30% sucrose solution at 4° C. for 14-24 hr until the embryos sank to the bottom of the tube. The mouse embryos were then embedded in tissue freezing medium (Triangle Biomedical Sciences) and frozen in liquid nitrogen. Frozen embryo blocks were cut on a cryostat into 15 μm thick sections, which were placed on Ultra Plus Adhesion Slides (Thermo Scientific) for immunostaining. In some experiments, half of each mouse embryo cut sagittally was incubated in proteinase K solution (100 mM Tris-HCl pH8.0, 5 mM EDTA, 0.2% SDS, 200 mM NaCl, 250 g/ml Proteinase K) at 55° C. for 12-18 hours for extraction of genomic DNA. PCR amplification of the GFP gene in genomic DNA isolated from mouse embryos was performed using primers TCACGAACTCCAGCAGGAC-CATGT (SEQ ID NO:5) and TGACC-TACGGCGTGCAGTGCTTCA (SEQ ID NO:6). Human-specific DNA was detected by DNA fingerprinting using primers for D1 S80 VNTR GAAACTGGCCTC-CAAACACTGCCCGCCG (SEQ ID NO:7) and GTCTTGTTGGAGATGCACGTGCCCCTTGC (SEQ ID NO:8), or primers for TPA-25 Alu insert GTAAGAGTTCCGTAACAGGACAGCT (SEQ ID NO:9) and CCCCACCCTAGGAGAACTTCTCTTT (SEQ ID NO: 10).

Plasmid Constructs and Lentiviral Labeling of hPSCs

The LV-EF1a-GFP plasmid was provided by Su-chun Zhang at University of Wisconsin Madison. Lentivirus generated from this construct was used to label naive state N004 and C005 iPSCs. In earlier experiments, pLenti6/GFP lentivirus was used to label naive state RUES2 and H9. GFP-labeled naive hPSC lines were derived by picking GFP+ colonies after infected naive hPSCs were passaged to single cells using TrypLE. pEGFP-N1-TFE3 was purchased from Addgene (plasmid #38120). We mutated the nuclear localization signal of TFE3, $^{355}$ERRRRF (SEQ ID NO: 11) to $^{355}$EAAAAF (SEQ ID NO: 12). WT or NLS mutant TFE3-GFP fusion construct was subcloned to pLenti6-V5 (Thermo Fisher). Lentiviruses generated from these constructs were used to derive stable lines of primed H9 expressing either TFE-GFP or NLS-GFP.

Chromatin Immunoprecipitation

Primed H9 or naive H9 cells were crosslinked in 1% formaldehyde at room temperature for 10 min. After termination of crosslinking by adding 150 mM glycine, the cells were dissolved in SDS lysis buffer and sonicated on ice. Cleared lysates were used for immunoprecipitation with a ChIP assay kit (Millipore, Billerica, Mass., USA). Chromatin fragments were immunoprecipitated with 10 μg anti-H3K27AC antibody (Abcam). After removing proteins from DNA by proteinase K digestion, purified immunoprecipitated DNA was subjected to quantitative real-time PCR. Rabbit IgG was used as control. Primers for Oct4 distal enhancer (−2340/−2142): 5'-ACCCCACTGCCTTGTA-GACCT-3' (SEQ ID NO:13) and 5'-CACGCTGACCTCTGTCGACTT-3' (SEQ ID NO:14); Primers for Oct4 proximal enhancer (−1126/−1040): 5'-TCTGTTTCAGCAAAGGTTGGG-3'(SEQ ID NO: 15) and 5'-TTGGTCCCTACTTCCCCTTCA-3' (SEQ ID NO:16).

Statistical Analysis

SPSS 13.0 was used for statistical analysis. All data were expressed as mean±standard error of measurement. Statistical tests used to analyze whether samples are significantly different are indicted in the figure legends. Values of p<0.05 were considered statistically significant.

What is claimed is:

1. A method of producing mature human cells in a non-human animal comprising:
   a) generating human induced pluripotent stem cells (hiPSCs) from somatic cells of an individual;
   b) culturing the hiPSCs in a first culture medium comprising 5 mM glucose, 20 ng/mL human leukemia inhibitory factor (LIF), 1 mM glutamine, 5 mg/mL bovine serum albumin, 18 µg/ml human insulin, and kinase inhibitors, wherein the kinase inhibitors consist of 1 µM MEK inhibitor PD0325901, 0.8 µM GSK3β inhibitor CHIR99021, and 10 µM mTOR inhibitor Torin 1, in an environment comprising about 5% O₂ for about 3 hours, and wherein the first culture medium is free from B27 N2 supplements, and wherein, in the hiPSCs, expression of none of Oct4, Sox2, Klf4, c-Myc or Nanog transgenes are induced, thereby producing a population of cells;
   c) removing the first culture medium from the population of cells cultured in step b);
   d) then continuing to culture the population of cells produced in step b) in a second culture medium comprising 20 ng/mL LIF, 5 mM glucose 18 µ/ml human insulin, and kinase inhibitors, wherein the kinase inhibitors consist of 1 µM MEK inhibitor PD0325901, and 0.8 µM GSK3β inhibitor CHIR99021, in an environment sufficient for generating naive pluripotent stem cells for at least 5 hours, thereby producing a population of naive pluripotent stem cells;
   e) collecting and implanting the population of naive human pluripotent stem cells produced from step d) into a blastocyst of a non-human mammal;
   wherein after a gestation time, mature human cells grow in the non-human mammal.

2. A method of producing mature human cells in a non-human animal comprising:
   a) providing human embryonic stem cells (hESCs);
   b) culturing the hESCs in a first culture medium comprising 5 mM glucose, 20 ng/mL human leukemia inhibitory factor (LIF), 1 mM glutamine, 5 mg/mL bovine serum albumin, 18 µg/ml human insulin, and kinase inhibitors, wherein the kinase inhibitors consist of 1 µM MEK inhibitor PD0325901, 3 µM GSK3β inhibitor CHIR99021, and 10 µM mTOR inhibitor Torin 1, in an environment comprising about 5% O₂ for about 3 hours, and wherein the first culture medium is free from B27 or N2 supplements, thereby producing a population of cells;
   c) removing the first culture medium from the population of cells cultured in step b);
   d) then continuing to culture the population of cells produced in step b) in a second culture medium comprising 20 ng/mL LIF, 5 mM glucose, 18 µg/ml human insulin, and kinase inhibitors, wherein the kinase inhibitors consist of 1 µM MEK inhibitor PD0325901, and 3 µM GSK3β inhibitor CHIR99021, in an environment sufficient for generating naive pluripotent stem cells for at least 5 hours, thereby producing a population of naive pluripotent stem cells;
   e) collecting and implanting the population of naive human pluripotent stem cells produced from step d) into a blastocyst of a non-human mammal;
   wherein after a gestation time, mature human cells grow in the non-human mammal.

* * * * *

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence
<220> FEATURE:

```
<223> OTHER INFORMATION: Primer

<400> SEQUENCE: 1
gcaacattag cccaccgtgc tctc                                          24

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
ggttattaag atgtgtccca ggc                                           23

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ccccagggcc ccattttggt acc                                           23

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
aaagcagcgt atccacatag cgta                                          24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
tcacgaactc cagcaggacc atgt                                          24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
tgacctacgg cgtgcagtgc ttca                                          24

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
gaaactggcc tccaaacact gcccgccg                                      28
```

```
<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
gtcttgttgg agatgcacgt gccccttgc                              29

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
gtaagagttc cgtaacagga cagct                                  25

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
ccccacccta ggagaacttc tcttt                                  25

<210> SEQ ID NO 11
<211> LENGTH: 6
<212> TYPE: PRT
<213> ORGANISM: Artificial Sequence
<220> FEATURE:
<223> OTHER INFORMATION: Mutated TFE3

<400> SEQUENCE: 11

Glu Arg Arg Arg Arg Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Mutated TFE3

<400> SEQUENCE: 12

Glu Ala Ala Ala Ala Phe
1               5

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
accccactgc cttgtagacc t                                      21

<210> SEQ ID NO 14
<211> LENGTH: 21
<212> TYPE: DNA
<213> ORGANISM: Artificial Sequence
<220> FEATURE:
```

```
<223> OTHER INFORMATION: Primer

<400> SEQUENCE: 14
cacgctgacc tctgtcgact t                                            21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
tctgtttcag caaaggttgg g                                            21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16 ttggtccctta cttcccttc a                                            21
```